United States Patent
Vickers et al.

(10) Patent No.: US 9,672,329 B2
(45) Date of Patent: Jun. 6, 2017

(54) METHODS AND APPARATUSES FOR PREDICTING RISK OF PROSTATE CANCER AND PROSTATE GLAND VOLUME

(71) Applicants: Oy Arctic Partners Ab, Turku (FI); OPKO Diagnostics, LLC, Woburn, MA (US)

(72) Inventors: Andrew J. Vickers, Brooklyn, NY (US); Peter T. Scardino, New York, NY (US); Hans Lilja, New York, NY (US); Vincent Linder, Tewksbury, MA (US); David Steinmiller, Cambridge, MA (US)

(73) Assignees: OPKO Diagnostics, LLC, Woburn, MA (US); Oy Arctic Partners Ab, Turku (FI)

( * ) Notice: Subject to any disclaimer, the term of this patent is extended or adjusted under 35 U.S.C. 154(b) by 490 days.

(21) Appl. No.: 13/785,058

(22) Filed: Mar. 5, 2013

(65) Prior Publication Data

US 2013/0273643 A1 Oct. 17, 2013

Related U.S. Application Data

(60) Provisional application No. 61/606,554, filed on Mar. 5, 2012.

(30) Foreign Application Priority Data

Mar. 5, 2012 (FI) ...................................... 20125238

(51) Int. Cl.
| | |
|---|---|
| *G01N 33/48* | (2006.01) |
| *G06F 19/00* | (2011.01) |
| *G06F 19/18* | (2011.01) |
| *G06F 19/24* | (2011.01) |
| *B01L 3/00* | (2006.01) |
| *G01N 33/68* | (2006.01) |
| *G06G 7/48* | (2006.01) |

(52) U.S. Cl.
CPC ............ *G06F 19/366* (2013.01); *B01L 3/502* (2013.01); *B01L 3/502715* (2013.01); *G01N 33/6893* (2013.01); *G06F 19/18* (2013.01); *G06F 19/24* (2013.01); *B01L 2300/0654* (2013.01); *B01L 2300/087* (2013.01); *B01L 2300/0816* (2013.01); *B01L 2400/0487* (2013.01)

(58) Field of Classification Search
None
See application file for complete search history.

(56) References Cited

U.S. PATENT DOCUMENTS

| | | |
|---|---|---|
| 5,516,639 A | 5/1996 | Tindall et al. |
| 5,614,372 A | 3/1997 | Lilja et al. |
| 5,672,480 A | 9/1997 | Dowell et al. |
| 5,840,501 A | 11/1998 | Allard et al. |
| 5,939,533 A | 8/1999 | Lilja et al. |
| 5,945,289 A | 8/1999 | Lehrer |
| 7,605,003 B2 | 10/2009 | Chan et al. |
| 7,872,104 B2 | 1/2011 | Pettersson et al. |
| 7,951,529 B2 | 5/2011 | Li et al. |
| 8,173,433 B2 | 5/2012 | Folkman et al. |
| 2003/0235816 A1 | 12/2003 | Slawin et al. |
| 2004/0101914 A1 | 5/2004 | Pettersson et al. |
| 2007/0065954 A1 | 3/2007 | Taya et al. |
| 2011/0301863 A1 | 12/2011 | Auribault et al. |
| 2012/0022793 A1 | 1/2012 | Barker et al. |
| 2016/0025732 A1 | 1/2016 | Linder et al. |

FOREIGN PATENT DOCUMENTS

| | | |
|---|---|---|
| CN | 1973778 | 6/2007 |
| JP | 2009-524008 A | 6/2009 |
| WO | WO 97/39351 | 10/1997 |
| WO | WO 2007/109881 A1 | 10/2007 |
| WO | WO 2013/134179 A2 | 9/2013 |
| WO | WO 2013/172779 | 11/2013 |

OTHER PUBLICATIONS

International Search Report and Written Opinion for PCT/US2013/028978 mailed Jul. 18, 2013.
Benchikh, A. et al., "A panel of kallikrein markers can predict outcome of prostate biopsy following clinical work-up: An independent validation study from the European Randomized Study of Prostate Cancer screening, France," *BMC Cancer*, 10:635 (2010).
Chun, F. et al., "Development and external validation of an extended 10-core biopsy nomogram," *European Urology*, 52:436-445 (2007).
Editorial (Toimitus-Ajankohtaista Lääkärin käsikirjasta): Eturauhassyöpä. *Lääketieteellinen Aikakauskirja Duodecim*, (1):99-102 (2012).
Gupta, A. et al., "A four-kallikrein panel for the prediction of repeat prostate biopsy: Data from the European Randomized Study of Prostate Cancer Screening in Rotterdam, Netherlands," *Br. J. Cancer*, 103:708-714 (2010).
Hara, N. et al., "Total and free prostate-specific antigen indexes in prostate cancer screening: value and limitation for Japanese populations," *Asian J. Androl.*, 8(4):429-434 (2006).
Khan, Ma. et al., "Clinical utility of proPSA and "benign" PSA when percent free PSA is less than 15%," *Urology*, 64(6):1160-1164 (2004).
Lee, R. et al., "A meta-analysis of the performance characteristics of the free prostate-specific antigen test," *Urology*, 67(4):762-768 (2006).
Lilja, H. et al., "Prostate-specific antigen and prostate cancer: prediction, detection and monitoring," *Nat. Rev. Cancer*, 8(4):268-278 (2008).

(Continued)

Primary Examiner — Eric S Dejong
(74) Attorney, Agent, or Firm — Wolf, Greenfield & Sacks, P.C.

(57) ABSTRACT

Methods and apparatuses for predicting risk of prostate cancer and/or prostate gland volume are provided. More particularly, this disclosure relates to methods and apparatuses for providing the models and employing the models for predicting risk of prostate cancer and/or predicting prostate gland volume. The methods and apparatuses for predicting risk of prostate cancer and/or prostate gland volume are provided using, at least in part, information from a panel of kallikrein markers.

13 Claims, 18 Drawing Sheets

(56) References Cited

OTHER PUBLICATIONS

Michielsen, DPJ. et al., "Prediction of free PSA, PSA density and PSA density transition zone in the outcome of sextant prostate biopsies in patients with total PSA between 3 and 15 ng/ml," *UroOncology*, 4(2):71-76 (2004).

Nam, RK. et al., "Variants of the hK2 protein gene (KLK2) are associated with serum hK2 levels and predict the presence of prostate cancer at biopsy," *Clin. Cancer Res.*, 12(21):6452-6458 (2006).

Nam, RK. et al., "Assessing individual risk for prostate cancer," *J. Clin. Oncol.*, 25(24):3582-3588 (2007).

Nam, RK. et al., "Prospective multi-institutional study evaluating the performance of prostate cancer risk calculators," *J. Clin. Oncol.*, 29(22):2959-2964 (2011).

Parekh, DJ. et al., "External validation of the Prostate Cancer Prevention Trial risk calculator in a screened population," *Urology*, 68(6):1152-1155 (2006).

Peltola, MT. et al., "Intact and internally cleaved free prostate-specific antigen in patients with prostate cancer with different pathologic stages and grades," *Urology*, 77(4):1009.e1-1009.e8 (2011).

Sokoll, LJ. et al., "A prospective, multicenter, National Cancer Institute Early Detection Research Network study of [-2]proPSA: improving prostate cancer detection and correlating with cancer aggressiveness," *Cancer Epidemiol. Biomarkers Prev.*, 19(5):1193-1200 (2010).

Thompson, I. et al., "Assessing prostate cancer risk: results from the prostate cancer prevention trial," *J. Natl. Cancer Inst.*, 98:529-534 (2006).

Ulmert, D. et al., "Reproducibility and accuracy of measurements of free and total prostate-specific antigen in serum vs plasma after long-term storage at -20 degrees C," *Clin. Chem.*, 52(2):235-239 (2006).

Ulmert, D. et al, "Prostate-specific antigen at or before age 50 as a predictor of advance prostate cancer diagnosed up to 25 years later: A case-control study," *BMC Medicine*, 6(6):1-8 (2008).

van Vugt, HA. et al., "Prediction of prostate cancer in unscreened men: external validation of a risk calculator," *Eur. J. Cancer* 47(6):903-909 (2011).

Vickers, A. et al., "A panel of kallikrein markers can reduce unnecessary biopsy for prostate cancer: Data from the European Randomized Study of Prostate Cancer Screening in Goteborg, Sweden," *BMC Med.*, 6:19 (2008).

Vickers, A. et al., "A four-kallikrein panel predicts prostate cancer in men with recent screening: Data from the European Randomized Study of Prostate Cancer Screening, Rotterdam," *Clin. Cancer Res.*, 16(12):3232-3239 (2010).

Vickers, A. et al., "Impact of recent screening on predicting the outcome of prostate cancer biopsy in men with elevated PSA: Data from the European Randomized Study of Prostate Cancer Screening in Gothenburg, Sweden," *Cancer*, 116(11):2612-2620 (2010).

Vickers, A. et al., "Reducing unnecessary biopsy during prostate cancer screening using a four-kallikrein panel: An independent replication," *J. Clin. Oncol.*, 28(15):2493-2498 (2010).

Vickers, A. et al., "A panel of kallikrein marker predicts prostate cancer in a large, population-based cohort followed for 15 years without screening," *Cancer Epidemiol. Biomarkers Prev.*, 20(2):255-261 (2011).

Office Action for Finland Patent Application No. 20125238, mailed Jan. 10, 2013 and claims.

Becker et al., Sensitive and specific immunodetection of human glandular kallikrein 2 in serum. Clin Chem. Feb. 2000;46(2):198-206.

Eriksson et al., Dual-label time-resolved immunofluorometric assay of free and total prostate-specific antigen based on recombinant Fab fragments. Clin Chem. May 2000;46(5):658-66.

Genbank Accession No. 93091201.

Lilja et al., Prostate-specific antigen in serum occurs predominantly in complex with alpha 1-antichymotrypsin. Clin Chem. Sep. 1991;37(9):1618-25.

Lövgren et al., Enzymatic action of human glandular kallikrein 2 (hK2). Substrate specificity and regulation by Zn2+ and extracellular protease inhibitors. Eur J Biochem. Jun. 1999;262(3):781-9.

Lövgren et al., Production and activation of recombinant hK2 with propeptide mutations resulting in high expression levels. Eur J Biochem. Dec. 1999;266(3):1050-5.

Nurmikko et al., Production and characterization of novel anti-prostate-specific antigen (PSA) monoclonal antibodies that do not detect internally cleaved Lys145-Lys146 inactive PSA. Clin Chem. Oct. 2000;46(10):1610-8.

Piironen et al., Determination and analysis of antigenic epitopes of prostate specific antigen (PSA) and human glandular kallikrein 2 (hK2) using synthetic peptides and computer modeling. Protein Sci. Feb. 1998;7(2):259-69.

Rajakoski et al., Epitope mapping of human prostate specific antigen and glandular kallikrein expressed in insect cells. Prostate Cancer Prostatic Dis. Sep. 1997;1(1):16-20.

Vickers et al., Decision curve analysis: a novel method for evaluating prediction models. Med Decis Making. Nov.-Dec. 2006;26(6):565-74.

International Preliminary Report on Patentability for PCT/US2013/028978 mailed Sep. 18, 2014.

International Search Report and Written Opinion for PCT/US2015/023096 mailed Jul. 6, 2015.

Peltola et al., Immunoassay for the discrimination of free prostate-specific antigen (fPSA) forms with internal cleavages at $Lys_{145}$ or $Lys_{146}$ from fPSA without internal cleavages at $Lys_{145}$ or $Lys_{146}$. J Immunol Methods. Jun. 30, 2011;369(1-2):74-80. doi: 10.1016/j.jim.2011.04.006. Epub Apr. 28, 2011.

Talvitie, Delfia immunoassays: Guide to Converting ELISA Assays to DELFIA. PerkinElmer Life and Analytical Sciences. Dec. 18, 2006:1-16. Retrieved on Jun. 11, 2015 from http://www.perkinelmer.com/cmsresources/images/man_delfia_elisa_conversion.pdf.

Wenske et al., Evaluation of molecular forms of prostate-specific antigen and human kallikrein 2 in predicting biochemical failure after radical prostatectomy. Int J Cancer. Feb. 1, 2009;124(3):659-63. doi: 10.1002/ijc.23983.

Bryant et al., Predicting high-grade cancer at ten-core prostate biopsy using four kallikrein markers measured in blood in the ProtecT study. J Natl Cancer Inst. Apr. 11, 2015;107(7). pii: djv095. doi: 10.1093/jnci/djv095. Print Jul. 2015.

Carlsson et al., Predictive value of four kallikrein markers for pathologically insignificant compared with aggressive prostate cancer in radical prostatectomy specimens: results from the European randomized study of screening for prostate cancer section Rotterdam. Eur Urol. Nov. 2013;64(5):693-9.

Solovov et al., Estimation Effectiveness of Logistic Regression and Neural Network Analysis in Prostate Cancer Detection. Siberian Journal of Oncology. 2006;17(1):14-17.

Virtanen et al., Estimation of Prostate Cancer Probability by Logistic Regression: Free and Total Prostate-specific Antigen, Digital Rectal Examination, and Heredity Are Significant Variables. Clinical Chemistry. 1999;45(7):987-94.

METHODS AND APPARATUSES FOR PREDICTING RISK OF PROSTATE CANCER AND PROSTATE GLAND VOLUME

RELATED APPLICATIONS

This application claims the benefit of U.S. Provisional Patent Application Ser. No. 61/606,554, filed Mar. 5, 2012, entitled "Regression Models for Predicting Risk of Prostate Cancer and Prostate Gland Volume for a Male Person Based on Panel of Kallikrein Markers," by Vickers, et al., and Finland Patent Application No. 20125238, filed Mar. 5, 2012, entitled "Regression Models for Predicting Risk of Prostate Cancer and Prostate Gland Volume for a Male Person Based on Panel of Kallikrein Markers," by Vickers, et al., each of which is incorporated herein by reference in its entirety for all purposes.

FIELD OF THE INVENTION

This disclosure relates to methods and apparatuses for predicting risk of prostate cancer and/or prostate gland volume. More particularly this disclosure relates to methods and apparatuses for providing the models and employing the models for predicting risk of prostate cancer and/or predicting prostate gland volume.

BACKGROUND

Most men with an elevated blood level of total prostate-specific antigen (PSA)—the most common trigger for biopsy in US men—do not have prostate cancer. As a result, it has been estimated that there are close to 750,000 unnecessary prostate biopsies each year in the US. There is considerable evidence that measuring the isoforms of PSA separately, rather than combining them together in a single measure of total PSA, can help predict the presence of prostate cancer. These data include studies showing that cancer is predicted by free PSA, BPSA or –2proPSA. Indeed, free PSA is often measured separately, with urologists given results in terms of total PSA and free-to-total PSA ratio, with an estimated 10 million free PSAs measured per year. There is also evidence that hK2, the molecule that converts PSA from its pro- to active form, is informative of prostate risk. However, none of these markers on their own constitute good predictors of prostate biopsy outcome.

There have been several attempts to build predictive models for prostate cancer, most notably the "Prostate Cancer Prevention Trial Risk Calculator", the "Sunnybrook", and the European Randomized trial of Screening for Prostate Cancer (ERSPC) risk calculator. The problem with these models is that they require more or less extensive clinical work-up, that is, the patient needs to visit a urologist. For instance, the ERSPC risk calculator requires data on prostate volume, which is obtained by inserting an ultrasound probe into the rectum. Accordingly, new methods and apparatuses for predicting risk of prostate cancer and/or prostate gland volume would be beneficial.

SUMMARY OF THE INVENTION

Methods and apparatuses for predicting risk of prostate cancer and/or prostate gland volume are provided. More particularly, this disclosure relates to methods and apparatuses for providing the models and employing the models for predicting risk of prostate cancer and/or predicting prostate gland volume. In some embodiments, the methods and apparatuses for predicting risk of prostate cancer and/or prostate gland volume are provided using, at least in part, information from a panel of kallikrein markers. The subject matter of this application involves, in some cases, interrelated methods, alternative solutions to a particular problem, and/or a plurality of different uses of systems and devices.

One object of the present invention is to provide a method for obtaining a probability of an event using a logistic regression model for predicting the risk for a male person of prostate cancer.

In one set of embodiments, a computer for determining a probability of an event associated with prostate cancer is provided. The computer includes an input interface configured to receive information for a plurality of blood markers, wherein the information for the plurality of blood markers includes a free prostate-specific antigen (fPSA) value and a total PSA (tPSA) value. The computer also includes at least one processor programmed to evaluate a logistic regression model based, at least in part, on the received information to determine a probability of an event associated with prostate cancer in a person. Evaluating the logistic regression model comprises determining cubic spline terms for tPSA, wherein determining cubic spline terms for tPSA comprises determining the cubic spline terms for tPSA based on a first cubic spline having a first internal knot between 2-5 and a second internal knot between 5-8, determining cubic spline terms for fPSA, wherein determining cubic spline terms for fPSA comprises determining the cubic spline terms for fPSA based on a second cubic spline having a third internal knot between 0.25-1 and a fourth internal knot between 1.0-2.0, determining a first value for tPSA based, at least in part, on the received tPSA value and the determined cubic spline terms for tPSA, determining a second value for fPSA based, at least in part, on the received fPSA value and the determined cubic spline terms for fPSA, and determining the probability of the event associated with prostate cancer based, at least in part, on the first value and the second value. The computer also includes an output interface configured to output an indication of the probability of the event associated with prostate cancer.

In one set of embodiments, a system for determining a probability of an event associated with prostate cancer is provided. The system includes a detector configured to measure values for a plurality of blood markers, wherein the plurality of blood markers includes free prostate-specific antigen (fPSA), total PSA (tPSA), and intact PSA (iPSA). The system also includes at least one processor in electronic communication with the detector. The at least one processor is programmed to evaluate a logistic regression model based, at least in part, on the measured values for fPSA, tPSA, and iPSA to determine a probability of an event associated with high grade prostate cancer in a person. Evaluating the logistic regression model comprises determining cubic spline terms for tPSA, wherein determining cubic spline terms for tPSA comprises determining the cubic spline terms for tPSA based on a first cubic spline having a first internal knot between 4-5 and a second internal knot between 6-8, determining cubic spline terms for fPSA, wherein determining cubic spline terms for fPSA comprises determining the cubic spline terms for fPSA based on a second cubic spline having a third internal knot between 0.25-1 and a fourth internal knot between 1.0-2.0, determining a first value for tPSA based, at least in part, on the received tPSA value and the determined cubic spline terms for tPSA, determining a second value for fPSA based, at least in part, on the received fPSA value and the determined cubic spline terms for fPSA, determining the probability of the event associated with prostate cancer based, at least in part, on the first value and the second value, and outputting an indication of the probability of the event associated with prostate cancer.

In one set of embodiments, a method for determining a probability of an event associated with prostate cancer is provided. The method comprises receiving, via an input interface, information for a plurality of blood markers, wherein the information for the plurality of blood markers includes a free prostate-specific antigen (fPSA) value and a total PSA (tPSA) value. The method further comprises evaluating, using at least one processor, a logistic regression model based, at least in part, on the received information to determine a probability of an event associated with prostate cancer in a person. Evaluating the logistic regression model comprises determining cubic spline terms for tPSA, wherein determining cubic spline terms for tPSA comprises determining the cubic spline terms for tPSA based on a first cubic spline having a first internal knot between 2-5 and a second internal knot between 5-8; determining cubic spline terms for fPSA, wherein determining cubic spline terms for fPSA comprises determining the cubic spline terms for fPSA based on a second cubic spline having a third internal knot between 0.25-1 and a fourth internal knot between 1.0-2.0, determining a first value for tPSA based, at least in part, on the received tPSA value and the determined cubic spline terms for tPSA, determining a second value for fPSA based, at least in part, on the received fPSA value and the determined cubic spline terms for fPSA, and determining the probability of the event associated with prostate cancer based, at least in part, on the first value and the second value. The method further comprises outputting an indication of the probability of the event associated with prostate cancer.

In one set of embodiments, a computer-readable storage medium encoded with a plurality of instructions that, when executed by a computer, perform a method for determining a probability of an event associated with prostate cancer is provided. The method comprises receiving information for a plurality of blood markers, wherein the information for the plurality of blood markers includes a free prostate-specific antigen (fPSA) value and a total PSA (tPSA) value, evaluating a logistic regression model based, at least in part, on the received information to determine a probability of an event associated with prostate cancer in a person. Evaluating the logistic regression model comprises determining cubic spline terms for tPSA, wherein determining cubic spline terms for tPSA comprises determining the cubic spline terms for tPSA based on a first cubic spline having a first internal knot between 2-5 and a second internal knot between 5-8, determining cubic spline terms for fPSA, wherein determining cubic spline terms for fPSA comprises determining the cubic spline terms for fPSA based on a second cubic spline having a third internal knot between 0.25-1 and a fourth internal knot between 1.0-2.0, determining a first value for tPSA based, at least in part, on the received tPSA value and the determined cubic spline terms for tPSA, determining a second value for fPSA based, at least in part, on the received fPSA value and the determined cubic spline terms for fPSA, and determining the probability of the event associated with prostate cancer based, at least in part, on the first value and the second value. The method further comprises outputting an indication of the probability of the event associated with prostate cancer.

In one set of embodiments, a computer for determining a probability of an event associated with prostate cancer is provided. The computer includes an input interface configured to receive information for a plurality of blood markers, wherein the information for the plurality of blood markers includes a free prostate-specific antigen (fPSA) value, a total PSA (tPSA) value, an intact PSA (iPSA) value, and a human kallikrein 2 (kK2) value. The computer also includes at least one processor programmed to evaluate a logistic regression model based, at least in part, on the received information to determine a probability of an event associated with prostate cancer in a person. Evaluating the logistic regression model comprises determining the probability of the event associated with prostate cancer based, at least in part, on the tPSA value, the iPSA value, the hK2 value, and a ratio of the fPSA value to the tPSA value. The computer also includes an output interface configured to output an indication of the probability of the event associated with prostate cancer.

In one set of embodiments, a method for determining a probability of an event associated with prostate cancer is provided. The method comprises receiving, via an input interface, information for a plurality of blood markers, wherein the information for the plurality of blood markers includes a free prostate-specific antigen (fPSA) value, a total PSA (tPSA) value, an intact PSA (iPSA) value, and a human kallikrein 2 (kK2) value, evaluating, using at least one processor, a logistic regression model based, at least in part, on the received information to determine a probability of an event associated with prostate cancer in a person. Evaluating the logistic regression model comprises determining the probability of the event associated with prostate cancer based, at least in part, on the tPSA value, the iPSA value, the hK2 value, and a ratio of the fPSA value to the tPSA value, and outputting an indication of the probability of the event associated with prostate cancer.

In one set of embodiments, a computer-readable storage medium encoded with a plurality of instructions that, when executed by a computer, perform a method of determining a probability of an event associated with prostate cancer is provided. The method comprises receiving, via an input interface, information for a plurality of blood markers, wherein the information for the plurality of blood markers includes a free prostate-specific antigen (fPSA) value, a total PSA (tPSA) value, an intact PSA (iPSA) value, and a human kallikrein 2 (kK2) value, evaluating, using at least one processor, a logistic regression model based, at least in part, on the received information to determine a probability of an event associated with prostate cancer in a person. Evaluating the logistic regression model comprises determining the probability of the event associated with prostate cancer based, at least in part, on the tPSA value, the iPSA value, the hK2 value, and a ratio of the fPSA value to the tPSA value, and outputting an indication of the probability of the event associated with prostate cancer.

In one set of embodiments, a computer for determining a probability of an event associated with prostate cancer is provided. The computer includes an input interface configured to receive information for a plurality of blood markers, wherein the information for the plurality of blood markers includes a free prostate-specific antigen (fPSA) value, a total PSA (tPSA) value, an intact PSA (iPSA) value, and a human kallikrein 2 (kK2) value. The computer also includes at least one processor programmed to evaluate a logistic regression model based, at least in part, on the received information to determine a probability of an event associated with prostate cancer in a person. Evaluating the logistic regression model comprises determining a non-linear term for tPSA by raising the tPSA value to a first exponent, determining a non-linear term for fPSA by raising the fPSA value to a second exponent, and determining the probability of the event associated with prostate cancer based, at least in part, on the tPSA value, the fPSA value, the iPSA value, the hK2 value, the non-linear term for tPSA, and the non-linear term for fPSA. The computer further includes an output interface configured to output an indication of the probability of the event associated with prostate cancer.

In one set of embodiments, a method for determining a probability of an event associated with prostate cancer is provided. The method comprises receiving, via an input interface, information for a plurality of blood markers, wherein the information for the plurality of blood markers includes a free prostate-specific antigen (fPSA) value, a total PSA (tPSA) value, an intact PSA (iPSA) value, and a human kallikrein 2 (kK2) value. The method further comprises evaluating, using at least one processor, a logistic regression model based, at least in part, on the received information to determine a probability of an event associated with prostate cancer in a person. Evaluating the logistic regression model comprises determining a non-linear term for tPSA by raising the tPSA value to a first exponent, determining a non-linear term for fPSA by raising the fPSA value to a second exponent, and determining the probability of the event associated with prostate cancer based, at least in part, on the tPSA value, the fPSA value, the iPSA value, the hK2 value, the non-linear term for tPSA, and the non-linear term for fPSA. The method further comprises outputting an indication of the probability of the event associated with prostate cancer.

In one set of embodiments, a computer-readable storage medium encoded with a plurality of instructions that, when executed by a computer, perform a method of determining a probability of an event associated with prostate cancer is provided. The method comprises receiving information for a plurality of blood markers, wherein the information for the plurality of blood markers includes a free prostate-specific antigen (fPSA) value, a total PSA (tPSA) value, an intact PSA (iPSA) value, and a human kallikrein 2 (kK2) value. The method further comprises evaluating a logistic regression model based, at least in part, on the received information to determine a probability of an event associated with prostate cancer in a person. Evaluating the logistic regression model comprises determining a non-linear term for tPSA by raising the tPSA value to a first exponent, determining a non-linear term for fPSA by raising the fPSA value to a second exponent, and determining the probability of the event associated with prostate cancer based, at least in part, on the tPSA value, the fPSA value, the iPSA value, the hK2 value, the non-linear term for tPSA, and the non-linear term for fPSA. The method further comprises outputting an indication of the probability of the event associated with prostate cancer.

In one set of embodiments, a computer for determining a probability of an event associated with prostate cancer is provided. The computer includes an input interface configured to receive information for a plurality of blood markers, wherein the information for the plurality of blood markers includes a free prostate-specific antigen (fPSA) value, and a total PSA (tPSA) value, an intact PSA (iPSA) value, and a human kallikrein 2 (kK2) value. The computer also includes at least one processor programmed to evaluate a logistic regression model based, at least in part, on the received information to determine a probability of an event associated with prostate cancer in a person. Evaluating the logistic regression model comprises determining linear spline terms for tPSA, determining linear spline terms for fPSA, determining a first value for tPSA based, at least in part, on the received tPSA value and the determined linear spline terms for tPSA, determining a second value for fPSA based, at least in part, on the received fPSA value and the determined linear spline terms for fPSA, and determining the probability of the event associated with prostate cancer based, at least in part, on the first value and the second value. The computer also includes an output interface configured to output an indication of the probability of the event associated with prostate cancer.

In one set of embodiments, a method for determining a probability of an event associated with prostate cancer is provided. The method comprises receiving, via an input interface, information for a plurality of blood markers, wherein the information for the plurality of blood markers includes a free prostate-specific antigen (fPSA) value, a total PSA (tPSA) value, an intact PSA (iPSA) value, and a human kallikrein 2 (kK2) value. The method further comprises evaluating, using at least one processor, a logistic regression model based, at least in part, on the received information to determine a probability of an event associated with prostate cancer in a person. Evaluating the logistic regression model comprises determining linear spline terms for tPSA, determining linear spline terms for fPSA, determining a first value for tPSA based, at least in part, on the received tPSA value and the determined linear spline terms for tPSA, determining a second value for fPSA based, at least in part, on the received fPSA value and the determined linear spline terms for fPSA, and determining the probability of the event associated with prostate cancer based, at least in part, on the first value and the second value. The method further comprises outputting an indication of the probability of the event associated with prostate cancer.

In one set of embodiments, a computer-readable storage medium encoded with a plurality of instructions that, when executed by a computer, perform a method of determining a probability of an event associated with prostate cancer. The method comprises receiving information for a plurality of blood markers, wherein the information for the plurality of blood markers includes a free prostate-specific antigen (fPSA) value, a total PSA (tPSA) value, an intact PSA (iPSA) value, and a human kallikrein 2 (kK2) value. The method further comprises evaluating a logistic regression model based, at least in part, on the received information to determine a probability of an event associated with prostate cancer in a person. Evaluating the logistic regression model comprises determining linear spline terms for tPSA, determining linear spline terms for fPSA, determining a first value for tPSA based, at least in part, on the received tPSA value and the determined linear spline terms for tPSA, determining a second value for fPSA based, at least in part, on the received fPSA value and the determined linear spline terms for fPSA, and determining the probability of the event associated with prostate cancer based, at least in part, on the first value and the second value. The method further comprises outputting an indication of the probability of the event associated with prostate cancer.

In one set of embodiments, a system for determining a risk of high-grade cancer is provided. The system includes an input interface configured to receive information for a plurality of blood markers, wherein the information for the plurality of blood markers includes a free prostate-specific antigen (fPSA) value, a total PSA (tPSA) value, an intact PSA (iPSA) value, and an hK2 value. The system also includes at least one processor programmed to enter the received values into a logistic regression model, wherein at least the tPSA value and the fPSA values are entered into the logistic regression model using both linear and non-linear terms, and evaluate the logistic regression model to determine the risk of high-grade cancer.

In one set of embodiments, a system for determining a probability of an event associated with prostate cancer in a person is provided. The system includes a microfluidic sample analyzer, comprising a housing and an opening in the housing configured to receive a cassette having at least one microfluidic channel, wherein the housing includes a component configured to interface with a mating component on the cassette to detect the cassette within the housing. The system also includes a pressure-control system positioned within the housing, the pressure-control system configured to pressurize the at least one microfluidic channel in the cassette to move the sample through the at least one microfluidic channel. The system further includes an optical system positioned within the housing, the optical system including at least one light source and at least one detector spaced apart from the light source, wherein the light source is configured to pass light through the cassette when the cassette is inserted into the sample analyzer and wherein the detector is positioned opposite the light source to detect the amount of light that passes through the cassette. The system includes a user interface associated with the housing for inputting at least the age of a person, and a processor in electronic communication with the microfluidic sample analyzer, the processor programmed to evaluate a logistic regression model based, at least in part, on information received from the at least one detector to determine a probability of an event associated with prostate cancer in a person, wherein evaluating the logistic regression model comprises scaling each of a plurality of variables by a different coefficient value to produce scaled variables and summing values for the scaled variables used to produce the probability of the event associated with prostate cancer in a person, wherein the plurality of variables includes age and at least two variables included in the information received from the detector and is selected from the group consisting of fPSA, iPSA, and tPSA.

In one set of embodiments, a method for determining a probability of an event associated with prostate cancer in a person is provided. The method involves providing a microfluidic sample analyzer, comprising a housing, an opening in the housing configured to receive a cassette having at least one microfluidic channel, wherein the housing includes a component configured to interface with a mating component on the cassette to detect the cassette within the housing, and a pressure-control system positioned within the housing, the pressure-control system configured to pressurize the at least one microfluidic channel in the cassette to move the sample through the at least one microfluidic channel. The microfluidic sample analyzer also includes an optical system positioned within the housing, the optical system including at least one light source and at least one detector spaced apart from the light source, wherein the light source is configured to pass light through the cassette when the cassette is inserted into the sample analyzer and wherein the detector is positioned opposite the light source to detect the amount of light that passes through the cassette, and a user interface associated with the housing for inputting at least the age of a person. The method involves determining information for a plurality of blood markers using the microfluidic sample analyzer, wherein the information for the plurality of blood markers includes a free prostate-specific antigen (fPSA) value, a total PSA (tPSA) value, and an intact PSA (iPSA) value, and evaluating, using at least one processor, a logistic regression model based, at least in part, on the information to determine a probability of an event associated with prostate cancer in a person, wherein evaluating the logistic regression model comprises scaling each of a plurality of variables by a different coefficient value to produce scaled variables and summing values for the scaled variables used to produce the probability of the event associated with prostate cancer in a person, wherein the plurality of variables includes age and at least two variables included in the information received from the detector and is selected from the group consisting of fPSA, iPSA, and tPSA.

In one set of embodiments, a system is provided. The system includes a device comprising a first analysis region comprising a first binding partner, and a second analysis region comprising a second binding partner, wherein the first binding partner is adapted to bind with at least one of free prostate-specific antigen (fPSA), intact prostate-specific antigen (iPSA), and total PSA (tPSA), and wherein the second binding partner is adapted to bind with at least another of fPSA, iPSA, and tPSA. The system includes a detector associated with the first and second analysis regions, and a processor programmed to evaluate a logistic regression model based, at least in part, on information received from the detector to determine a probability of an event associated with prostate cancer in a person, wherein evaluating the logistic regression model comprises scaling each of a plurality of variables by a different coefficient value to produce scaled variables and summing values for the scaled variables used to produce the probability of the event associated with prostate cancer in a person, wherein the plurality of variables includes age and at least two variables included in the information received from the detector and is selected from the group consisting of fPSA, iPSA, and tPSA.

In one set of embodiments, a method is provided. The method comprises introducing a sample into a device comprising a first analysis region comprising a first binding partner, and a second analysis region comprising a second binding partner, wherein the first binding partner is adapted to bind with at least one of free prostate-specific antigen (fPSA), intact prostate-specific antigen (iPSA), and total PSA (tPSA), and wherein the second binding partner is adapted to bind with at least another of fPSA, iPSA, and tPSA. The method involves allowing any of the fPSA, iPSA and/or tPSA from the sample to bind with the first and/or second binding partners at the first and second analysis regions, determining a characteristic of fPSA, iPSA and/or tPSA using one or more detectors associated with the first and second analysis regions, inputting the characteristics of fPSA, iPSA and/or tPSA into a processor programmed to evaluate a logistic regression model based, at least in part, on information received from the at least one detector to determine a probability of an event associated with prostate cancer in a person, wherein evaluating the logistic regression model comprises scaling each of a plurality of variables by a different coefficient value to produce scaled variables and summing values for the scaled variables used to produce the probability of the event associated with prostate cancer in a person, wherein the plurality of variables includes age and at least two variables included in the information received from the detector and is selected from the group consisting of fPSA, iPSA, and tPSA, and determining the probability of the event associated with prostate cancer.

In one set of embodiments, a device is provided. The device includes a microfluidic system comprising a first microfluidic channel including at least one inlet and one outlet, a first reagent stored in the first microfluidic channel, a seal covering the inlet of the first microfluidic channel and a seal covering the outlet of the first microfluidic channel so as to store the first reagent in the first microfluidic channel, and a second microfluidic channel including at least one inlet and one outlet. The device also includes a first analysis region, a second analysis region, and a third analysis region, each of the analysis regions including one of an anti-iPSA specific capture antibody, an anti-fPSA specific capture antibody, and an anti-tPSA specific capture antibody, wherein one or more of the first, second and third analysis regions are in fluid communication with the second microfluidic channel. The device also includes a fluidic connector that can be connected to the microfluidic system, wherein the fluidic connector comprises a fluid path including a fluid path inlet and a fluid path outlet, wherein upon connection, the fluid path inlet connects to the outlet of the first microfluidic channel to allow fluid communication between the fluid path and the first microfluidic channel, and the fluid path outlet connects to the inlet of the second microfluidic channel to allow fluid communication between the fluid path and the second microfluidic channel, wherein the first and second microfluidic channels are not in fluid communication with one another absent connection via the fluidic connector. The device also includes a source of a metal colloid conjugated to an antibody that binds to anti-PSA.

In one set of embodiments, a method for obtaining a probability of an event using a logistic regression model for predicting the risk for a male person of prostate cancer is provided. The method comprises the steps of:

a) providing a logistic regression model obtained by employing multivariable logistic regression of data of a multitude of male persons, said data comprising for each male person of said multitude of male persons data on prostate cancer status, and data, preceding data of said prostate cancer status, comprising age; and determinations of blood markers, total prostate-specific antigen (tPSA), free PSA (fPSA), intact PSA (iPSA), and optionally human kallikrein 2 (hK2) from blood samples of said male persons, wherein said logistic regression model is generated employing formula:

$$\log\left(\frac{\pi}{1-\pi}\right) = \sum_{i=1}^{j} \beta_i x_i + c$$

wherein $\pi$ is the probability of said event, $\beta_i$ is the coefficient for variable $x_i$ for j variables comprising age, tPSA, fPSA, iPSA, and optionally hK2, respectively, to obtain said logistic regression model;

b) providing the age of a male person in years;
c) determining said blood markers
  i) tPSA,
  ii) fPSA,
  iii) iPSA,
  iv) optionally hK2, respectively, from a blood sample of said male person;
d) employing said logistic regression model using said provided age of step b) and said determined blood markers of step c) to obtain said probability of said event of said male person by
  i) defining employing formula:

$$y = \log\left(\frac{\pi}{1-\pi}\right),$$

and ii) obtaining said probability as $$\pi = \left(\frac{e^y}{1+e^y}\right)$$

Characteristic for the method is that in said logistic regression model said risk for cancer is based on tPSA alone if tPSA is ≥15 ng/ml, preferably ≥20 ng/ml and most preferably ≥25 ng/ml.

Another object of the present invention is to provide a method for predicting prostate gland volume using a linear regression model.

Embodiments of the present invention provide a method for predicting prostate gland volume using a linear regression model wherein said method comprises the steps of:

a) providing a linear regression model obtained by employing linear regression of data of a multitude of male persons, said data comprising for each male person of said multitude of male persons
  i) data on prostate gland volume, and
  ii) data, preceding data on prostate gland volume, comprising age; and determinations of blood markers: total prostate-specific antigen (tPSA), free PSA (fPSA), intact PSA (iPSA), and optionally, human kallikrein 2 (hK2), from blood samples of said male persons, wherein said linear regression model is generated employing formula:

$$V = \sum_{i=1}^{j} \beta_i x_i + c,$$

wherein V is prostate gland volume, $\beta_i$ is the coefficient for variable $x_i$; for j variables comprising age, tPSA, fPSA, iPSA, and optionally hK2, respectively, to obtain said linear regression model;

b) providing the age of a male person in years;
c) determining said blood markers, tPSA, fPSA, iPSA, and optionally, hK2, respectively, from a blood sample of said male person;
d) employing said linear regression model using said provided age of step b) and said determined blood markers of step c) to obtain said predicted prostate volume of said male person.

Characteristic for the method is that in said linear regression model said risk for cancer is based on tPSA alone if tPSA is ≥15 ng/ml, preferably ≥20 ng/ml and most preferably ≥25 ng/ml.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION OF THE INVENTION

Figure 1:
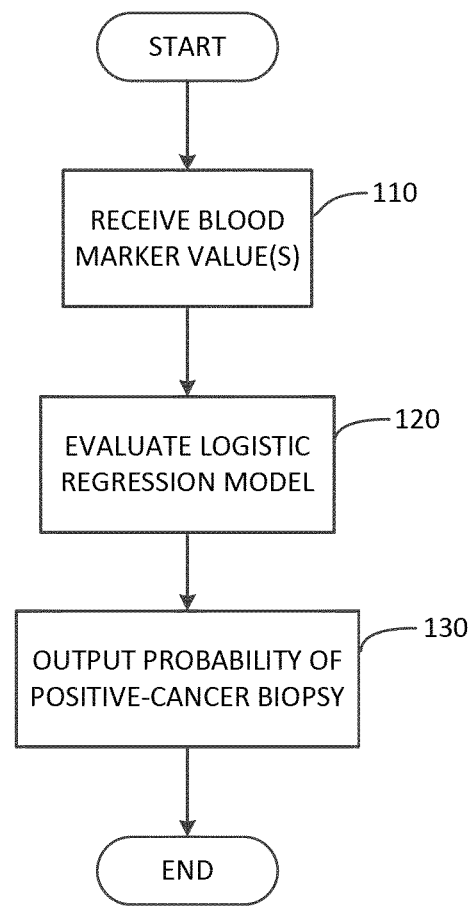
FIG. 1 illustrates a flow chart of a process for determining a probability of a positive cancer biopsy in accordance with some embodiments of the invention.

As discussed above, many conventional techniques for predicting a probability of prostate cancer and/or prostate gland volume are based, at least in part, on a clinical examination (e.g., a digital rectal exam or DRE) of the patient. Some embodiments described herein relate to methods and apparatuses for determining a predicted probability of prostate cancer and/or prostate gland volume based, at least in part, on a panel of blood markers, without the need for a clinical work-up. As discussed in further detail below, the provided predicted probability of prostate cancer on biopsy and/or prostate gland volume is a reliable metric that may be useful in aiding decisions related to prostate biopsy.

Some embodiments are directed to a computer system including at least one processor programmed to assess a risk of prostate cancer, wherein the risk of prostate cancer is determined based, at least in part, on values for a plurality of blood markers. In some embodiments, the computer system may be implemented as an integrated system (e.g., on an analyzer and/or a chip/cassette) with one or more detectors that determine a value for one or more of the blood markers described herein. In other embodiments, the computer system may include a computer remotely located from the one or more detectors, and values for one or more of the blood markers described herein may be manually entered using a user interface and/or the values may be received via a network interface communicatively coupled to a network (e.g., the Internet). The at least one processor in the computer system may be programmed to apply one or more models to received inputs to evaluate a risk of prostate cancer upon biopsy, as discussed in more detail below.

Models used in accordance with some embodiments of the invention help to integrate information for a plurality of input factors. For example, the input factors may be PSA, free-to-total PSA ratio, and/or digital rectal exam (DRE) status. Continuing with this example, a first patient may have a PSA of 3 ng/ml, a free-to-total PSA ratio of 15%, and a negative DRE, a second patient may have a PSA of 9.5 ng/ml, a free-to-total PSA ratio of 50%, and a negative DRE, and a third patient may have a PSA of 1.5 ng/ml, a free-to-total ratio of 29%, and a positive DRE. For the first patient, a urologist may wonder whether the low (but not extremely low) free-to-total PSA ratio is enough to warrant biopsy given that PSA is moderate and DRE negative. For the second patient, the high PSA value would normally warrant an immediate biopsy, but the very high free-to-total PSA ratio may be a strong indication that the PSA rise is benign. For the third patient, a positive DRE is normally a very worrying sign, but may be insufficient evidence that a biopsy is needed given the low PSA and normal free-to-total PSA ratio. As should be appreciated from the foregoing, when a physician is presented with these factors in isolation, it may be difficult to determine when a biopsy is needed. Additionally, as the number of input factors increases, the decision of whether to perform a biopsy based on the numerical information for the various input factors becomes even more complex.

Both patients and clinicians vary with respect to the propensity that they will opt for biopsy, depending on differences as to how they value early detection of cancer compared to the risks, harms and inconvenience of biopsy. It is often impractical to incorporate such preferences using strict decision rules (e.g. perform biopsy if PSA>4 ng/ml OR free-to-total ratio <15%) or using risk scores (e.g. prostate health index (PHI) score of 29). For example, if a man were averse to medical procedures, it may difficult to determine how high of a PSA and/or PHI score would be "high enough" to warrant biopsy.

Rather than using strict decision rules, in accordance with some embodiments, at least one processor is programmed to use one or more statistical models to process a plurality of inputs to guide decisions about prostate biopsy. Inputs to the statistical models may include, but are not limited to, blood marker values, patient characteristics (e.g., age), and other suitable information, to a determine a probability that a positive biopsy for prostate cancer will be found. Such a probability represents an interpretable scale that may be used to guide biopsy decisions in view of patient and clinician preferences.

FIG. 1 illustrates a flowchart of a process in accordance with some embodiments of the invention. In act 110, one or more values for blood markers are received by at least one processor for processing using one or more of the techniques described herein. As described in more detail below, the blood marker value(s) may be received in any suitable way including, but not limited to, through a local input interface such as a keyboard, touch screen, microphone, or other input device, from a network-connected interface that receives the value(s) from a device located remote from the processor(s), or directly from one or more detectors that measure the blood marker value(s) (e.g., in an implementation where the processor(s) are integrated with a measurement device that includes the one or more detectors).

In response to receiving the blood marker value(s), the process proceeds to act 120, where at least one logistic regression model is evaluated to determine a probability of a positive biopsy for prostate cancer, wherein the probability is based, at least in part, on the received blood marker value(s). As described in further detail below, information other than the received blood marker values (e.g., age, cancer grade, etc.) may optionally be used as factors in determining a particular model to use and/or used as input factors to evaluate a selected model.

After determining a probability of a positive-cancer biopsy, the process proceeds to act 130, where the probability is output to a user (e.g., a physician, a patient) to guide a decision process of whether a biopsy is needed. The probability may be output in any suitable way. For example, in some embodiments, the probability may be output by displaying a numeric value representing the probability on a display screen of a device. In other embodiments, the probability may be output using one or more lights or other visual indicators on a device. In yet other embodiments, the probability may be provided using audio output, tactile output, or some combination of one or more of audio, tactile, and visual output. In some embodiments, outputting the probability comprises sending information to a network-connected device to inform a user about the determined probability. For example, the probability may be determined by one or more processors located at a remote site, and an indication of the probability may be sent to an electronic device of a user (e.g., a physician) using one or more networks, in response to determining the probability at the remote site. The electronic device that provides output to a user in accordance with the techniques described herein may be any suitable device including, but not limited to, a laptop, desktop, or tablet computer, a smartphone, a pager, a personal digital assistant, and an electronic display.

As discussed above, some embodiments are directed to a method for obtaining a probability of an event using a logistic regression model for predicting the risk of prostate cancer and/or prostate gland volume for a male person. In some embodiments, the method involves including information from one or more kallikrein markers, namely total prostate-specific antigen (tPSA), free PSA (fPSA), intact PSA (iPSA), and human kallikrein 2 (hK2). Any suitable logistic regression model may be used, and the techniques described herein are not limited in this respect. In some embodiments, the probability of the event is determined in accordance with equation (I), reproduced below:

$$\text{Probability} = \frac{e^L}{1 + e^L} \quad (I)$$

where the logit (L) is determined using any of a plurality of logistic regression models. Non-limiting examples of nine different types of logistic regression models that may be used in accordance with the techniques described herein include:

1. Simple Model (tPSA Only)

$$L = \beta_0 + \beta_1(\text{Age}) + \beta_2(tPSA)$$

2. Four Assay Model Using Free/Total Ratio

In this model, the ratio of free PSA to total PSA is substituted for the free PSA term.

$$L = \beta_0 + \beta_1(\text{Age}) + \beta_2(tPSA) + \beta_3\left(\frac{fPSA}{tPSA}\right) + \beta_4(iPSA) + \beta_5(hK2)$$

3. Four Assay Model Using Log(tPSA) and Free/Total Ratio

In this model, the log of tPSA is substituted for the tPSA term to account for the increased contribution of this predictive factor.

$$L = \beta_0 + \beta_1(\text{Age}) + \beta_2(\log[tPSA]) + \beta_3\left(\frac{fPSA}{tPSA}\right) + \beta_4(iPSA) + \beta_5(hK2)$$

4. Polynomial Model

In this model, additional non-linear terms for tPSA and fPSA are included. In the example equation provided below, the square of tPSA is used to emphasize the direct relationship between this term and risk of prostate cancer, and the square root of the free/total PSA term is used to reflect the inverse association of this term with risk. It should be appreciated however, that polynomial terms of higher order (e.g., cubic) may also be included in some embodiments.

$$L = \beta_0 + \beta_1(\text{Age}) + \beta_2(tPSA) + \beta_3(fPSA) + \\ \beta_4(iPSA) + \beta_5(hK2) + \beta_6(tPSA^2) + \beta_7\left(\sqrt{\frac{fPSA}{tPSA}}\right)$$

5. Linear Splines for all Four Assays

In this model, linear splines are added, with a single knot at the median value. The splines may be determined using the following equations:

$$sp1(x) = x \text{ if } x < \text{knot}$$

$$sp1(x) = \text{knot if } x \geq \text{knot}$$

$$sp2(x) = 0 \text{ if } x < \text{knot}$$

$$sp2(x) = x - \text{knot if } x \geq \text{knot}$$

with the model being represented as:

$$L = \beta_0 + \beta_1(\text{Age}) + \beta_2(tPSA) + \beta_3(fPSA) + \beta_4(iPSA) + \beta_5(hK2) +$$
$$\beta_6(sp1[tPSA]) + \beta_7(sp2[tPSA]) + \beta_8(sp1[fPSA]) + \beta_9(sp2[fPSA]) +$$
$$\beta_{10}(sp1[iPSA]) + \beta_{11}(sp2[iPSA]) + \beta_{12}(sp1[hK2]) + \beta_{13}(sp2[hK2])$$

6. Linear Splines for tPSA and fPSA

In this model, linear splines are included only for tPSA and fPSA to reduce the number of variables and simplify the model.

$$L=\beta_0+\beta_1(\text{Age})+\beta_2(tPSA)+\beta_3(fPSA)+\beta_4(iPSA)+\beta_5(hK2)+\beta_6(sp1[tPSA])+\beta_7(sp2[tPSA])+\beta_8(sp1[fPSA])+\beta_9(sp2[fPSA])$$

7. Cubic Splines for all Four Assays

In this model, cubic splines are included for each term. In the example provided below, a cubic spline with four knots is described. It should be appreciated, however, that a cubic spline using any suitable number of knots including, but not limited to, five knots, six knots, seven knots, and eight knots, may alternatively be used. The splines may be determined using the following equations:

$$sp[x]1 = \max([x] - \text{knot1}, 0)^3 - \max([x] - \text{knot3}, 0)^3 \frac{\text{knot4} - \text{knot1}}{\text{knot4} - \text{knot3}} +$$
$$\max([x] - \text{knot4}, 0)^3 \frac{\text{knot3} - \text{knot1}}{\text{knot4} - \text{knot3}}$$

$$sp[x]2 = \max([x] - \text{knot2}, 0)^3 - \max([x] - \text{knot3}, 0)^3 \frac{\text{knot4} - \text{knot2}}{\text{knot4} - \text{knot3}} +$$
$$\max([x] - \text{knot2}, 0)^3 \frac{\text{knot3} - \text{knot2}}{\text{knot4} - \text{knot3}}$$

where knot1 and knot4 are external knots for the cubic spline, and knot2 and knot3 are internal knots for the cubic spline. In some embodiments, the internal knots are specified within the range of between about 2 to about 5 and between about 5 to about 8 for tPSA, between about 0.25 to about 1 and between about 1.0 to about 2.0 for fPSA, between about 0.2 to about 0.5 and between about 0.4 to about 0.8 for iPSA, and between about 0.02 to about 0.04 and between about 0.04 to about 0.08 for hK2. For example, in one implementation, values of 3.89 and 5.54 are used for the internal knots for tPSA, values of 0.81 and 1.19 are used for the internal knots for fPSA, values of 0.3 and 0.51 are used for the internal knots of iPSA, and values of 0.036 and 0.056 are used for the internal knots of kK2.

In certain embodiments, one or more internal knots for tPSA may independently be in the range of between about 3 to about 5, between about 3 to about 6, between about 2.5 to about 6, between about 2.5 to about 6.5, between about 5 to about 8, between about 5.5 to about 8, between about 5 to about 9, between about 5 to about 10, between about 1 to about 5, between about 1 to about 4, and between about 1 to about 3. Other ranges are also possible.

In certain embodiments, one or more internal knots for fPSA may independently be in the range of between about 0.1 to about 1.0, between about 0.1 to about 1.2, between about 0.3 to about 0.8, between about 0.4 to about 0.9, between about 0.5 to about 1.2, between about 0.7 to about 1.4, between about 0.7 to about 0.9, between about 1.1 to about 1.6, between about 1.1 to about 1.2, and between about 1.1 to about 2. Other ranges are also possible.

In certain embodiments, one or more internal knots for iPSA may independently be in the range of between about 0.05 to about 0.5, between about 0.1 to about 0.5, between about 0.2 to about 0.5, between about 0.1 to about 0.8, between about 0.2 to about 0.8, between about 0.4 to about 0.8, between about 0.4 to about 1.0, between about 0.3 to about 0.6, between about 0.5 to about 1.0, and between about 0.6 to about 0.8. Other ranges are also possible.

In certain embodiments, one or more internal knots for hK2 may independently be in the range of between about 0.01 to about 0.03, between about 0.01 to about 0.04, between about 0.01 to about 0.05, between about 0.02 to about 0.05, between about 0.02 to about 0.06, between about 0.03 to about 0.05, between about 0.4 to about 0.07, between about 0.04 to about 1.0, between about 0.5 to about 1.0, and between about 0.6 to about 1.0. Other ranges are also possible.

As discussed above, cubic splines incorporating any suitable number of internal knots (e.g., three, four, five, six internal knots) may be used, and the example of a cubic spline including two internal knots is provided merely for illustration and not limitation. In embodiments that include more than two internal knots, the knots may be placed within one or more of the ranges discussed above, or in some other suitable range. For example, in some embodiments, the knots may be specified such that the length of the segments of the spline between each of the pairs of neighboring knots is essentially equal.

The model may be represented as:

$$L = \beta_0 + \beta_1(\text{Age}) + \beta_2(tPSA) + \beta_3(fPSA) + \beta_4(iPSA) + \beta_5(hK2) +$$
$$\beta_6(sp1[tPSA]) + \beta_7(sp2[tPSA]) + \beta_8(sp1[fPSA]) + \beta_9(sp2[fPSA]) +$$
$$\beta_{10}(sp1[iPSA]) + \beta_{11}(sp2[iPSA]) + \beta_{12}(sp1[hK2]) + \beta_{13}(sp2[hK2])$$

8. Cubic Splines for tPSA and fPSA

In this model, cubic splines are included only for tPSA and fPSA to reduce the number of variables and simplify the model.

In certain embodiments, the internal knots for tPSA and fPSA are specified using one or more of the ranges described above with respect to the cubic spline model for all four assays. For example, internal knots may be specified within the range of between about 2 to about 5 and between about 5 to about 8 for tPSA, and between about 0.5 to about 1 and between about 1.0 to about 1.5 for fPSA. For example, in one implementation, values of 3.89 and 5.54 are used for the internal knots for tPSA and values of 0.81 and 1.19 are used for the internal knots for fPSA. It should be appreciated, however, that other values and/or ranges may alternatively be used. Additionally, it should be appreciated that any number of knots (e.g., other than four knots) may alternatively be used in some embodiments, as discussed above with respect to the cubic spline model for all four assays.

The model may be represented as:

$$L=\beta_0+\beta_1(\text{Age})+\beta_2(tPSA)+\beta_3(fPSA)+\beta_4(iPSA)+\beta_5(hK2)+\beta_6(sp1[tPSA])+\beta_7(sp2[tPSA])+\beta_8(sp1[fPSA])+\beta_9(sp2[fPSA])$$

9. Age Stratified, Cubic Splines for tPSA and fPSA

In this model, cubic splines are applied to a dataset in two parts to generate different coefficients (β) for use with patients having an age less than or greater than/equal to a particular age (e.g., age 65). Accordingly, in this model, the same representation (using different coefficient values) is used for both groups of patients. Examples of the different coefficients that may be used with this model are provided below in Table 1.

The model may be represented as:

If Age <65:

$$L=\beta_0+\beta_1(Age)+\beta_2(tPSA)+\beta_3(fPSA)+\beta_4(iPSA)+\beta_5(hK2)+\beta_6(sp1[tPSA])+\beta_7(sp2[tPSA])+\beta_8(sp1[fPSA])+\beta_9(sp2[fPSA])$$

If Age ≥65:

$$L=\beta_0+\beta_1(Age)+\beta_2(tPSA)+\beta_3(fPSA)+\beta_4(iPSA)+\beta_5(hK2)+\beta_6(sp1[tPSA])+\beta_7(sp2[tPSA])+\beta_8(sp1[fPSA])+\beta_9(sp2[fPSA])$$

Each of the above-described logistic regression models includes a plurality of input factors, including age, and blood marker values for one or more of total PSA (tPSA), free PSA (fPSA), intact PSA (iPSA), and human kallikrein 2 (hK2). In some cases, the blood marker values are concentrations of the blood markers in a patient sample. In some of the above-described logistic regression models, linear or cubic splines for the non-linear terms are determined. It should be appreciated that higher-order splines may alternatively be used, as the techniques described herein are not limited in this respect.

For the above-described logistic regression models, each of the terms is multiplied by a corresponding coefficient value (β). The coefficients may be determined in any suitable way. For example, each of the models may be applied to a dataset including patient information, serum assay results, and biopsy results. A best fit of each of the models to the information in the dataset to predict cancer may be determined and the coefficients corresponding to the best fit result may be used in accordance with the techniques described herein. An example table of coefficients determined for each of the models described above, is shown below in Table 1. For these models, age is input in years and each assay result is measured in ng/mL.

determine probabilities of a positive biopsy for different grades of cancer. For example, embodiments used to determine a probability a of high-grade cancer (e.g., Gleason score ≥7) positive biopsy may use different coefficients for one or more of the models than embodiments used to determine a probability of a low-grade cancer positive biopsy. Additionally, different coefficients may be used based, at least, in part, on whether one or more of the blood marker values were determined from serum or from plasma.

Figure 2:
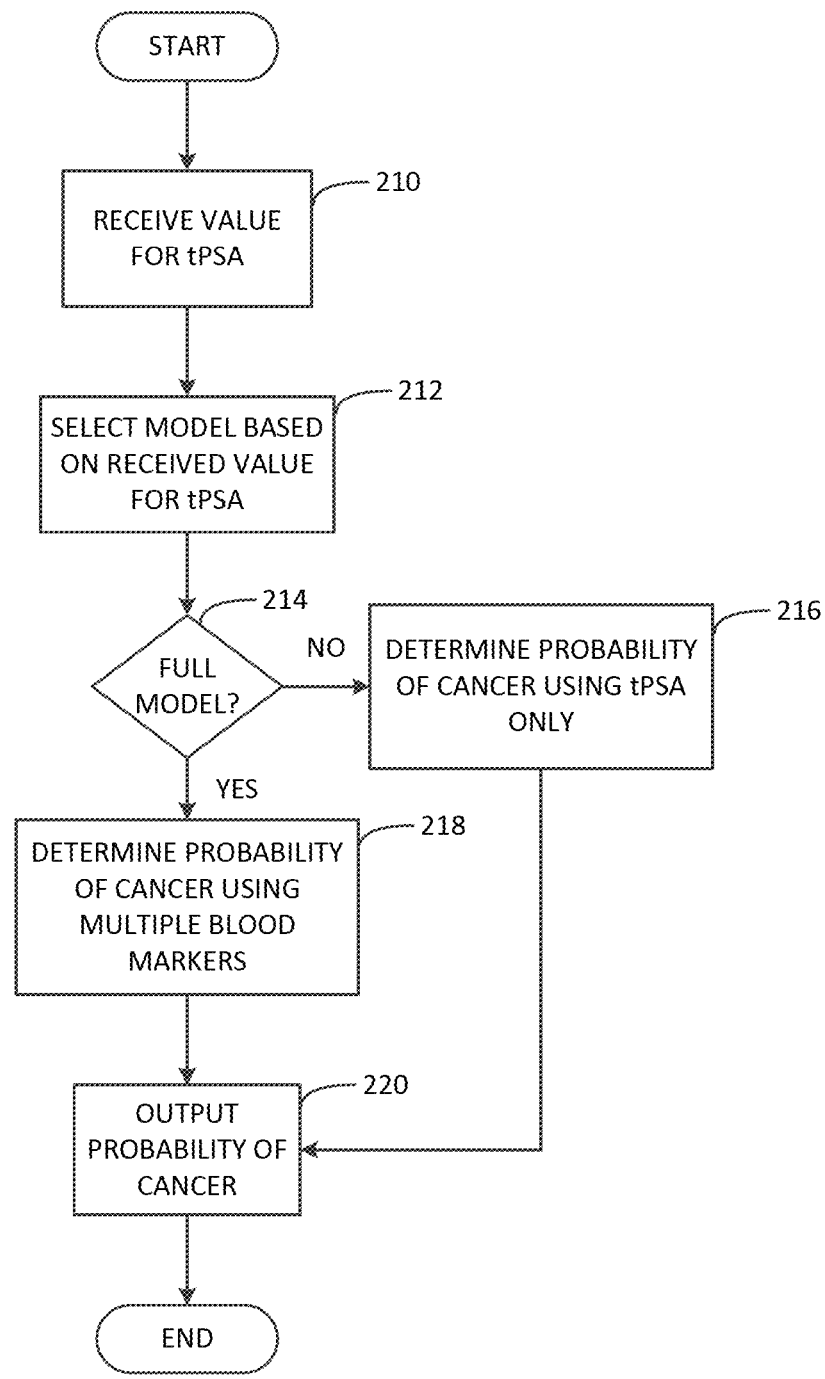
FIG. 2 illustrates a flow chart of a process for conditionally selecting a logistic regression model in accordance with some embodiments of the invention.

In some embodiments, a first logistic regression model may be used when a value for one or more of the markers is above a certain threshold, and a second logistic regression model may be used when the value is below the threshold. FIG. 2 illustrates a process for selecting a logistic regression model based on a threshold in accordance with some embodiments of the invention. In act 210, a value for the blood marker total PSA (tPSA) is received. Although the illustrative process of FIG. 2 uses tPSA as a blood marker value to determine which logistic regression model to use, it should be appreciated that any other blood marker value, combination of blood marker values, or any other suitable information may alternatively be used. Accordingly, in some embodiments, at least one processor may be programmed to implement and select from a plurality of models based, at least in part, on one or more input values.

After receiving the value for tPSA, the process proceeds to act 212, where a logistic regression model is selected based, at least in part, on the received tPSA value. For example, in one implementation, when the value of tPSA is ≥15 ng/ml, preferably ≥20 ng/ml and most preferably ≥25 ng/ml, the logistic regression model may be based on tPSA alone (e.g., the "Simple Model (tPSA only)" model described above may be used). For this implementation, when the tPSA value is less than a particular threshold (e.g., less than 15 ng/ml), one or more of the other logistic regression models may be selected.

TABLE 1

Exemplary coefficients (β) for each of the nine linear regression models discussed above. The coefficients were determined based on a best fit of each model to a dataset including information from 1420 individuals.

| model | $\beta_0$ | $\beta_1$ | $\beta_2$ | $\beta_3$ | $\beta_4$ | $\beta_5$ | $\beta_6$ | $\beta_7$ | $\beta_8$ | $\beta_9$ | $\beta_{10}$ | $\beta_{11}$ | $\beta_{12}$ | $\beta_{13}$ |
|---|---|---|---|---|---|---|---|---|---|---|---|---|---|---|
| 1 | −2.434 | 0.015 | 0.165 | | | | | | | | | | | |
| 2 | −2.130 | 0.040 | 0.071 | −8.721 | −0.268 | 11.136 | | | | | | | | |
| 3 | −2.243 | 0.041 | 0.310 | −9.306 | −0.060 | 11.035 | | | | | | | | |
| 4 | 1.483 | 0.042 | 0.013 | 7.789 | −0.137 | 11.198 | 0.002 | −15.612 | | | | | | |
| 5 | −4.218 | 0.042 | 0.286 | −1.395 | 0.000 | 0.000 | 0.284 | 0.000 | −1.059 | 0.000 | −1.686 | 0.836 | 27.608 | 6.628 |
| 6 | −3.829 | 0.041 | 0.285 | −1.260 | 0.228 | 11.200 | 0.278 | 0.000 | −1.628 | 0.000 | | | | |
| 7 | −4.545 | 0.043 | 0.702 | −2.369 | −4.205 | 43.633 | 0.014 | −0.009 | −0.475 | 0.280 | −26.422 | 15.722 | 18207 | −11788 |
| 8 | −3.925 | 0.042 | 0.723 | −3.670 | 0.247 | 10.822 | 0.016 | −0.010 | −1.964 | 1.288 | | | | |
| 9 Age < 65 | −4.491 | 0.045 | 0.881 | −3.965 | 0.605 | 13.862 | 0.025 | −0.017 | −1.931 | 1.239 | | | | |
| Age ≥ 65 | −6.117 | 0.085 | 0.359 | −2.850 | −0.233 | 7.525 | −0.007 | 0.006 | −1.207 | 0.781 | | | | |

It should be appreciated that the particular coefficients used in an implementation of the techniques described herein may differ from those described in Table 1, as the values in Table 1 are provided merely for illustration. Additionally, in some embodiments, different coefficients may be used for different patient populations and/or to determine probabilities of different outcomes. For example, different coefficients may be used for patients of different age ranges, as described above for the age-stratified cubic spline model. Different coefficients may also be used to Continuing with the process of FIG. 2, after a model has been selected, the process proceeds to act 214, where it is determined whether the selected model is a full model (e.g., includes all four kallikrein markers) or is a partial model that includes less than all markers in a kallikrein panel. If it is determined that the selected model is not a full model, the process proceeds to act 216, where the probability of cancer is determined based solely on the received tPSA value, as described above. If it is determined that the selected model is a full model, the process proceeds to act 218, where the probability of cancer is determined based on the selected model using multiple blood markers. Regardless of the particular model that is selected, after the probability of cancer is determined, the process proceeds to act 220, where the probability of cancer is output, as discussed above in connection with FIG. 1.

In some embodiments of the invention, said event for which said probability is obtained is evidence of prostate cancer at prostate biopsy taken from an asymptomatic male person or a male person with lower urinary tract symptoms.

In some embodiments of the invention, the event for which said probability is obtained is evidence of high grade prostate cancer, i.e. Gleason score 7 or higher, at prostate biopsy taken from an asymptomatic male person or a male person with lower urinary tract symptoms. Typically, the progression of prostate cancer or the prostate cancer status, is defined as (i) Gleason score 7 or higher, (ii) Gleason grade 4+3 or higher, or (iii) Gleason score 8 or higher.

In many preferred embodiments the data of the multitude of male persons comprises one or more biopsy data selected from the group consisting of reason for biopsy, year of biopsy, number of biopsy cores, the number of positive cores, the percent of positive in each core and any possible combination thereof.

As discussed above, in many preferred embodiments, the blood markers are included in a logistic regression model employing up to two non-linear terms for at least one blood marker. In certain embodiments, the blood markers are included in a logistic regression model employing up to three non-linear terms for at least one blood marker. In certain embodiments, the blood markers are included in a logistic regression model employing up to four non-linear terms for at least one blood marker. In certain embodiments, the blood markers are included in a logistic regression model including up to five non-linear terms for at least one blood marker In some embodiments, the logistic regression model may be recalibrated when the anticipated event rate in a target population representative of the male person for which the event probability is to be obtained differs from the event rate of the multitude of male persons for which data have been employed to obtain the logistic regression model by defining, according to equation (II):

$$k = \left( \frac{P/(1-P)}{p/(1-p)} \right), \quad (II)$$

wherein p is the event rate in said data of said multitude of male persons, and P is the anticipated event rate in said target population, defining, according to equation (III):

$$\text{Odds} = \frac{\pi}{1-\pi}, \quad (III)$$

wherein π is the original probability from the model, and defining, according to equation (IV):

$$\text{Odds}_{recalibrated} = \text{Odds} \times k \quad (IV), \text{ and}$$

obtaining a recalibrated probability, according to formula (V):

$$\pi_{recalibrated} = \left( \frac{Odds_{recalibrated}}{1 + Odds_{recalibrated}} \right), \quad (V)$$

wherein $\pi_{recalibrated}$ is the probability of said event.

Some embodiments are directed to methods and apparatus for predicting prostate gland volume using a linear regression model, wherein said method comprises an act of a) providing a linear regression model obtained by employing linear regression of data of a multitude of male persons, said data comprising for each male person of said multitude of male persons: (i) data on prostate gland volume, and (ii) data, preceding data on prostate gland volume, comprising age; and determinations of blood markers including tPSA, fPSA, iPSA, and optionally hK2, from blood samples of said male persons. Said linear regression model may be generated employing formula (VI):

$$V = \sum_{i=1}^{j} \beta_i x_i + c, \quad (VI)$$

wherein V is prostate gland volume, $\beta_i$ is the coefficient for variable $x_i$ for j variables comprising age, tPSA, fPSA, iPSA, and optionally hK2, respectively, to obtain said linear regression model. The method further comprises an act of b) providing the age of a male person in years, c) determining said blood markers tPSA, fPSA, iPSA, and optionally, hK2, respectively, from a blood sample of said male person, and d) employing said linear regression model using said provided age of step b) and said determined blood markers of step c) to obtain said predicted prostate volume of said male person. In some embodiments, the statistical model said risk for cancer is based on tPSA alone if tPSA is ≥15 ng/ml, preferably ≥20 ng/ml, and most preferably ≥25 ng/ml.

It should be appreciated that any suitable logistic regression model including, but not limited to, the models described above for determining a probability of prostate cancer upon biopsy, may be used with embodiments of the invention for determining prostate gland volume.

In some embodiments, the data of step a) (ii) for providing the logistic regression model or the linear regression model, and the determination of blood markers of said male person comprise human kallikrein 2.

In many preferred embodiments of the method of the invention where prostate gland volume is predicted prostate gland volume is provided as defined by transrectal ultrasound.

In many preferred embodiments of the method of the present invention the data for each male person of said multitude of male persons for providing the logistic regression model or linear regression model further includes results of digital rectal examination (DRE) and accordingly DRE is carried out for the male person and obtained result is used when employing the logistic regression model or linear regression model, respectively, to obtain said probability. Preferably the results of DRE are expressed as binary values, i.e. normal=0, and nodularity present=1 with or without a second value for estimate volume, i.e. small=0, medium=1 and large=2.

In some preferred embodiments of the method of the present invention the data of the multitude of male persons for obtaining the model only comprises data of male persons with elevated levels, defined as age-specific median or higher, of tPSA and accordingly probabilities of the event or the predicted prostate volume are obtained only for male persons with said elevated levels of tPSA.

In preferred embodiments of the method of the present invention determinations of blood markers of for each male person of the multitude of male persons for obtaining the model and accordingly those blood markers determined to obtain the probability or predicted prostate gland volume are determined from blood samples of serum or plasma, preferably anti-coagulated, either fresh or frozen. Preferably all samples are of the same kind, i.e. either serum or plasma and either fresh or frozen.

In some preferred embodiments of the method of the present invention the logistic regression model or the linear regression model is provided employing data of a multitude of male persons aged 40 to 75 years; and accordingly the probability of the event or the predicted prostate volume is obtained of a male aged 40 to 75 years.

In some preferred embodiments the method of the present invention the logistic regression model or the linear regression model is provided employing data of a multitude of male persons with a tPSA in blood ≥top age tertile, ≥top age quartile, ≥top age quintile, or ≥top age decile, and accordingly the probability of the event or the predicted prostate volume is obtained of a male person with tPSA in blood ≥top age tertile, ≥top age quartile, ≥top age quintile, or ≥top age decile, respectively. As an example, for a male person of age sixty, the corresponding total PSA values may be: 1.5 ng/ml, for the ≥top age tertile, 1.9 ng/ml, for the ≥top age quartile, 2.1 ng/ml, for the ≥top age quintile, and 3 ng/ml, for the ≥top age decile.

Exemplary Computer System

Figure 3:
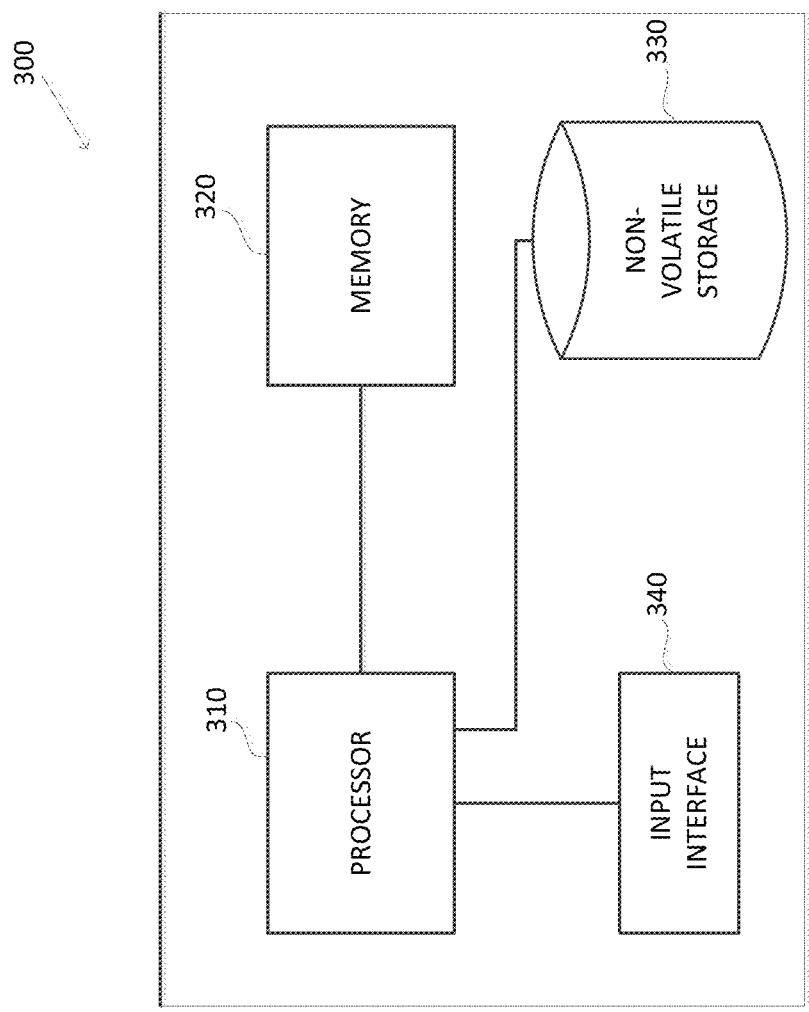
FIG. 3 shows a schematic illustration of a computer system on which some embodiments of the invention may be implemented.

An illustrative implementation of a computer system 300 on which some or all of the techniques and/or user interactions described herein may be implemented is shown in FIG. 3. The computer system 300 may include one or more processors 310 and one or more computer-readable non-transitory storage media (e.g., memory 320 and one or more non-volatile storage media 330). The processor(s) 310 may control writing data to and reading data from the memory 320 and the non-volatile storage device 330 in any suitable manner, as the aspects of the present invention described herein are not limited in this respect.

To perform any of the functionality described herein, the processor(s) 310 may execute one or more instructions, such as program modules, stored in one or more computer-readable storage media (e.g., the memory 320), which may serve as non-transitory computer-readable storage media storing instructions for execution by the processor 310. Generally, program modules include routines, programs, objects, components, data structures, etc. that perform particular tasks or implement particular abstract data types. Embodiments may also be implemented in distributed computing environments where tasks are performed by remote processing devices that are linked through a communications network. In a distributed computing environment, program modules may be located in both local and remote computer storage media including memory storage devices.

Computer 300 may operate in a networked environment using logical connections to one or more remote computers. The one or more remote computers may include a personal computer, a server, a router, a network PC, a peer device or other common network node, and typically include many or all of the elements described above relative to the computer 300. Logical connections between computer 300 and the one or more remote computers may include, but are not limited to, a local area network (LAN) and a wide area network (WAN), but may also include other networks. Such networks may be based on any suitable technology and may operate according to any suitable protocol and may include wireless networks, wired networks or fiber optic networks. Such networking environments are commonplace in offices, enterprise-wide computer networks, intranets and the Internet.

When used in a LAN networking environment, the computer 300 may be connected to the LAN through a network interface or adapter. When used in a WAN networking environment, the computer 300 typically includes a modem or other means for establishing communications over the WAN, such as the Internet. In a networked environment, program modules, or portions thereof, may be stored in the remote memory storage device.

Various inputs described herein for assessing a risk of prostate cancer and/or determining a prostate gland volume may be received by computer 300 via a network (e.g., a LAN, a WAN, or some other network) from one or more remote computers or devices that stores data associated with the inputs. One or more of the remote computers/devices may perform analysis on remotely-stored data prior to sending analysis results as the input data to computer 300. Alternatively, the remotely stored data may be sent to computer 300 as it was stored remotely without any remote analysis. Additionally, inputs may be received directly by a user of computer 300 using any of a number of input interfaces (e.g., input interface 340) that may be incorporated as components of computer 300.

Various outputs described herein, including output of a probability of prostate cancer risk and/or prostate gland volume, may be provided visually on an output device (e.g., a display) connected directly to computer 300 or the output(s) may be provided to a remotely-located output device connected to computer 300 via one or more wired or wireless networks, as embodiments of the invention are not limited in this respect. Outputs described herein may additionally or alternatively be provided other than using visual presentation. For example, computer 300 or a remote computer to which an output is provided may include one or more output interfaces including, but not limited to speakers, and vibratory output interfaces, for providing an indication of the output.

It should be appreciated that although computer 300 is illustrated in FIG. 3 as being a single device, in some embodiments, computer 300 may comprise a plurality of devices communicatively coupled to perform some or all of the functionality described herein, and computer 300 is only one illustrative implementation of a computer that may be used in accordance with embodiments of the invention. For example, in some embodiments, computer 300 may be integrated into and/or in electronic communication with the system shown in FIG. 5.

Figure 4:
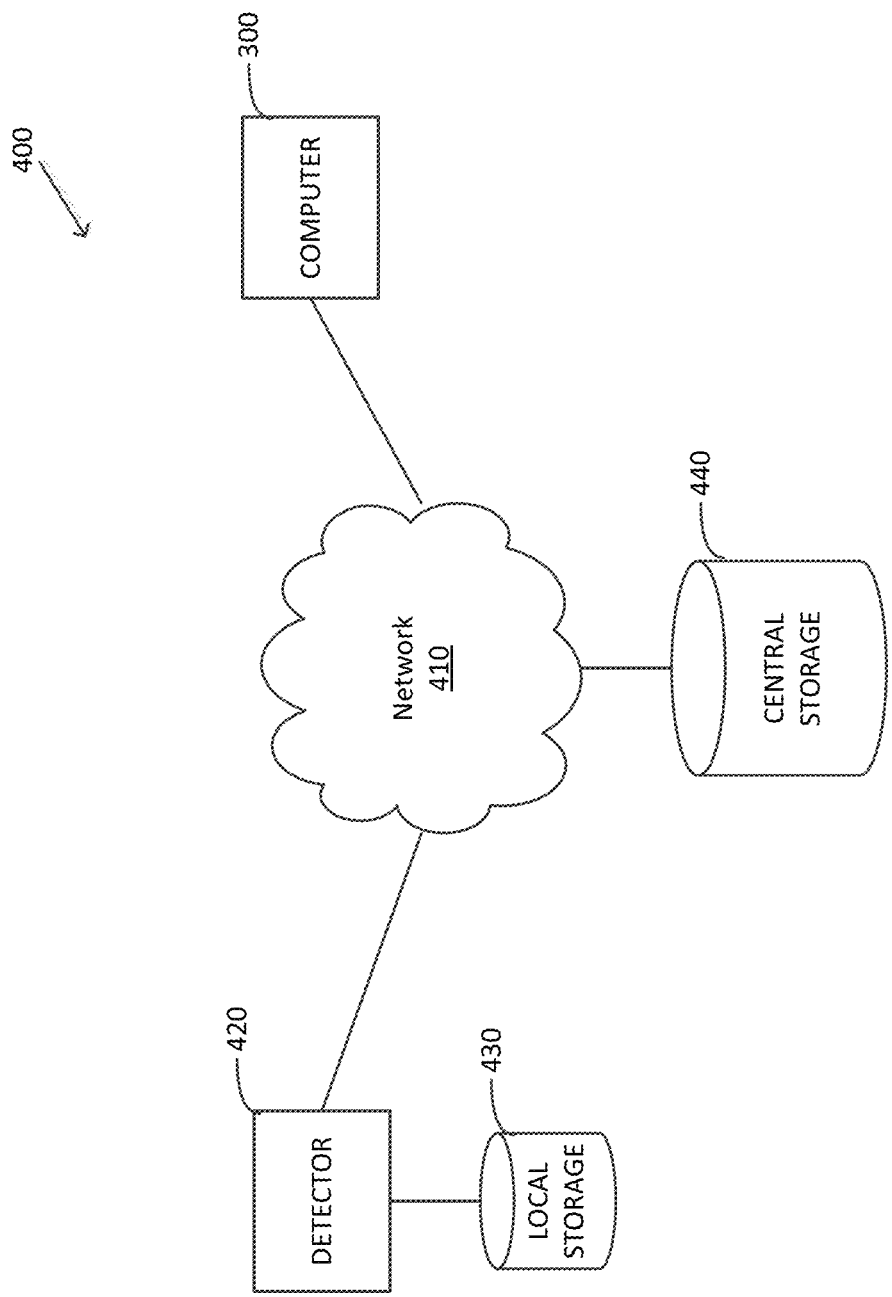
FIG. 4 illustrates an exemplary network environment within which some embodiments of the invention may be used.

As described above, in some embodiments, computer 300 may be included in a networked environment, where information about one or more blood markers, used to determine a probability of prostate cancer and/or prostate gland volume, is sent from an external source to computer 300 for analysis using one or more of the techniques described herein. An illustrative networked environment 400 in accordance with some embodiments of the invention is shown in FIG. 4. In networked environment 400, computer 300 is connected to detector 420 via network 410. As discussed above, network 410 may be any suitable type of wired or wireless network, and may include one or more local area networks (LANs) or wide area networks (WANs), such as the Internet.

Detector 420 may be configured to determine values for one or more of the blood markers used to determine a probability of prostate cancer and/or prostate gland volume, in accordance with one or more of the techniques described herein. Although detector 420 is illustrated in FIG. 4 as a single detector, it should be appreciated that detector 420 may be implemented as multiple detectors, with each detector configured to determine one or more of the blood marker values used in accordance with one or more of the techniques described herein. Additional examples of detectors and detection systems are provided in more detail below (e.g., FIG. 12).

In some embodiments, information corresponding to the values for the blood markers determined from detector 420 may be stored prior to sending the values to computer 300. In such embodiments, the information corresponding to the values may be stored locally in local storage 420 communicatively coupled to detector 420 and/or stored in network-connected central storage 440. Accordingly, when values corresponding to the blood markers are received by computer 300 in accordance with one or more of the techniques described herein, it should be appreciated that at least some of the values may be received directly from detector 420 or from one or more storage devices (e.g., local storage 430, central storage 440) on which the values have been stored, as embodiments are not limited based on where the values are received from.

Other Systems and Components

As described herein, in some embodiments, a system may include a processor or computer programmed to evaluate a logistic regression model in electronic communication with an analyzer for determining a probability of an event associated with prostate cancer (e.g., risk of prostate cancer and/or prostate gland volume). The analyzer may be adapted and arranged to determine one or more characteristics of blood markers for inputting into the logistic regression model. In some embodiments, the analyzer is a microfluidic sample analyzer; for example, the analyzer may be adapted and arranged to determine a sample processed in a microfluidic device/cassette. It should be appreciated, however, that other types of analyzers may also be used (e.g., analyzers for microwell ELISA-type assays) and that the systems described herein are not limited in this respect.

An example of such a system includes, in one set of embodiments, a microfluidic sample analyzer comprising a housing, an opening in the housing configured to receive a cassette having at least one microfluidic channel, wherein the housing includes a component configured to interface with a mating component on the cassette to detect the cassette within the housing. The analyzer may also include a pressure-control system positioned within the housing, the pressure-control system configured to pressurize the at least one microfluidic channel in the cassette to move a sample through the at least one microfluidic channel. An optical system positioned within the housing, the optical system including at least one light source and at least one detector spaced apart from the light source, wherein the light source is configured to pass light through the cassette when the cassette is inserted into the sample analyzer and wherein the detector is positioned opposite the light source to detect the amount of light that passes through the cassette. The system may also include a user interface associated with the housing for inputting at least the age of a person and/or other information for inputting into the linear regression model.

In certain embodiments, a processor is (or is adapted to be) in electronic communication with the microfluidic sample analyzer. In some cases, the processor is within the housing of the analyzer. However, in other embodiments, the processor is not included within the housing of the analyzer but may be accessed by electronic means as described herein. The processor may be programmed to evaluate a logistic regression model based, at least in part, on information received from the at least one detector to determine a probability of an event associated with prostate cancer in a person, wherein evaluating the logistic regression model comprises scaling each of a plurality of variables by a different coefficient value to produce scaled variables and summing values for the scaled variables used to produce the probability of the event associated with prostate cancer in a person, wherein the plurality of variables includes age and at least two variables included in the information received from the detector and is selected from the group consisting of fPSA, iPSA, and tPSA.

A method for determining a probability of an event associated with prostate cancer in a person may include, for example, providing a microfluidic sample analyzer. The microfluidic sample analyzer may comprise a housing, an opening in the housing configured to receive a cassette having at least one microfluidic channel, wherein the housing includes a component configured to interface with a mating component on the cassette to detect the cassette within the housing. The analyzer may further include a pressure-control system positioned within the housing, the pressure-control system configured to pressurize the at least one microfluidic channel in the cassette to move the sample through the at least one microfluidic channel. A optical system positioned within the housing, the optical system including at least one light source and at least one detector spaced apart from the light source, wherein the light source is configured to pass light through the cassette when the cassette is inserted into the sample analyzer and wherein the detector is positioned opposite the light source to detect the amount of light that passes through the cassette. The analyzer may also include a user interface associated with the housing for inputting at least the age of a person. The method may involve determining information for a plurality of blood markers using the microfluidic sample analyzer, wherein the information for the plurality of blood markers includes a fPSA value, iPSA value, tPSA value, and optionally, a hK2 value. The method may also involve evaluating, using at least one processor, a logistic regression model based, at least in part, on the information to determine a probability of an event associated with prostate cancer in a person, wherein evaluating the logistic regression model comprises scaling each of a plurality of variables by a different coefficient value to produce scaled variables and summing values for the scaled variables used to produce the probability of the event associated with prostate cancer in a person, wherein the plurality of variables includes age and at least two variables included in the information received from the detector and is selected from the group consisting of fPSA, iPSA, and tPSA.

Another example of a system includes, in one set of embodiments, a device (e.g., a microfluidic cassette) comprising a first analysis region comprising a first binding partner and a second analysis region comprising a second binding partner. The first binding partner is adapted to bind with at least one of fPSA, iPSA, and tPSA, and the second binding partner is adapted to bind with at least another of fPSA, iPSA, and tPSA. In some embodiments, the device includes a third analysis region including a third binding partner adapted to bind with the third of fPSA, iPSA, and tPSA. Optionally, the device may include a fourth analysis region including a fourth binding partner adapted to bind with hK2. The system includes a detector associated with the first and second analysis regions, and a processor programmed to evaluate a logistic regression model based, at least in part, on information received from the detector to determine a probability of an event associated with prostate cancer in a person. Evaluating the logistic regression model comprises scaling each of a plurality of variables by a different coefficient value to produce scaled variables and summing values for the scaled variables used to produce the probability of the event associated with prostate cancer in a person, wherein the plurality of variables includes age and at least two variables included in the information received from the detector and is selected from the group consisting of fPSA, iPSA, and tPSA.

A method of determining the probability of the event associated with prostate cancer in such a system may include, for example, the acts of introducing a sample into a device (e.g., a microfluidic cassette) comprising a first analysis region comprising a first binding partner and a second analysis region comprising a second binding partner, wherein the first binding partner is adapted to bind with at least one of fPSA, iPSA, and tPSA, and wherein the second binding partner is adapted to bind with at least another of fPSA, iPSA, and tPSA. In some embodiments, the device includes a third analysis region including a third binding partner adapted to bind with the third of fPSA, iPSA, and tPSA. Optionally, the device may include a fourth analysis region including a fourth binding partner adapted to bind with hK2. The method may involve allowing any of the fPSA, iPSA and/or tPSA from the sample to bind with at least the first and/or second binding partners at the first and second analysis regions and determining a characteristic of fPSA, iPSA and/or tPSA using one or more detectors associated with the first and second analysis regions. The method involves inputting the characteristics of fPSA, iPSA and/or tPSA into a processor programmed to evaluate a logistic regression model based, at least in part, on information received from the at least one detector to determine a probability of an event associated with prostate cancer in a person, wherein evaluating the logistic regression model comprises scaling each of a plurality of variables by a different coefficient value to produce scaled variables and summing values for the scaled variables used to produce the probability of the event associated with prostate cancer in a person, wherein the plurality of variables includes age and at least two variables included in the information received from the detector and is selected from the group consisting of fPSA, iPSA, and tPSA. Accordingly, the probability of the event associated with prostate cancer may be determined.

In certain embodiments, a device for determining blood markers (e.g., fPSA, iPSA, tPSA, and/or hK2) is provided. In some cases, the device may allow for simultaneous determination of the blood markers, e.g., on a single cassette. The device may include a microfluidic system comprising a first microfluidic channel including at least one inlet and one outlet, a first reagent stored in the first microfluidic channel, and a seal covering the inlet of the first microfluidic channel and a seal covering the outlet of the first microfluidic channel so as to store the first reagent in the first microfluidic channel. The device may further include a second microfluidic channel including at least one inlet and one outlet, a first analysis region, a second analysis region, and a third analysis region. Each of the analysis regions may include one of an anti-iPSA specific capture antibody, an anti-fPSA specific capture antibody, and an anti-tPSA specific capture antibody (and, optionally, an hK2 specific capture antibody). One or more of the first, second and third analysis regions may be in fluid communication with the second microfluidic channel. The device also includes a fluidic connector that can be connected to the microfluidic system, wherein the fluidic connector comprises a fluid path including a fluid path inlet and a fluid path outlet, wherein upon connection, the fluid path inlet connects to the outlet of the first microfluidic channel to allow fluid communication between the fluid path and the first microfluidic channel, and the fluid path outlet connects to the inlet of the second microfluidic channel to allow fluid communication between the fluid path and the second microfluidic channel. The first and second microfluidic channels are not in fluid communication with one another absent connection via the fluidic connector. The device may optionally include a source of a metal colloid conjugated to an antibody that binds to anti-PSA.

In some embodiments involving a device described herein, at least two (or at least three) of the first, second and third analysis regions is in fluid communication with the second microfluidic channel. In certain cases, each of the first, second and third (and optionally fourth) analysis regions is in fluid communication with the second microfluidic channel. In some instances, the first analysis region is in fluid communication with the second microfluidic channel, and the second analysis region is in fluid communication with a third microfluidic channel. The second and third analysis regions (as well as the second and third microfluidic channels) may, for example, be formed on the same substrate layer, or on different substrate layers as described herein. Additionally, in some embodiments the third analysis region is in fluid communication with a fourth microfluidic channel. The third and fourth analysis regions (as well as the third and fourth microfluidic channels) may, for example, be formed on the same substrate layer, or on different substrate layers as described herein. In some cases, each of the first, second and third (and optionally fourth) analysis regions are formed in different substrate layers. In other embodiments, the fourth analysis region (which may include an anti-hK2 specific capture antibody, for example) is formed in a substrate layer different from a substrate layer including at least one of the first, second and third analysis regions. In some such embodiments, the first, second and third analysis regions are formed in the same substrate layer.

Regardless of whether the analysis regions are formed in different substrate layers or the same substrate layer, in some embodiments, reagents may be stored and sealed in the first, second, and/or third (and optionally fourth) analysis regions, e.g., prior to use of the device. The reagents may include, for example, an anti-iPSA specific capture antibody, an anti-fPSA specific capture antibody, and an anti-tPSA specific capture antibody (and, optionally, an hK2 specific capture antibody). Upon use of the device (e.g., upon connection of a fluidic connector to the microfluidic system) the first microfluidic channel may be placed into fluidic communication with one or more of the first, second, and third (and optionally fourth) analysis regions. For example, the fluidic connector may connect to one or more inlets of the second, third and/or fourth microfluidic channel(s) upon connection to the microfluidic system. Examples of the device configurations are described in more detail below.

In certain devices described herein, analysis involves the use of a detection antibody that recognizes more than one of iPSA, fPSA, tPSA and hK2. For example, a detection antibody may recognize both PSA and hK2, and then a blocker can be used to interfere with PSA such that only hK2 is detected. For instance, in one particular embodiment, an analysis region may include an anti-hK2 capture antibody (which may also capture, e.g., 5-10% tPSA, and which may be stored in the analysis region prior to use as described herein), as well as blocker antibodies that block the tPSA. An anti-hK2 detector antibody (which may also detect tPSA) can be used to detect the amount of binding of hK2. A different analysis region may include, for example, an anti-tPSA capture antibody (which may be stored in an analysis region prior to use as described herein) that captures both fPSA and tPSA. Two different detector antibodies, e.g., an anti-tPSA detector antibody with a fluorescent tag for one wavelength, and an anti-fPSA detector antibody with a fluorescent tag for a different wavelength, may be used for detection. A different analysis region may include, for example, an anti-fPSA capture antibody, and optionally an anti-iPSA capture antibody. Two different detector antibodies, e.g., an anti-fPSA detector antibody with a fluorescent tag for one wavelength, and an anti-iPSA detector antibody with a fluorescent tag for a different wavelength, may be used for detection.

In other embodiments, however, specific capture antibodies may be used for detection of the species. Each of the specific capture antibodies may be positioned in different analysis regions, as described herein. Advantageously, the use of specific capture antibodies and/or the positioning of capture antibodies at different analysis regions may allow for the use of the same detection antibody for detection of each of the species. In some such embodiments, the same wavelength may be used to determine each of the species. This may allow for the use of simplified detectors and/or optical components for detection. For example, in some embodiments, detection involves accumulation of an opaque material at different analysis regions that can be determined at a particular wavelength, as described in more detail below.

For example, in one set of embodiments an anti-iPSA specific capture antibody, an anti-fPSA specific capture antibody, and an anti-tPSA specific capture antibody (and, optionally, an hK2 specific capture antibody) may be included in different analysis regions as described herein, optionally along with negative and positive controls. A detection antibody such as a gold labeled antibody which is anti-PSA and anti-hK2 may be used to detect each of iPSA, fPSA, tPSA and/or hK2. In other embodiments, however, a mixture of gold labeled antibodies, such as a gold labeled anti-hK2 antibody, gold labeled anti-PSA antibody, and/or gold labeled anti-iPSA antibody may be used for detection. In such a system, the same wavelength may be used to determine each of the species and this may allow for the use of simplified detectors and/or optical components for detection.

Examples of specific systems, devices and analyzers that can be used in combination with embodiments provided herein are now described.

Figure 5:
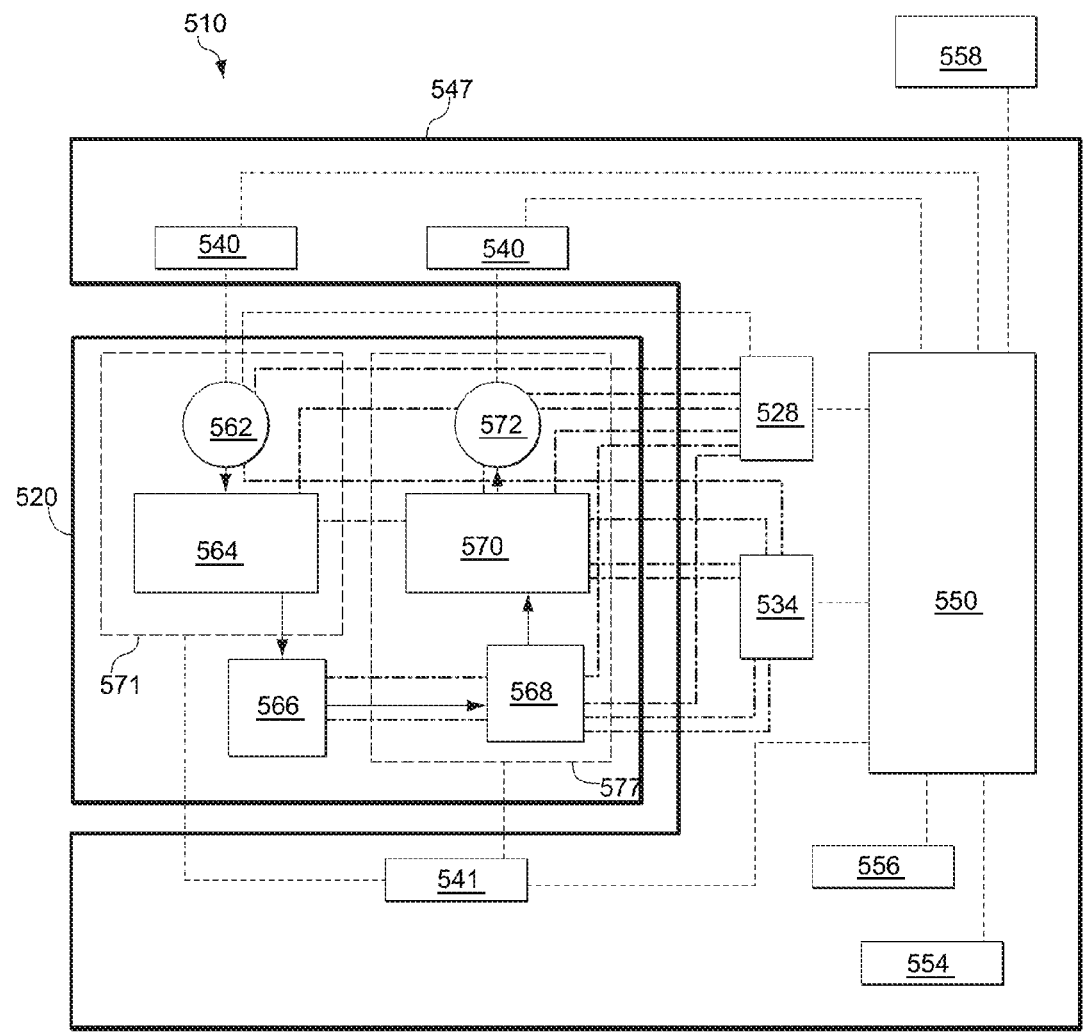
FIG. 5 is a block diagram showing a microfluidic system and a variety of components that may be part of a sample analyzer that can be used to determine one or more blood markers in accordance with some embodiments of the invention.

FIG. 5 shows a block diagram 510 of a microfluidic system and various components that may be included according to one set of embodiments. The microfluidic system may include, for example, a cassette 520 operatively associated with one or more components such as a fluid flow source 540 such as a pump (e.g., for introducing one or more fluids into the cassette and/or for controlling the rates of fluid flow), optionally a fluid flow source 540 such as a pump or vacuum that may be configured to apply either of both of a positive pressure or vacuum (e.g., for moving/removing one or more fluids within/from the cassette and/or for controlling the rates of fluid flow), a valving system 528 (e.g., for actuating one or more valves), a detection system 534 (e.g., for detecting one or more fluids and/or processes), and/or a temperature regulating system 541 (e.g., to heat and/or cool one or more regions of the cassette). The components may be external or internal to the microfluidic device, and may optionally include one or more processors for controlling the component or system of components. In certain embodiments, one or more such components and/or processors are associated with a sample analyzer 547 configured to process and/or analyze a sample contained in the cassette. The processor may optionally be programmed to evaluate a linear regression model as described herein.

In general, as used herein, a component that is "operatively associated with" one or more other components indicates that such components are directly connected to each other, in direct physical contact with each other without being connected or attached to each other, or are not directly connected to each other or in contact with each other, but are mechanically, electrically (including via electromagnetic signals transmitted through space), or fluidically interconnected (e.g., via channels such as tubing) so as to cause or enable the components so associated to perform their intended functionality.

The components shown illustratively in FIG. 5, as well as other optional components such as those described herein, may be operatively associated with a control system 550. In some embodiments, the control system may be used to control fluids and/or conduct quality control by the use of feedback from one or more events taking place in the microfluidic system. For instance, the control system may be configured to receive input signals from the one or more components, to calculate and/or control various parameters, to compare one or more signals or a pattern of signals with signals preprogrammed into the control system, and/or to send signals to one or more components to modulate fluid flow and/or control operation of the microfluidic system. The control system may also be optionally associated with other components such as a user interface 554, an identification system 556, an external communication unit 558 (e.g., a USB), and/or other components, as described in more detail below.

Cassette (e.g., microfluidic device) 520 may have any suitable configuration of channels and/or components for performing a desired analysis. In one set of embodiments, cassette 520 contains stored reagents that can be used for performing a chemical and/or biological reaction (e.g., an immunoassay), e.g., as described in more detail herein. The cassette may include, for example, an optional reagent inlet 562 in fluid communication with an optional reagent storage area 564. The storage area may include, for example, one or more channels and/or reservoirs that may, in some embodiments, be partially or completely filled with fluids (e.g., liquids and gases, including immiscible reagents such as reagent solutions and wash solutions, optionally separated by immiscible fluids, as described in more detail herein). The cassette may also include an optional sample or reagent loading area 566, such as a fluidic connector that can be used to connect reagent storage area 564 to an optional analysis region 568. The analysis region, which may include one or more areas for detecting a component in a sample (e.g., analysis regions), may be in fluid communication with an optional waste area 570 and coupled to outlet 572. In some cases, such and other device features may be formed on or in different components or layers of a cassette, as described in more detail herein. Thus, it should be appreciated that a cassette may include a single component, or multiple components that are attached during use, such as a combination of an article with attached fluidic connector as described herein. In one set of embodiments, fluid may flow in the direction of the arrows shown in the figure. Further description and examples of such and other components are provided herein.

In some embodiments, sections 571 and 577 of the cassette are not in fluid communication with one another prior to introduction of a sample into the cassette. In some cases, sections 571 and 577 are not in fluid communication with one another prior to first use of the cassette, wherein at first use, the sections are brought into fluid communication with one another. In other embodiments, however, sections 571 and 577 are in fluid communication with one another prior to first use and/or prior to introduction of a sample into the cassette. Other configurations of cassettes are also possible.

As shown in the exemplary embodiment illustrated in FIG. 5, one or more fluid flow sources 540 such as a pump and/or a vacuum or other pressure-control system, valving system 528, detection system 534, temperature regulating system 541, and/or other components may be operatively associated with one or more of reagent inlet 562, reagent storage area 564, sample or reagent loading area 566, reaction area 568, waste area 570, outlet 572, and/or other regions of cassette 520. Detection of processes or events in one or more regions of the cassette can produce a signal or pattern of signals that can be transmitted to control system 550. Based on the signal(s) received by the control system, this feedback can be used to manipulate fluids within and/or between each of these regions of the microfluidic device, such as by controlling one or more of a pump, vacuum, valving system, detection system, temperature regulating system, and/or other components.

Figure 6:
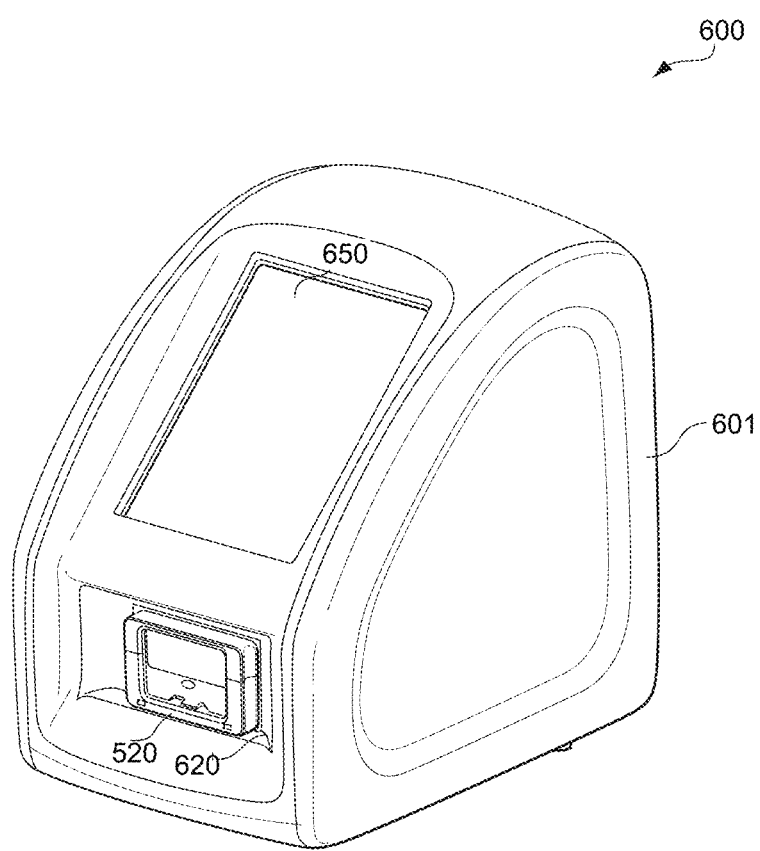
FIG. 6 is a perspective view of a sample analyzer and cassette that can be used to determine one or more blood markers in accordance with some embodiments of the invention.
Figure 7:
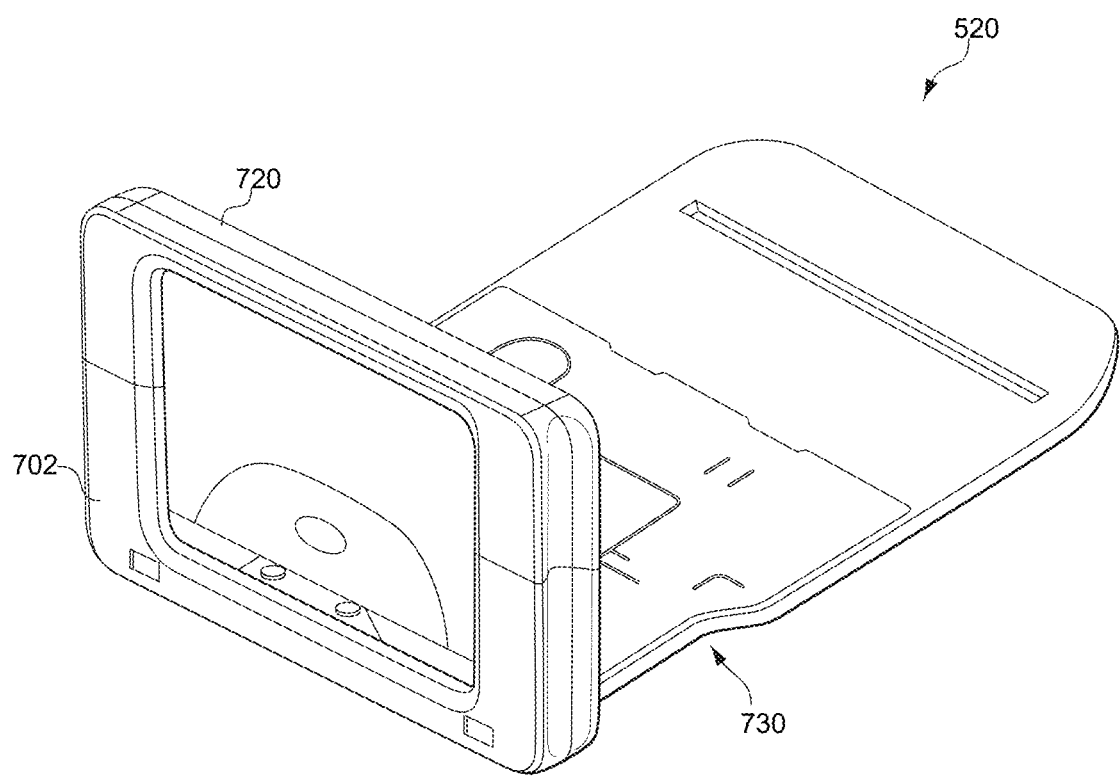
FIG. 7 is a perspective view of a cassette including a fluidic connector that can be used to determine one or more blood markers in accordance with some embodiments of the invention.

Turning to FIG. 6, one embodiment of a microfluidic sample analyzer 600 is illustrated. As shown in the exemplary embodiment of FIG. 6, the analyzer includes a housing 601 which is configured to cover or retain the components of the analyzer which are discussed in greater detail below. An opening 620 in the housing is configured to receive a cassette 520. As set forth in greater detail below, the analyzer 600 may also include a user interface 650 positioned within the housing which is configured for a user to input information into the sample analyzer. In this particular embodiment, the user interface 650 includes a touch screen, but as discussed below, the user interface may be configured differently.

In some embodiments, the analyzer may include a fluid flow source (e.g., a vacuum system) configured to pressurize the cassette, an identification reader configured to read information associated with the cassette, and a mechanical subsystem which includes a component configured to interface with the cassette to detect the cassette within the housing. As mentioned above, an opening in the housing is configured to receive a cassette. The opening 620 may be configured as an elongated slot. The opening may be configured in this manner to receive a substantially card-shaped cassette. It should be appreciated that in other embodiments, the opening may be shaped and configured differently as the invention is not so limited.

As mentioned above, the microfluidic sample analyzer 600 may be configured to receive a variety of types of cassettes 520 (e.g., microfluidic devices). FIGS. 7-11F illustrate various exemplary embodiments of the cassette 520 for use with analyzer 600. As shown, the cassette may be substantially card-shaped (i.e., similar to a card key) having a substantially rigid plate-like structure.

The cassette 520 may be configured to include a fluidic connector 720, which may snap into one end of the cassette. In certain embodiments, the fluidic connector can be used to introduce one or more fluids (e.g., a sample or a reagent) into the cassette.

In one set of embodiments, the fluidic connector is used to fluidly connect two (or more) channels of the cassette during first use, which channels are not connected prior to first use. For example, the cassette may include two channels that are not in fluid communication prior to first use of the cassette. Non-connected channels may be advantageous in certain cases, such as for storing different reagents in each of the channels. For example, a first channel may be used to store dry reagents and a second channel may be used to store wet reagents. Having the channels be physically separated from one another can enhance long-term stability of the reagents stored in each of the channels, e.g., by keeping the reagent(s) stored in dry form protected from moisture that may be produced by reagent(s) stored in wet form. At first use, the channels may be connected via the fluidic connector to allow fluid communication between the channels of the cassette. For instance, the fluidic connected may puncture seals covering inlets and/or outlets of the cassette to allow insertion of the fluidic connector into the cassette.

As used herein, "prior to first use of the cassette" means a time or times before the cassette is first used by an intended user after commercial sale. First use may include any step(s) requiring manipulation of the device by a user. For example, first use may involve one or more steps such as puncturing a sealed inlet to introduce a reagent into the cassette, connecting two or more channels to cause fluid communication between the channels, preparation of the device (e.g., loading of reagents into the device) before analysis of a sample, loading of a sample onto the device, preparation of a sample in a region of the device, performing a reaction with a sample, detection of a sample, etc. First use, in this context, does not include manufacture or other preparatory or quality control steps taken by the manufacturer of the cassette. Those of ordinary skill in the art are well aware of the meaning of first use in this context, and will be able easily to determine whether a cassette of the invention has or has not experienced first use. In one set of embodiments, cassette of the invention are disposable after first use (e.g., after completion of an assay), and it is particularly evident when such devices are first used, because it is typically impractical to use the devices at all (e.g., for performing a second assay) after first use.

Figure 8:
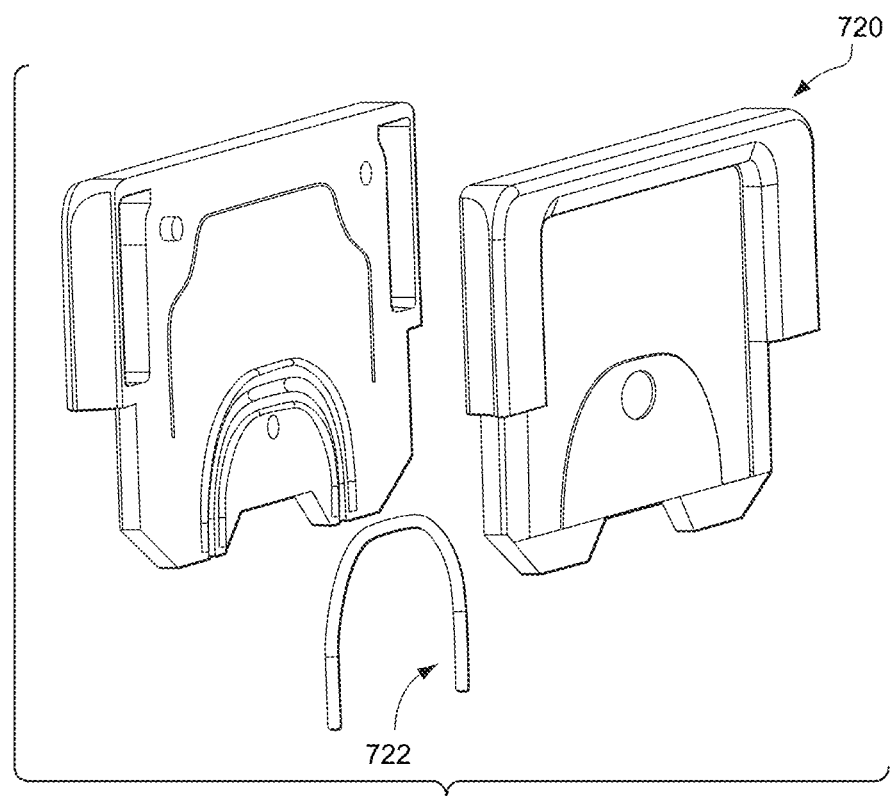
FIG. 8 is an exploded assembly view of a fluidic connector that can be used to determine one or more blood markers in accordance with some embodiments of the invention.
Figure 9:
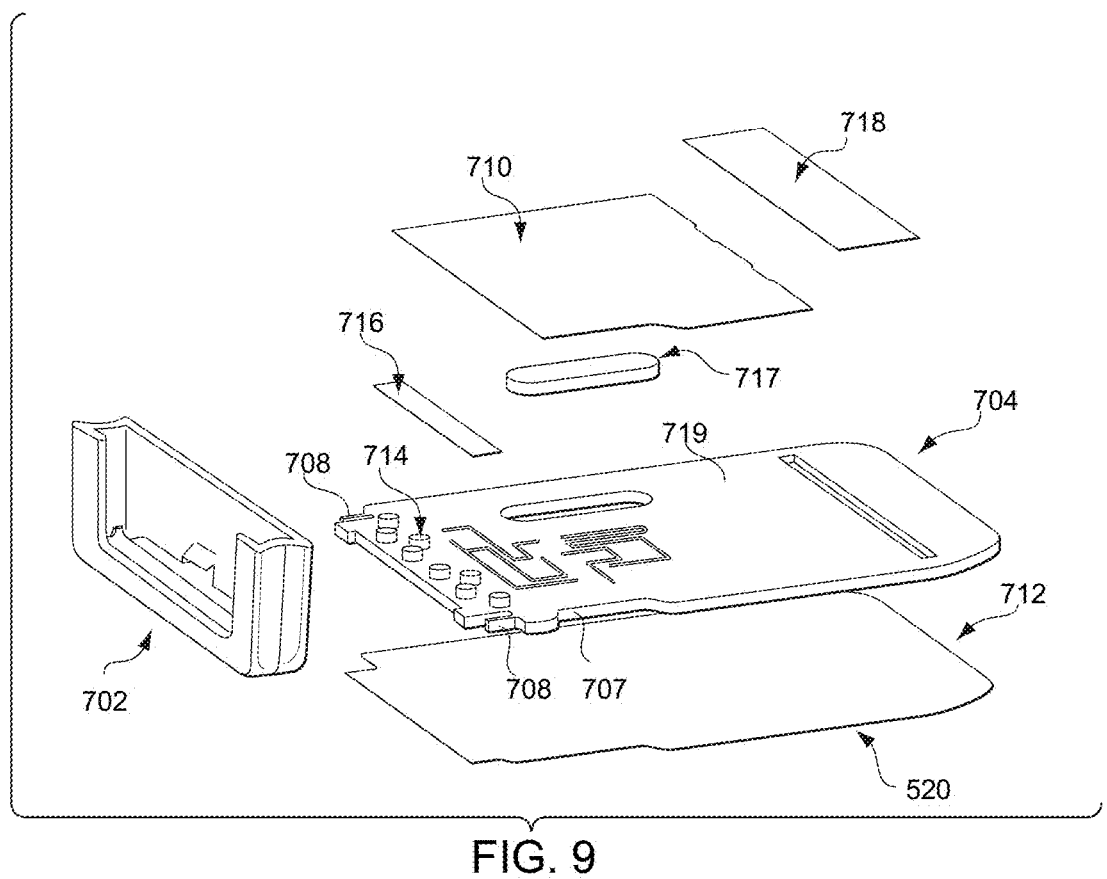
FIG. 9 is a an exploded assembly view of a cassette that can be used to determine one or more blood markers in accordance with some embodiments of the invention.

As shown in exemplary embodiment illustrated in FIG. 8, the fluidic connector 720 may include a substantially U-shaped channel 722, or channel having any other suitable shape, which may hold a fluid and/or reagent (e.g., a fluid sample and/or one or more detection antibodies) prior to be connected to the cassette. Channel 722 may be housed between two shell components which form the connector 720. In some embodiments, the fluidic connector may be used to collect a sample from the patient prior to the fluidic connector being connected to the cassette. For example, a lancet or other suitable instrument can be used to obtain a finger-stick blood sample which may then be collected by the fluidic connector 720 and loaded into channel 722 by capillary action. In other embodiments, the fluidic connector 720 may be configured to puncture a patient's finger to collect the sample in the channel 722. In certain embodiments, fluid connector 720 does not contain a sample (or reagent) prior to connection to the cassette, but simply allows fluid communication between two or more channels of the cassette upon connection. In one embodiment, the U-shaped channel is formed with a capillary tube. The fluidic connector can also include other channel configurations, and in some embodiments, may include more than one channels that may be fluidically connected or unconnected to one another.

FIGS. 9-11F illustrate various exemplary embodiments of the cassette 520 in greater detail. As shown illustratively in the exploded assembly view of FIG. 9, the cassette 520 may include a cassette body 704 which includes at least one channel 706 configured to receive a sample or reagent and through which a sample or reagent may flow. The cassette body 704 may also include latches 708 positioned on one end that interlock with the fluidic connector alignment element 702 for a snap fit.

The cassette 520 may also include top and bottom covers 710 and 712, which may, for example, be made of a transparent material. In some embodiments, a cover can be in the form of a biocompatible adhesive and can be made of a polymer (e.g., polyethylene (PE), a cyclic olefin copolymer (COC), polyvinyl chloride (PVC)) or an inorganic material for example. In some cases, one or more covers are in the form of an adhesive film (e.g., a tape). For some applications, the material and dimensions of a cover are chosen such that the cover is substantially impermeable to water vapor. In other embodiments, the cover can be non-adhesive, but may bond thermally to the microfluidic substrate by direct application of heat, laser energy, or ultrasonic energy. Any inlet(s) and/or outlet(s) of a channel of the cassette can be sealed (e.g., by placing an adhesive over the inlet(s) and/or outlet(s)) using one or more covers. In some cases, the cover substantially seals one or more stored reagents in the cassette.

As illustrated, the cassette body 704 may include one or more ports 714 coupled to the channel 706 in the cassette body 704. These ports 714 can be configured to align with the substantially U-shaped channel 722 in the fluidic connector 720 when the fluidic connector 720 is coupled to the cassette 520 to fluidly connect the channel 706 in the cassette body 704 with the channel 722 in the fluidic connector 720. In certain embodiments, substantially U-shaped channel 722 can also be fluidically connected to channel 707, thereby coupling channels 706 and 707. As shown, a cover 716 may be provided over the ports 714 and the cover 716 may be configured to be pieced or otherwise opened (e.g., by the connector 720 or by other means) to fluidly connect the two channels 706 and 722. Additionally, a cover 718 may be provided to cover port 719 (e.g., a vacuum port) in the cassette body 704. As set forth in further detail below, the port 719 may be configured to fluidly connect a fluid flow source 540 with the channel 706 to move a sample through the cassette. The cover 718 over the port 719 may be configured to be pierced or otherwise opened to fluidly connect the channel 706 with the fluid flow source 540.

The cassette body 704 may optionally include a liquid containment region such as a waste area, including an absorbent material 717 (e.g., a waste pad). In some embodiments, the liquid containment region includes regions that capture one or more liquids flowing in the cassette, while allowing gases or other fluids in the cassette to pass through the region. This may be achieved, in some embodiments, by positioning one or more absorbent materials in the liquid containment region for absorbing the liquids. This configuration may be useful for removing air bubbles from a stream of fluid and/or for separating hydrophobic liquids from hydrophilic liquids. In certain embodiments, the liquid containment region prevents liquids from passing through the region. In some such cases, the liquid containment region may act as a waste area by capturing substantially all of the liquid in the cassette, thereby preventing liquid from exiting the cassette (e.g., while allowing gases to escape from an outlet of the cassette). For example, the waste area may be used to store the sample and/or reagents in the cassette after they have passed through the channel 706 during the analysis of the sample. These and other arrangements may be useful when the cassette is used as a diagnostic tool, as the liquid containment region may prevent a user from being exposed to potentially-harmful fluids in the cassette.

Figure 10:
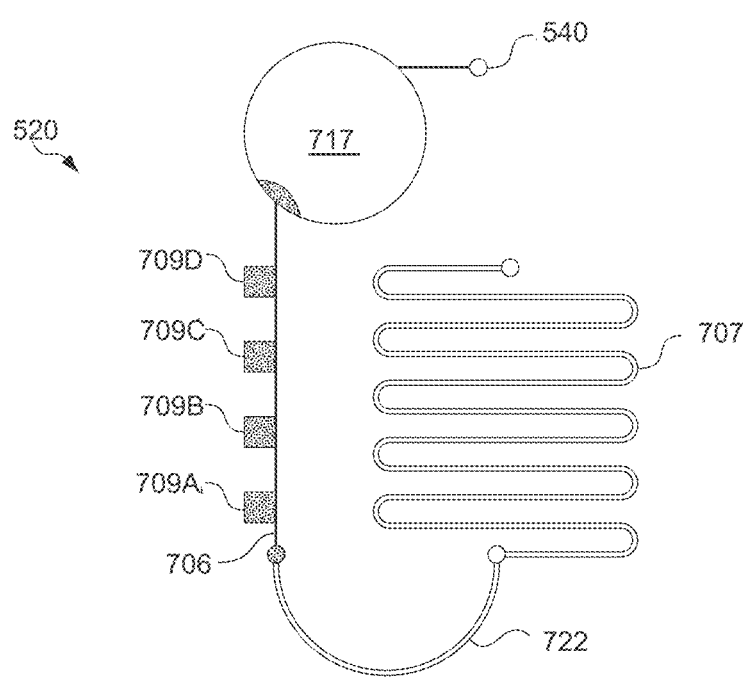
FIG. 10 is a schematic view of a cassette including a fluidic connector that can be used to determine one or more blood markers in accordance with some embodiments of the invention.

The schematic view of the cassette 520 illustrated in FIG. 10 shows one embodiment where the cassette 520 includes a first channel 706 and a second channel 707 spaced apart from the first channel 706. In one embodiment, the channels 706, 707 range in largest cross-section dimension from approximately 50 micrometers to approximately 500 micrometers, although other channel sizes and configurations may be used, as described in more detail below.

The first channel 706 may include one or more analysis regions 709 used to analyze the sample. For example, in one illustrative embodiment, the channel 706 includes four analysis regions 709 (e.g., connected in series or in parallel) which are utilized during sample analysis. As described herein, each of the analysis regions may be adapted to detect one or more of iPSA, fPSA, tPSA and/or hK2.

In certain embodiments, one or more analysis regions are in the form of meandering regions (e.g., regions involving meandering channels). A meandering region may, for example, be defined by an area of at least 0.25 mm$^2$, at least 0.5 mm$^2$, at least 0.75 mm$^2$, or at least 1.0 mm$^2$, wherein at least 25%, 50%, or 75% of the area of the meandering region comprises an optical detection pathway. A detector that allows measurement of a single signal through more than one adjacent segments of the meandering region may be positioned adjacent the meandering region. In some cases, channel 706 is fluidically connected to at least two meandering regions connected in series.

As described herein, the first channel 706 and/or the second channel 707 may be used to store one or more reagents (e.g., capture antibodies for iPSA, fPSA, tPSA and/or hK2) used to process and analyze the sample prior to first use of the cassette. In some embodiments, dry reagents are stored in one channel or section of a cassette and wet reagents are stored in a second channel or section of cassette. Alternatively, two separate sections or channels of a cassette may both contain dry reagents and/or wet reagents. Reagents can be stored and/or disposed, for example, as a liquid, a gas, a gel, a plurality of particles, or a film. The reagents may be positioned in any suitable portion of a cassette, including, but not limited to, in a channel, reservoir, on a surface, and in or on a membrane, which may optionally be part of a reagent storage area. A reagent may be associated with a cassette (or components of a cassette) in any suitable manner. For example, reagents may be crosslinked (e.g., covalently or ionically), absorbed, or adsorbed (physisorbed) onto a surface within the cassette. In one particular embodiment, all or a portion of a channel (such as a fluid path of a fluid connector or a channel of the cassette) is coated with an anti-coagulant (e.g., heparin). In some cases, a liquid is contained within a channel or reservoir of a cassette prior to first use and/or prior to introduction of a sample into the cassette.

In some embodiments, the stored reagents may include fluid plugs positioned in linear order so that during use, as fluids flow to an analysis region, they are delivered in a predetermined sequence. A cassette designed to perform an assay, for example, may include, in series, a rinse fluid, a labeled-antibody fluid, a rinse fluid, and a amplification fluid, all stored therein. While the fluids are stored, they may be kept separated by substantially immiscible separation fluids (e.g., a gas such as air) so that fluid reagents that would normally react with each other when in contact may be stored in a common channel.

Reagents can be stored in a cassette for various amounts of time. For example, a reagent may be stored for longer than 1 hour, longer than 6 hours, longer than 12 hours, longer than 1 day, longer than 1 week, longer than 1 month, longer than 3 months, longer than 6 months, longer than 1 year, or longer than 2 years. Optionally, the cassette may be treated in a suitable manner in order to prolong storage. For instance, cassettes having stored reagents contained therein may be vacuum sealed, stored in a dark environment, and/or stored at low temperatures (e.g., below 0 degrees C.). The length of storage depends on one or more factors such as the particular reagents used, the form of the stored reagents (e.g., wet or dry), the dimensions and materials used to form the substrate and cover layer(s), the method of adhering the substrate and cover layer(s), and how the cassette is treated or stored as a whole. Storing of a reagent (e.g., a liquid or dry reagent) in a channel may involve sealing the inlet(s) and outlet(s) of the channel prior to first use or during packaging of the device.

As illustrated in the exemplary embodiment shown in FIGS. 10 and 11A-11F, channels 706 and 707 may not be in fluid communication with each other until the fluidic connector 720 is coupled to the cassette 520. In other words, the two channels, in some embodiments, are not in fluid communication with one another prior to first use and/or prior to introduction of a sample into the cassette. In particular, as illustrated, the substantially U-shaped channel 722 of the connector 720 may fluidly connect the first and second channels 706, 707 such that the reagents in the second channel 707 can pass through the U-shaped channel 522 and selectively move into the analysis regions 709 in the first channel 706. In other embodiments, the two channels 706 and 707 are in fluid communication with one another prior to first use, and/or prior to introduction of a sample into the cassette, but the fluidic connector further connects the two channels (e.g., to form a closed-loop system) upon first use.

In some embodiments, a cassette described herein may include one more microfluidic channels, although such cassettes are not limited to microfluidic systems and may relate to other types of fluidic systems. A cassette, device, apparatus or system that is microfluidic may include, for example, at least one fluid channel having a maximum cross-sectional dimension of less than 1 mm, and a ratio of length to largest cross-sectional dimension of at least 3:1.

The cross-sectional dimension (e.g., a diameter) of the channel is measured perpendicular to the direction of fluid flow. Most fluid channels in components of cassettes described herein have maximum cross-sectional dimensions less than 2 mm, and in some cases, less than 1 mm. In one set of embodiments, all fluid channels of a cassette are microfluidic or have a largest cross sectional dimension of no more than 2 mm or 1 mm. In another set of embodiments, the maximum cross-sectional dimension of the channel(s) are less than 500 microns, less than 200 microns, less than 100 microns, less than 50 microns, or less than 25 microns. In some cases the dimensions of the channel may be chosen such that fluid is able to freely flow through the article or substrate. The dimensions of the channel may also be chosen, for example, to allow a certain volumetric or linear flowrate of fluid in the channel. Of course, the number of channels and the shape of the channels can be varied by any suitable method known to those of ordinary skill in the art. In some cases, more than one channel or capillary may be used.

A channel may include a feature on or in an article (e.g., a cassette) that at least partially directs the flow of a fluid. The channel can have any suitable cross-sectional shape (circular, oval, triangular, irregular, square or rectangular, or the like) and can be covered or uncovered. In embodiments where it is completely covered, at least one portion of the channel can have a cross-section that is completely enclosed, or the entire channel may be completely enclosed along its entire length with the exception of its inlet(s) and outlet(s). A channel may also have an aspect ratio (length to average cross sectional dimension) of at least 2:1, more typically at least 3:1, 5:1, or 10:1 or more.

Cassettes described herein may include channels or channel segments positioned on one or two sides of the cassette (or a substrate layer of the cassette). In some cases, the channels are formed in a surface of the cassette. The channel segments may be connected by an intervening channel passing through the cassette. In some embodiments, the channel segments are used to store reagents in the device prior to first use by an end user. The specific geometry of the channel segments and the positions of the channel segments within the cassettes may allow fluid reagents to be stored for extended periods of time without mixing, even during routine handling of the cassettes such as during shipping of the cassettes, and when the cassettes are subjected to physical shock or vibration.

In certain embodiments, a cassette includes optical elements that are fabricated on one side of a cassette opposite a series of fluidic channels. An "optical element" is used to refer to a feature formed or positioned on or in an article or cassette that is provided for and used to change the direction (e.g., via refraction or reflection), focus, polarization, and/or other property of incident electromagnetic radiation relative to the light incident upon the article or cassette in the absence of the element. For example, an optical element may comprise a lens (e.g., concave or convex), mirror, grating, groove, or other feature formed or positioned in or on a cassette. A cassette itself absent a unique feature, however, would not constitute an optical element, even though one or more properties of incident light may change upon interaction with the cassette. The optical elements may guide incident light passing through the cassette such that most of the light is dispersed away from specific areas of the cassette, such as intervening portions between the fluidic channels. By decreasing the amount of light incident upon these intervening portions, the amount of noise in a detection signal can be decreased when using certain optical detection systems. In some embodiments, the optical elements comprise triangular grooves formed on or in a surface of the cassette. The draft angle of the triangular grooves may be chosen such that incident light normal to the surface of the cassette is redirected at an angle dependent upon the indices of refraction of the external medium (e.g., air) and the cassette material. In some embodiments, one or more optical elements are positioned between adjacent segments of a meandering region of an analysis region.

A cassette, or portions thereof, can be fabricated of any material suitable for forming a channel or other component. Non-limiting examples of materials include polymers (e.g., polyethylene, polystyrene, polymethylmethacrylate, polycarbonate, poly(dimethylsiloxane), PVC, PTFE, PET, and a cyclo-olefin copolymer), glass, quartz, and silicon. The material forming the cassette and any associated components (e.g., a cover) may be hard or flexible. Those of ordinary skill in the art can readily select suitable material(s) based upon e.g., its rigidity, its inertness to (e.g., freedom from degradation by) a fluid to be passed through it, its robustness at a temperature at which a particular device is to be used, its transparency/opacity to light (e.g., in the ultraviolet and visible regions), and/or the method used to fabricate features in the material. For instance, for injection molded or other extruded articles, the material used may include a thermoplastic (e.g., polypropylene, polycarbonate, acrylonitrile-butadiene-styrene, nylon 6), an elastomer (e.g., polyisoprene, isobutene-isoprene, nitrile, neoprene, ethylene-propylene, hypalon, silicone), a thermoset (e.g., epoxy, unsaturated polyesters, phenolics), or combinations thereof. As described in more detail below, cassettes including two or more components or layers may be formed in different materials to tailor the components to the major function(s) of the each of the components, e.g., based upon those factors described above and herein.

In some embodiments, the material and dimensions (e.g., thickness) of a cassette and/or cover are chosen such that it is substantially impermeable to water vapor. For instance, a cassette designed to store one or more fluids therein prior to first use may include a cover comprising a material known to provide a high vapor barrier, such as metal foil, certain polymers, certain ceramics and combinations thereof. Examples of materials having low water vapor permeability are provided below. In other cases, the material is chosen based at least in part on the shape and/or configuration of the cassette. For instance, certain materials can be used to form planar devices whereas other materials are more suitable for forming devices that are curved or irregularly shaped.

In some instances, a cassette is comprised of a combination of two or more materials, such as the ones listed above. For instance, channels of the cassette may be formed in polystyrene or other polymers (e.g., by injection molding) and a biocompatible tape may be used to seal the channels. The biocompatible tape or flexible material may include a material known to improve vapor barrier properties (e.g., metal foil, polymers or other materials known to have high vapor barriers), and may optionally allow access to inlets and outlets by puncturing or unpeeling the tape. A variety of methods can be used to seal a microfluidic channel or portions of a channel, or to join multiple layers of a device, including but not limited to, the use of adhesives, use adhesive tapes, gluing, bonding, lamination of materials, or by mechanical methods (e.g., clamping, snapping mechanisms, etc.).

In some instances, a cassette comprises a combination of two or more separate components (e.g., layers or cassettes) mounted together. Independent channel networks (such as sections 571 and 577 of FIG. 5), which may optionally include reagents stored therein prior to first use, may be included on or in the different components of the cassette. The separate components may be mounted together or otherwise associated with one another by any suitable means, such as by the methods described herein, e.g., to form a single (composite) cassette. In some embodiments, two or more channel networks are positioned in different components or layers of the cassette and are not connected fluidically prior to first use, but are connected fluidically at first use, e.g., by use of a fluidic connector. In other embodiments, the two or more channel networks are connected fluidically prior to first use.

Advantageously, each of the different components or layers that form a composite cassette may be tailored individually depending on the designed function(s) of that component or layer. For example, in one set of embodiments, one component of a composite cassette may be tailored for storing wet reagents. In some such embodiments, that component may be formed in a material having a relatively low vapor permeability. Additionally or alternatively, e.g., depending on the amount of fluids to be stored, the storage region(s) of that cassette may be made with larger cross-sectional dimensions than channels or regions of other components not used for storage of liquids. The material used to form the cassette may be compatible with fabrication techniques suitable for forming larger cross-sectional dimensions. By contrast, a second component that may be tailored for detection of an analyte may, in some embodiments, include channel portions having smaller cross-sectional dimensions. Smaller cross-sectional dimensions may be useful, for example, in certain embodiments to allow more contact time between fluids flowing in the channel (e.g., a reagent solution or a wash fluid) and an analyte bound to a surface of the channel, for a given volume of fluid. Additionally or alternatively, a channel portion of the second component may have a lower surface roughness (e.g., to increase the signal to noise ratio during detection) compared to a channel portion of another component. The smaller-cross sectional dimensions or lower surface roughness of the channel portions of the second component may, in certain embodiments, require a certain fabrication technique or fabrication tool different from that used to form a different component of the cassette. Furthermore, in some particular embodiments, the material used for the second component may be well characterized for protein attachment and detection. As such, it may be advantageous to form different channels portions used for different purposes on different components of a cassette, which can then be joined together prior to use by an intended user. Other advantages, features of components, and examples are provided below.

FIGS. 11B-11E show a device that may include multiple components or layers 520B and 520C that are combined to form a single cassette. As shown in these illustrative embodiments, component 520B may include a first side 521A and a second side 521B. Component 520C may include a first side 522A and a second side 522B. Device components or parts described herein such as channels or other entities may be formed at, on, or in the first side of a component, a second side of a component and/or through the component in some embodiments. For example, as shown illustratively in FIG. 11C, component 520C may include a channel 706 having an inlet and an outlet, and may be formed in a first material. Channel 706 may have any suitable configuration as described herein and may include, for example, one or more reagent storage regions, analysis regions, liquid containment regions, mixing regions, and the like. In some embodiments, channel 706 is not formed through the entire thickness of component 520B. That is, the channel may be formed at or in one side of the component. Channel 706 may be optionally enclosed by a cover as described herein such as a tape (not shown), another component or layer of the cassette, or other suitable component. In other embodiments, channel 706 is formed through the entire thickness of component 520B and covers are required on both sides of the cassette to enclose the channel. As described herein, different layers or components may include different analysis regions for determining species within a sample. For instance, capture antibodies for iPSA, fPSA, tPSA and/or hK2 may be positioned in different analysis regions, optionally in different components or layers of a cassette such as the one shown.

Component 520B may include channel 707 having an inlet and an outlet, and may be formed in a second material, which may be the same or different as the first material. Channel 707 may also have any suitable configuration as described herein, and may or may not be formed through the entire thickness of component 520C. Channel 707 may be enclosed by one or more covers. In some cases, the cover is not a component that includes one or more fluidic channels such as component 520C. For example, the cover may be a biocompatible tape or other surface positioned between components 520B and 520C. In other embodiments, channel 707 may be substantially enclosed by component 520C. That is, surface 522A of component 520C may form a portion of channel 707 as components 520B and 520C lay directly adjacent to one another.

Figure 11A:
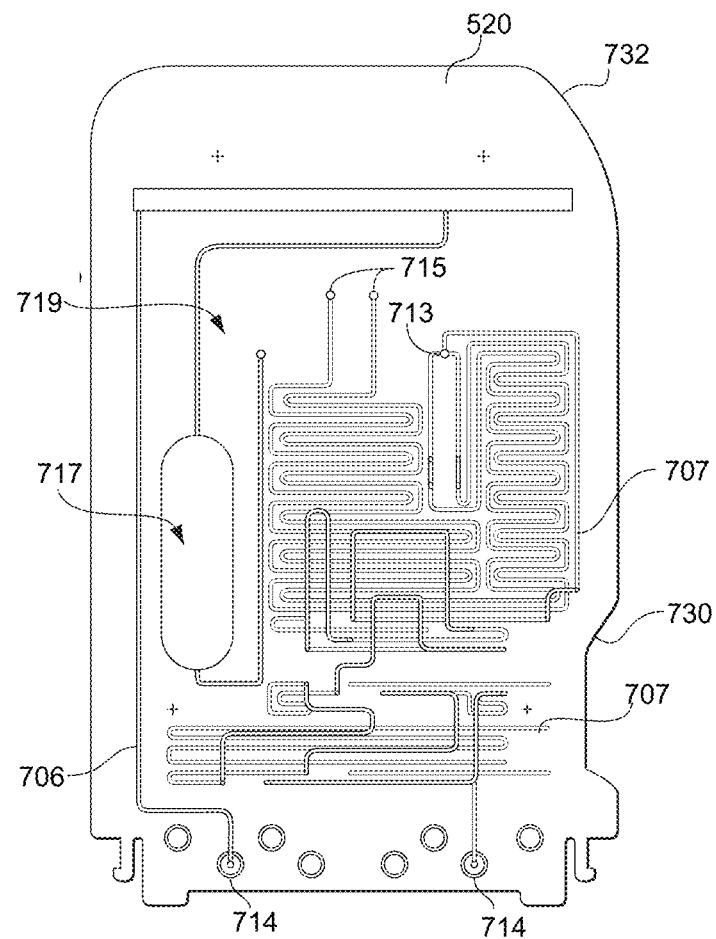
FIG. 11A is a schematic view of a cassette that can be used to determine one or more blood markers in accordance with some embodiments of the invention.
Figure 11B:
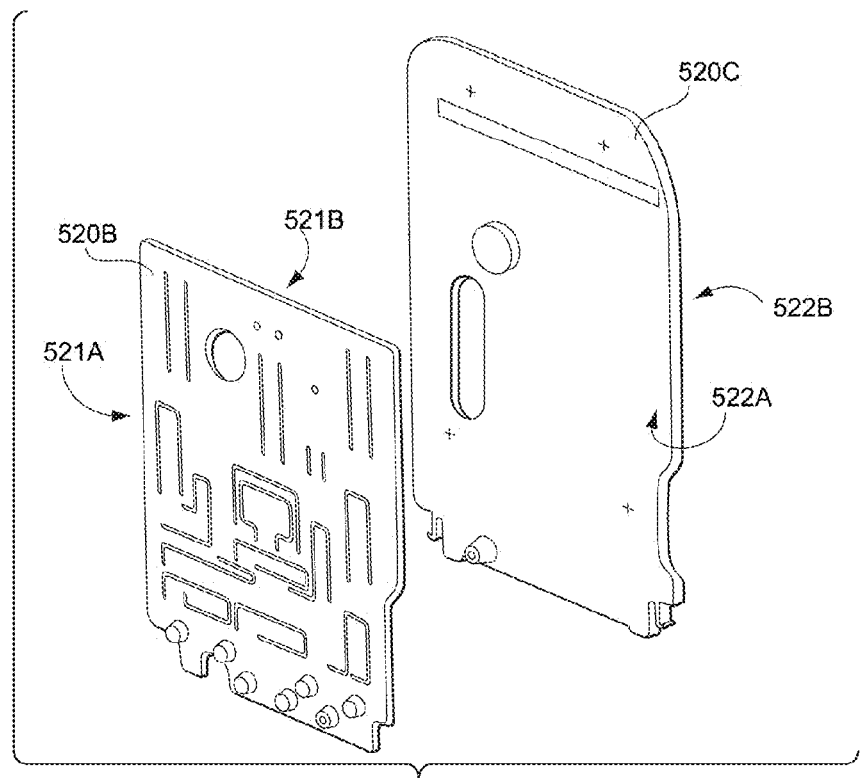
FIGS. 11B-11F are schematic views of cassettes formed of multiple components that can be used to determine one or more blood markers according to one set of embodiments.
Figure 11C:
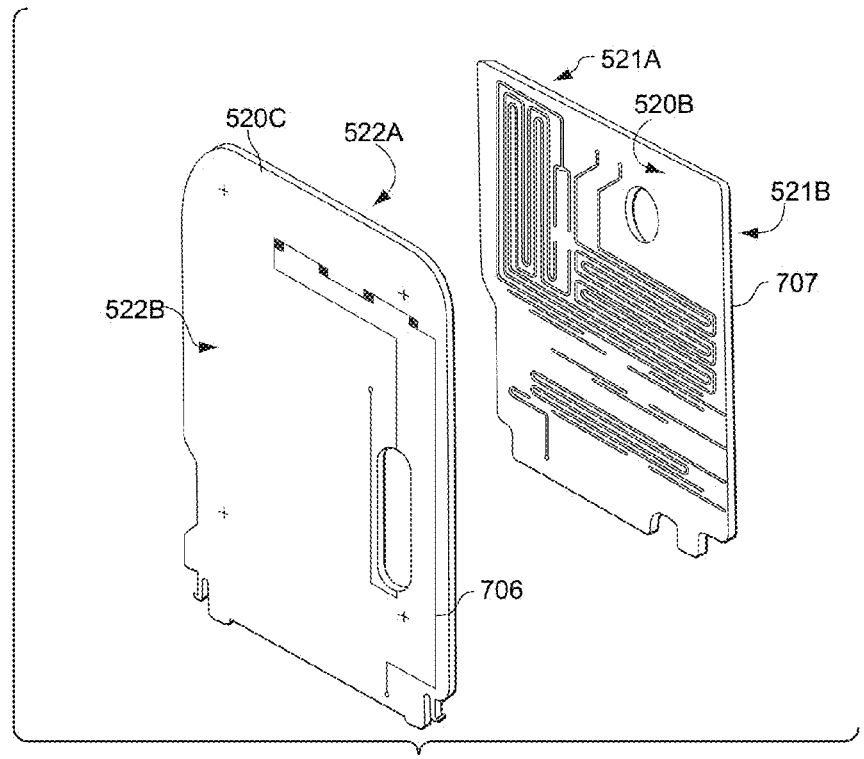
Figure 11D:
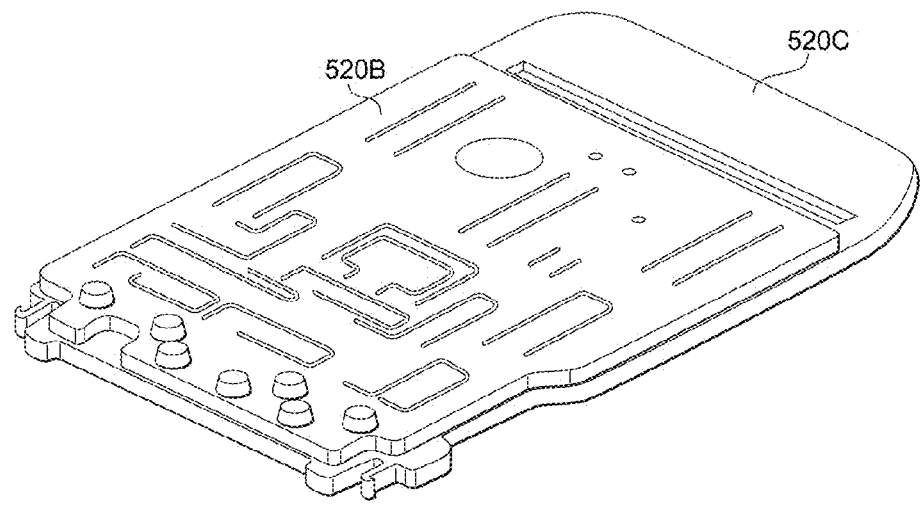
Figure 11E:
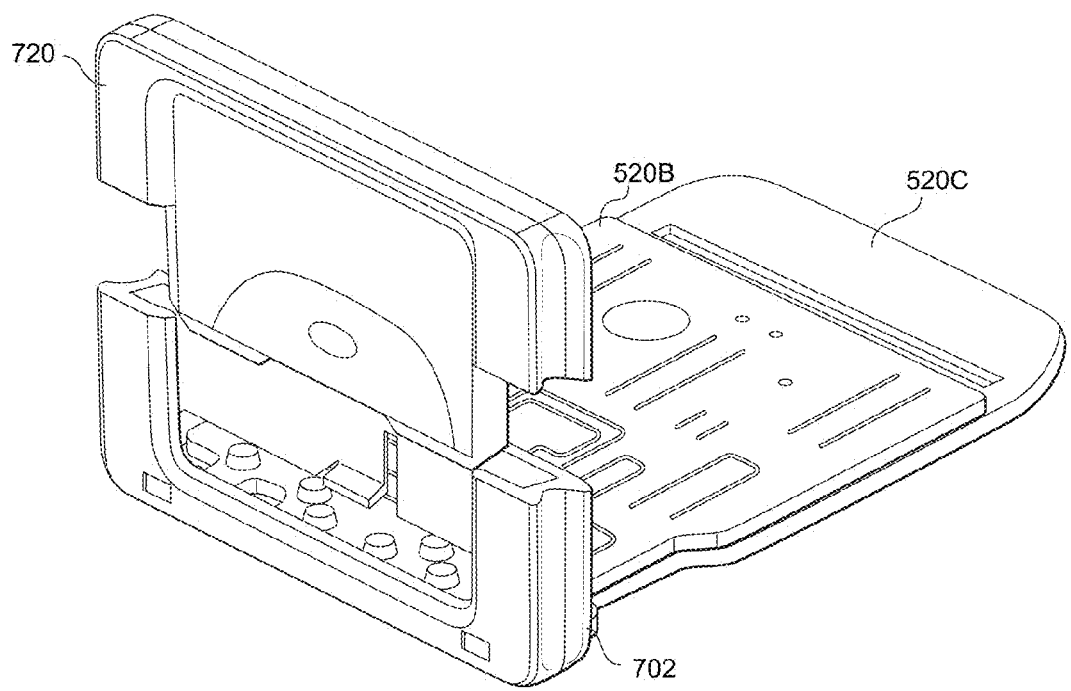
Figure 11F:
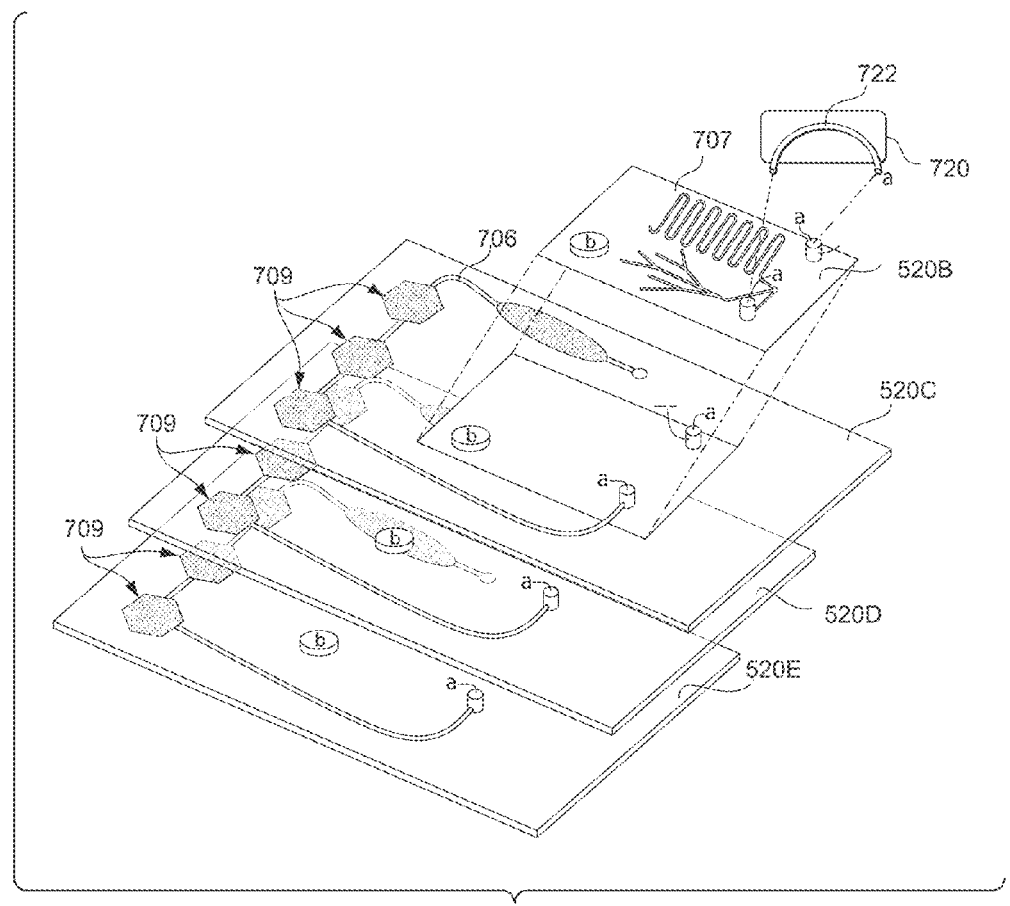

As shown illustratively in FIGS. 11D and 11E, components 520B and 520C may be substantially planar and may lay on top of one another. In general, however, the two or more components forming a cassette can lay in any suitable configuration with respect to one another. In some cases, the components lay adjacent to one another (e.g., side by side, on top of one another). The first components may completely overlap or only portions of the components may overlap with one another. For example, as shown illustratively in FIGS. 11D and 11E, component 520C may extend further than component 520B such that a portion of component 520C is not overlapping or covered by component 520B. In some cases, this configuration can be advantageous where component 520C is substantially transparent and requires light to travel through a portion of the component (e.g., a reaction area, analysis region, or detection region), and where component 520B is opaque or less transparent than component 520C.

Furthermore, the first and second components may include any suitable shape and/or configuration. For instance, in some embodiments, the first component includes a feature complementary to a feature of the second component, so as to form a non-fluidic connection between the first and second components. The complementary features may, for example, aid alignment of the first and second components during assembly.

The first and second components may be integrally connected to one another in some embodiments. As used herein, the term "integrally connected," when referring to two or more objects, means objects that do not become separated from each other during the course of normal use, e.g., cannot be separated manually; separation requires at least the use of tools, and/or by causing damage to at least one of the components, for example, by breaking, peeling, or separating components fastened together via adhesives or tools. Integrally connected components may be irreversibly attached to one another during the course of normal use. For example, components 520B and 520C may be integrally connected by use of an adhesive or by other bonding methods. In other embodiments, two or more components of a cassette may be reversibly attached to one another.

As described herein, in some embodiments at least a first component and a second component forming a composite cassette may be formed in different materials. The system may be designed such that the first component includes a first material that aids or enhances one or more functionalities of the first component. For example, if the first component is designed to store a liquid reagent (e.g., in a channel of the component) prior to first use by a user (e.g., for at least a day, a week, a month, or a year), the first material may be chosen to have a relatively low vapor permeability so as to reduce the amount of evaporation of the stored liquid over time. It should be understood, however, that the same materials may be used for multiple components (e.g., layers) of a cassette in some embodiments. For instance, both first and second components of a cassette may be formed in a material having a low water vapor permeability.

In certain embodiments, first and second components of a cassette have different degrees of optical clarity. For example, a first component may be substantially opaque, and a second component may be substantially transparent. The substantially transparent component may be suitable for optical detection of a sample or analyte contained within the component.

In one set of embodiments, a material used form a component (e.g., a first or a second component) of a cassette has an optical transmission of greater than 90% between 400 and 800 nm wavelengths of light (e.g., light in the visible range). Optical transmission may be measured through a material having a thickness of, for example, about 2 mm (or in other embodiments, about 1 mm or about 0.1 mm). In some instances, the optical transmission is greater than 80%, greater than 85%, greater than 88%, greater than 92%, greater than 94%, or greater than 96% between 400 and 800 nm wavelengths of light. Another component of the device may be formed in a material having an optical transmission of less than 96%, less than 94%, less than 92%, less than 90%, less than 85%, less than 80%, less than 50%, less than 30%, or less than 10% between 400 and 800 nm wavelengths of light.

As described herein, in some embodiments a channel of a first component of a cassette is not in fluid communication with a channel of a second component of a cassette prior to first use by a user. For instance, even after mating of the two components, as shown illustratively in FIG. 11D, channels 706 and 707 are not in fluid communication with one another. However, the cassette may further include other parts or components such as fluidic connector alignment element 702 (FIG. 11E), which can attach to first and/or second components 520B and 520C or to other portions of the cassette. As described herein, the fluidic connector alignment element may be configured to receive and mate with fluidic connector 720, which can allow fluid communication between channels 706 and 707 of the first and second components, respectively. For example, the fluidic connector may include a fluid path including a fluid path inlet and a fluid path outlet, wherein the fluid path inlet can be fluidically connected to the outlet of channel 706 and the fluid path outlet can be fluidically connected to the inlet of channel 707 (or vice versa). The fluid path of the fluidic connector may have any suitable length (e.g., at least 1 cm, at least 2 cm, at least 3 cm, at least 5 cm) for connecting the channels. The fluidic connector may be a part of a kit along with a cassette, and packaged such that the fluidic connector is not fluidically connecting channels 706 and 707.

A fluidic connector may have any suitable configuration with respect to a cassette, or components of a cassette. As shown illustratively in FIG. 11E, upon connection of the fluidic connector to the cassette, the fluidic connector may be positioned on a side of a component (e.g., component 520B) opposite another component (e.g., component 520C). In other embodiments, a fluidic connector can be positioned between two components of a cassette. For instance, the fluidic connector may be a component or layer positioned between (e.g., sandwiched between) two components of the cassette. Other configurations are also possible.

Although much of the description herein is directed towards a cassette having one or more components or layers including channel networks, in other embodiments, a cassette may include more than 2, more than 3, or more than 4 such components or layers. For example, as shown illustratively in FIG. 11F, a cassette may include components 520B, 520C, 520D, and 520E, each including at least one channel or network of channels. In some instances, the channel(s) of one or more components (e.g., 2, 3, or all components) may be fluidically unconnected prior to first use, but may be connected fluidically at first use, e.g., by use of a fluidic connector. In other embodiments, the channel(s) of one or more components (e.g., 2, 3, or all components) are connected fluidically prior to first use.

As described herein, each of the components or layers of a cassette may be designed to have a specific function that is different from a function of another component of the cassette. In other embodiments, two or more components may have the same function. For example, as shown in the illustrative embodiment of FIG. 11F, each of components 520C, 520D and 520E may have one or multiple analysis regions 709 connected in series. Upon connection of fluidic connector 722 to the composite cassette, portions of a sample (or multiple samples) may be introduced into the channel network in each of components 520C, 520D and 520E to perform multiple analyses. For instance, each of the analysis regions may include one or more binding partners for detecting one or more of iPSA, fPSA, tPSA and/or hK2 (e.g., capture antibodies for iPSA, fPSA, tPSA and/or hK2). As described herein, in some embodiments the use of specific capture antibodies and/or the separation of capture antibodies at different analysis regions may allow for the use of the same detection antibody for detection of each of the species. In some such embodiments, the same wavelength may be used to determine each of the species. This may allow for the use of simplified detectors and/or optical components for detection. For example, in some embodiments, detection involves accumulation of an opaque material at different analysis regions that can be determined at a particular wavelength.

In some embodiments, at least first and second components of a cassette may be a part of a device or a kit used for determining a particular chemical or biological condition. The device or kit may include, for example, a first component comprising a first channel in a first material, the first channel including an inlet, an outlet and, between the first inlet and outlet, at least one portion having a cross-sectional dimension greater than 200 microns. The device or kit may also include a second component comprising a second channel in a second material, the second channel including an inlet, an outlet and, between the second inlet and outlet, at least one portion having a cross-sectional dimension less than 200 microns. In some cases, the device or kit is packaged such that the first and second components are connected to one another. For example, the first and second components may be integrally connected to one another. In other embodiments, the first and second components are reversibly attached to one another. The device or kit may further include a fluidic connector for fluidically connecting the first and second channels, the fluidic connector comprising a fluid path, including a fluid path inlet and a fluid path outlet, wherein the fluid path inlet can be fluidically connected to the outlet of the first channel and the fluid path outlet can be fluidically connected to the inlet of the second channel. In some embodiments, the device or kit is packaged such that the fluidic connector is not fluidically connecting the first and second channels in the package. Upon first use of the device by an intended user, the fluidic connector can be used to bring the first and second channels into fluid communication with one another.

A cassette described herein may have any suitable volume for carrying out an analysis such as a chemical and/or biological reaction or other process. The entire volume of a cassette includes, for example, any reagent storage areas, analysis regions, liquid containment regions, waste areas, as well as any fluid connectors, and fluidic channels associated therewith. In some embodiments, small amounts of reagents and samples are used and the entire volume of the fluidic device is, for example, less than 10 mL, 5 mL, 1 mL, 500 µL, 250 µL, 100 µL, 50 µL, 25 µL, 10 µL, 5 µL, or 1 µL.

A cassette described herein may be portable and, in some embodiments, handheld. The length and/or width of the cassette may be, for example, less than or equal to 20 cm, 15 cm, 10 cm, 8 cm, 6 cm, or 5 cm. The thickness of the cassette may be, for example, less than or equal to 5 cm, 3 cm, 2 cm, 1 cm, 8 mm, 5 mm, 3 mm, 2 mm, or 1 mm. Advantageously, portable devices may be suitable for use in point-of-care settings.

It should be understood that the cassettes and their respective components described herein are exemplary and that other configurations and/or types of cassettes and components can be used with the systems and methods described herein.

The methods and systems described herein may involve variety of different types of analyses, and can be used to determine a variety of different samples. In some cases, an analysis involves a chemical and/or biological reaction. In some embodiments, a chemical and/or biological reaction involves binding. Different types of binding may take place in cassettes described herein. Binding may involve the interaction between a corresponding pair of molecules (e.g., binding partners) that exhibit mutual affinity or binding capacity, typically specific or non-specific binding or interaction, including biochemical, physiological, and/or pharmaceutical interactions. Biological binding defines a type of interaction that occurs between pairs of molecules (e.g., binding partners) including proteins, nucleic acids, glycoproteins, carbohydrates, hormones and the like. Specific examples include antibody/antigen, antibody fragment/antigen, antibody/hapten, antibody fragment/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, protein/nucleic acid repressor/inducer, ligand/cell surface receptor, virus/ligand, etc. Binding may also occur between proteins or other components and cells. In addition, devices described herein may be used for other fluid analyses (which may or may not involve binding and/or reactions) such as detection of components, concentration, etc.

In some cases, a heterogeneous reaction (or assay) may take place in a cassette; for example, a binding partner may be associated with a surface of a channel, and the complementary binding partner may be present in the fluid phase. Other solid-phase assays that involve affinity reaction between proteins or other biomolecules (e.g., DNA, RNA, carbohydrates), or non-naturally occurring molecules, can also be performed. Non-limiting examples of typical reactions that can be performed in a cassette include chemical reactions, enzymatic reactions, immuno-based reactions (e.g., antigen-antibody), and cell-based reactions.

Typical sample fluids include physiological fluids such as human or animal whole blood, blood serum, blood plasma, semen, tears, urine, sweat, saliva, cerebro-spinal fluid, vaginal secretions; in-vitro fluids used in research or environmental fluids such as aqueous liquids suspected of being contaminated by the analyte.

In some embodiments, one or more reagents that can be used to determine an analyte of a sample (e.g., a binding partner of the analyte to be determined) is stored in a channel or chamber of a cassette prior to first use in order to perform a specific test or assay. In cases where an antigen is being analyzed, a corresponding antibody or aptamer can be the binding partner associated with a surface of a microfluidic channel. If an antibody is the analyte, then an appropriate antigen or aptamer may be the binding partner associated with the surface. When a disease condition is being determined, it may be preferred to put the antigen on the surface and to test for an antibody that has been produced in the subject. It should be appreciated that while antibodies are referred to herein, antibody fragments may be used in combination with or in place of antibodies.

In some embodiments, a cassette is adapted and arranged to perform an analysis involving accumulating an opaque material on a region of a microfluidic channel, exposing the region to light, and determining the transmission of light through the opaque material. An opaque material may include a substance that interferes with the transmittance of light at one or more wavelengths. An opaque material does not merely refract light, but reduces the amount of transmission through the material by, for example, absorbing or reflecting light. Different opaque materials or different amounts of an opaque material may allow transmittance of less than, for example, 90, 80, 70, 60, 50, 40, 30, 20, 10 or 1 percent of the light illuminating the opaque material. Examples of opaque materials include molecular layers of metal (e.g., elemental metal), ceramic layers, polymeric layers, and layers of an opaque substance (e.g., a dye). The opaque material may, in some cases, be a metal that can be electrolessly deposited. These metals may include, for example, silver, copper, nickel, cobalt, palladium, and platinum.

An opaque material that forms in a channel may include a series of discontinuous independent particles that together form an opaque layer, but in one embodiment, is a continuous material that takes on a generally planar shape. The opaque material may have a dimension (e.g., a width of length) of, for example, greater than or equal to 1 micron, greater than or equal to 5 microns, greater than 10 microns, greater than or equal to 25 microns, or greater than or equal to 50 microns. In some cases, the opaque material extends across the width of the channel (e.g., an analysis region) containing the opaque material. The opaque layer may have a thickness of, for example, less than or equal to 10 microns, less than or equal to 5 microns, less than or equal to 1 micron, less than or equal to 100 nanometers or less than or equal to 10 nanometers. Even at these small thicknesses, a detectable change in transmittance can be obtained. The opaque layer may provide an increase in assay sensitivity when compared to techniques that do not form an opaque layer.

In one set of embodiments, a cassette described herein is used for performing an immunoassay (e.g., for determining tPSA, iPSA, fPSA and/or hK2) and, optionally, uses silver enhancement for signal amplification. In such an immunoassay, after delivery of a sample containing a blood marker to be detected at an analysis regions, binding between the blood marker and the corresponding binding partner can take place. One or more reagents, which may be optionally stored in a channel of the device prior to use, can then flow over this binding pair complex. One of the stored reagents may include a solution containing one or more metal colloids that binds to the antigen to be detected. For instance, a gold labeled antibody which is anti-PSA and anti-hK2 may be used to detect each of iPSA, fPSA, tPSA and/or hK2. In another example, a mixture of gold labeled antibodies, such as a gold labeled anti-hK2 antibody, gold labeled anti-PSA antibody, and/or gold labeled anti-iPSA antibody may be used for detection. Such reagents may be stored in the cassette, e.g., prior to use. The metal colloid can provide a catalytic surface for the deposition of an opaque material, such as a layer of metal (e.g., silver), on a surface of the one or more analysis regions. The layer of metal can be formed by using a two component system: a metal precursor (e.g., a solution of silver salts) and a reducing agent (e.g., hydroquinone, chlorohydroquinone, pyrogallol, metol, 4-aminophenol and phenidone), which can optionally be stored in different channels prior to use.

As a positive or negative pressure differential is applied to the system, the silver salt and reducing solutions can mix (e.g., merge at a channel intersection), and then flow over the analysis region. Therefore, if antibody-antigen binding occurs in the analysis region, the flowing of the metal precursor solution through the region can result in the formation of an opaque layer, such as a silver layer, due to the presence of the catalytic metal colloid associated with the antibody-antigen complex. The opaque layer may include a substance that interferes with the transmittance of light at one or more wavelengths. An opaque layer that is formed in the channel can be detected optically, for example, by measuring a reduction in light transmittance through a portion of the analysis region (e.g., a serpentine channel region) compared to a portion of an area that does not include the antibody or antigen. Alternatively, a signal can be obtained by measuring the variation of light transmittance as a function of time, as the film is being formed in an analysis region. The opaque layer may provide an increase in assay sensitivity when compared to techniques that do not form an opaque layer. Additionally, various amplification chemistries that produce optical signals (e.g., absorbance, fluorescence, glow or flash chemiluminescence, electrochemiluminescence), electrical signals (e.g., resistance or conductivity of metal structures created by an electroless process) or magnetic signals (e.g., magnetic beads) can be used to allow detection of a signal by a detector.

Various types of fluids can be used with the cassettes described herein. As described herein, fluids may be introduced into the cassette at first use, and/or stored within the cassette prior to first use. Fluids include liquids such as solvents, solutions and suspensions. Fluids also include gases and mixtures of gases. When multiple fluids are contained in a cassette, the fluids may be separated by another fluid that is preferably substantially immiscible in each of the first two fluids. For example, if a channel contains two different aqueous solutions, a separation plug of a third fluid may be substantially immiscible in both of the aqueous solutions. When aqueous solutions are to be kept separate, substantially immiscible fluids that can be used as separators may include gases such as air or nitrogen, or hydrophobic fluids that are substantially immiscible with the aqueous fluids. Fluids may also be chosen based on the fluid's reactivity with adjacent fluids. For example, an inert gas such as nitrogen may be used in some embodiments and may help preserve and/or stabilize any adjacent fluids. An example of an substantially immiscible liquid for separating aqueous solutions is perfluorodecalin. The choice of a separator fluid may be made based on other factors as well, including any effect that the separator fluid may have on the surface tension of the adjacent fluid plugs. It may be preferred to maximize the surface tension within any fluid plug to promote retention of the fluid plug as a single continuous unit under varying environmental conditions such as vibration, shock and temperature variations. Separator fluids may also be inert to an analysis region to which the fluids will be supplied. For example, if an analysis region includes a biological binding partner, a separator fluid such as air or nitrogen may have little or no effect on the binding partner. The use of a gas (e.g., air) as a separator fluid may also provide room for expansion within a channel of a fluidic device should liquids contained in the device expand or contract due to changes such as temperature (including freezing) or pressure variations.

The microfluidic sample analyzer may include a fluid flow source (e.g., a pressure-control system) which may be fluidly connected to the channels 706, 707, 722 to pressurize the channels to move the sample and/or other reagents through the channels. In particular, the fluid flow source may be configured to move a sample and/or reagent initially from the substantially U-shaped channel 722 into the first channel 706. The fluid flow source may also be used to move the reagents in the second channel 707 through the substantially U-shaped channel 722 and into the first channel 706. After the sample and reagents pass through the analysis regions 709 and are analyzed, the fluid flow source 540 may be configured to move the fluids into the absorbent material 717 of the cassette. In one embodiment, the fluid flow source is a vacuum system. It should be understood, however, that other sources of fluid flow such as valves, pumps, and/or other components can be used.

As described herein, in some embodiments a vacuum source may be used to drive fluid flow. A vacuum source may include a pump, such as a solenoid operated diaphragm pump. In other embodiments, fluid flow may be driven/controlled via use of other types of pumps or sources of fluid flow. For example, in one embodiment, a syringe pump may be used to create a vacuum by pulling the syringe plunger in an outward direction. In other embodiments, a positive pressure is applied to one or more inlets of the cassette to provide a source of fluid flow.

In some embodiments, fluid flow takes place while applying a substantially constant non-zero pressure drop (i.e., $\Delta P$) across an inlet and an outlet of a cassette. In one set of embodiments, an entire analysis is performed while applying a substantially constant non-zero pressure drop (i.e., $\Delta P$) across an inlet and an outlet of a cassette. A substantially constant non-zero pressure drop can be achieved, for example, by applying a positive pressure at the inlet or a reduced pressure (e.g., a vacuum) at the outlet. In some cases, a substantially constant non-zero pressure drop is achieved while fluid flow does not take place predominately by capillary forces and/or without the use of actuating valves (e.g., without changing a cross-sectional area of a channel of a fluid path of the cassette). In some embodiments, during essentially the entire analysis conducted in the cassette, a substantially constant non-zero pressure drop may be present across, for example, an inlet to an analysis region (which may be connected to a fluidic connector) and an outlet downstream of the analysis region (e.g., an outlet downstream of a liquid containment region), respectively.

In one embodiment, a vacuum source is configured to pressurize a channel to approximately −60 kPa (approximately ⅔ atmosphere). In another embodiment, the vacuum source is configured to pressurize a channel to approximately −30 kPa. In certain embodiments, a vacuum sources is configured to pressurize a channel to, for example, between −100 kPa and −70 kPa, between −70 kPa and −50 kPa, between −50 kPa and −20 kPa, or between −20 kPa and −1 kPa.

Once the cassette is positioned within the analyzer, the fluid flow source may be coupled to the cassette to ensure a fluid-tight connection. As mentioned above, the cassette may include a port configured to couple the channel 706, and channel 707 if fluidically connected to 706, with the fluid flow source. In one embodiment, seals, or o-rings are positioned around the port and a linear solenoid may be positioned above the o-rings to press and seal the o-rings against the cassette body. For example, as shown in the exemplary embodiment illustrated in FIG. 11A, in addition to the port 719, there may be two venting ports 715 and a mixing port 713. The interface between each port and the manifold may be independent (e.g., there may be no fluidic connection inside the manifold).

In one embodiment, when a fluid flow source is activated, the channel 706, 707 in the cassette may be pressurized (e.g., to approximately −30 kPa) which will drive the fluids within the channel (both fluid sample as well as reagents) toward the outlet. In an embodiment which includes the vent ports 715 and the mixing port 713, a vent valve connected to port 713 through the manifold may initially be open which may enable all of the reagents downstream of the mixing port 713 to move toward the outlet, but will not cause reagents upstream of the mixing port 713 to move. Once the vent valve is closed, reagents upstream of the mixing port 713 may move toward a mixing port and then to the outlet. For example, fluids can be stored serially in a channel upstream of the mixing port, and after closing a vent valve positioned along the channel, the fluids can flow sequentially towards the channel outlet. In some cases, fluids can be stored in separate, intersecting channels, and after closing a vent valve the fluids will flow together toward a point of intersection. This set of embodiments can be used, for example, to controllably mix the fluids as they flow together. The timing of delivery and the volume of fluid delivered can be controlled, for example, by the timing of the vent valve actuation.

Advantageously, vent valves can be operated without constricting the cross-section of the microfluidic channel on which they operate, as might occur with certain valves in the prior art. Such a mode of operation can be effective in preventing leaking across the valve. Moreover, because vent valves can be used, some systems and methods described herein do not require the use of certain internal valves, which can be problematic due to, for example, their high expense, complexity in fabrication, fragility, limited compatibility with mixed gas and liquid systems, and/or unreliability in microfluidic systems.

It should be understood that while vent valves are described, other types of valving mechanisms can be used with the systems and methods described herein. Non-limiting examples of a valving mechanism which may be operatively associated with a valve include a diaphragm valve, ball valve, gate valve, butterfly valve, globe valve, needle valve, pinch valve, poppet valve, or pinch valve. The valving mechanism may be actuated by any suitable means, including a solenoid, a motor, by hand, by electronic actuation, or by hydraulic/pneumatic pressure.

As previously mentioned, all of the liquids in the cassette (sample and reagents) may move into the liquid containment area which may include an absorbent material 717. In one embodiment, the absorbent material absorbs only liquids such that gases may flow out of the cassette through the outlet.

A variety of determination (e.g., measuring, quantifying, detecting, and qualifying) techniques may be used, e.g., to analyze a sample component or other component or condition associated with a microfluidic system or cassette described herein. Determination techniques may include optically-based techniques such as light transmission, light absorbance, light scattering, light reflection and visual techniques. Determination techniques may also include luminescence techniques such as photoluminescence (e.g., fluorescence), chemiluminescence, bioluminescence, and/or electrochemiluminescence. In other embodiments, determination techniques may measure conductivity or resistance. As such, an analyzer may be configured to include such and other suitable detection systems.

Different optical detection techniques provide a number of options for determining reaction (e.g., assay) results. In some embodiments, the measurement of transmission or absorbance means that light can be detected at the same wavelength at which it is emitted from a light source. Although the light source can be a narrow band source emitting at a single wavelength it may also may be a broad spectrum source, emitting over a range of wavelengths, as many opaque materials can effectively block a wide range of wavelengths. In some embodiments, a system may be operated with a minimum of optical devices (e.g., a simplified optical detector). For instance, the determining device may be free of a photomultiplier, may be free of a wavelength selector such as a grating, prism or filter, may be free of a device to direct or columnate light such as a columnator, or may be free of magnifying optics (e.g., lenses). Elimination or reduction of these features can result in a less expensive, more robust device.

Figure 12:
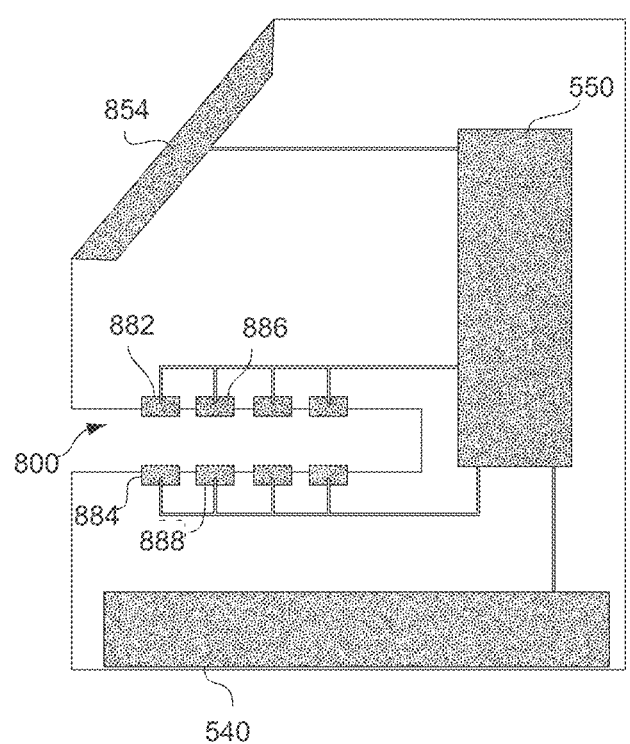
FIG. 12 is a schematic view of a portion of a sample analyzer that can be used to determine one or more blood markers in accordance with some embodiments of the invention.

FIG. 12 illustrates an exemplary optical system 800 which may be positioned in the housing of an analyzer. As shown illustratively in this embodiment, the optical system includes at least a first light source 882 and a detector 884 spaced apart from the first light source. The first light source 882 may be configured to pass light through a first analysis region of the cassette when the cassette is inserted into the analyzer. The first detector 884 may be positioned opposite the first light source 882 to detect the amount of light that passes through the first analysis region of the cassette 520. It should be appreciated that in other embodiments, the number of light sources and detectors may vary as the invention is not so limited. As mentioned above, the cassette 520 may include a plurality of analysis regions 709 and the cassette 520 may be positioned within the analyzer such that each analysis region aligns with a light source and corresponding detector. In some embodiments, the light source includes an optical aperture which may help direct light from the light source to a particular region within an analysis region of the cassette.

In one embodiment, the light sources are light emitting diodes (LEDs) or laser diodes. For example, an InGaAlP red semiconductor laser diode emitting at 654 nm may be used. Other light sources can also be used. The light source may be positioned within a nest or housing. The nest or housing may include a narrow aperture or thin tube that may assist in collimating light. The light sources may be positioned above where the cassette is inserted into the analyzer such that the light source shines down onto the top surface of the cassette. Other suitable configurations of the light source with respect to the cassette are also possible.

It should be appreciated that the wavelength of the light sources may vary as the invention is not so limited. For example, in one embodiment, the wavelength of the light source is approximately 670 nm, and in another embodiment, the wavelength of the light source is approximately 650 nm. It should be appreciated that in one embodiment, the wavelength of each light source may be different such that each analysis region of the cassette receives a different light wavelength. In other embodiments, however, the wavelength of each light source may be the same such that each analysis region of the cassette receives the same light wavelength. Combinations of the same and different wavelengths of light sources are also possible.

As mentioned, a detector 884 may be spaced apart from and positioned below a light source 882 to detect the amount of light that passes through the cassette. In one embodiment, one or more of the detectors are photodetectors (e.g., photodiodes). In certain embodiments, the photodetector may be any suitable device capable of detecting the transmission of light that is emitted by the light source. One type of photodetector is an optical integrated circuit (IC) including a photodiode having a peak sensitivity at 700 nm, an amplifier and a voltage regulator. The detector may be positioned within a nest or housing which may include a narrow aperture or thin tube to ensure that only light from the center of the analysis region 709 is measured at the detector 884. If the light source is pulse modulated, the photodetector may include a filter to remove the effect of light that is not at the selected frequency. When multiple and neighboring signals are detected at the same time, the light source used for each analysis region (e.g., detection region) can be modulated at a frequency sufficiently different from that of its neighboring light source. In this configuration, the each detector can be configured (e.g., using software) to select for its attributed light source, thereby avoiding interfering light form neighboring optical pairs.

Applicant has recognized that the amount of light transmitted through an analysis region of the cassette may be used to determine information about not only the sample, but also information about specific processes occurring in the fluidic system of the cassette (e.g., mixing of reagents, flow rate, etc.). In some cases, measurement of light through a region can be used as feedback to control fluid flow in the system. In certain embodiments, quality control or abnormalities in the operation of the cassette can be determined. For example, feedback from an analysis region to a control system can be used to determine abnormalities that have occurred in the microfluidic system, and the control system may send a signal to one or more components to cause all or portions of the system to shut down. Consequently, the quality of the processes being performed in the microfluidic system can be controlled using the systems and methods described herein.

It should be recognized that a clear liquid (such as water) may allow a large amount of light to be transmitted from the light source 882, through the analysis region 709 and to the detector 884. Air within the analysis region 709 may lead to less light transmitted through the analysis region 709 because more light may scatter within the channel compared to when a clear liquid is present. When a blood sample is in an analysis region 709, a significantly less amount of light may pass through to the detector 884 due to the light scattering off of blood cells and also due to absorbance. In one embodiment, silver associates with a sample component bound to a surface within the analysis region and as silver builds up within the analysis region, less and less light is transmitted through the analysis region 709.

It is recognized that measuring the amount of light that is detected at each detector 884 enables a user to determine which reagents are in a particular analysis region 709 at a particular point in time. It is also recognized that by measuring the amount of light that is detected with each detector 884, it is possible to measure the amount of silver deposited in each analysis region 709. This amount may correspond to the amount of analyte captured during a reaction which may thus provide a measure of the concentration of the analyte in the sample.

As noted above, Applicant has recognized that the optical system 880 may be used for a variety of quality control reasons. First, the time it takes for a sample to reach an analysis region where the optical system detects the light that passes though the analysis region may be used to determine whether there is a leak or clog in the system. Also, when the sample is expected to be a certain volume, for example, approximately 10 microliters, there is an expected flow time which would be associated for the sample to pass through the channels and analysis regions. If the sample falls outside of that expected flow time, it could be an indication that there is not enough sample to conduct the analysis and/or that the wrong type of sample was loaded into the analyzer. Additionally, an expected range of results may be determined based upon the type of sample (e.g., serum, blood, urine, etc.) and if the sample is outside of the expected range, it could be an indication of an error.

In one embodiment, the analyzer includes a temperature regulating system positioned within the housing which may be configured to regulate the temperature within the analyzer. For certain sample analysis, the sample may need to be kept within a certain temperature range. For example, in one embodiment, it is desirable to maintain the temperature within the analyzer at approximately 37° C. Accordingly, in one embodiment, the temperature regulating system includes a heater configured to heat the cassette. In one embodiment, the heater is a resistive heater which may be positioned on the underside of where the cassette is placed in the analyzer. In one embodiment, the temperature regulating system also includes a thermistor to measure the temperature of the cassette and a controller circuit may be provided to control the temperature.

In one embodiment, the passive flow of air within the analyzer may act to cool the air within the analyzer if needed. A fan may optionally be provided in the analyzer to lower the temperature within the analyzer. In some embodiments, the temperature regulating system may include Peltier thermoelectric heaters and/or coolers within the analyzer.

In certain embodiments, an identification system including one or more identifiers is used and associated with one or more components or materials associated with a cassette and/or analyzer. The "identifiers," as described in greater detail below, may themselves be "encoded with" information (i.e. carry or contain information, such as by use of an information carrying, storing, generating, or conveying device such as a radio frequency identification (RFID) tag or bar code) about the component including the identifier, or may not themselves be encoded with information about the component, but rather may only be associated with information that may be contained in, for example, a database on a computer or on a computer readable medium (e.g., information about a user, and/or sample to be analyzed). In the latter instance, detection of such an identifier can trigger retrieval and usage of the associated information from the database.

Identifiers "encoded with" information about a component need not necessarily be encoded with a complete set of information about the component. For example, in certain embodiments, an identifier may be encoded with information merely sufficient to enable a unique identification of the cassette (e.g. relating to a serial no., part no., etc.), while additional information relating to the cassette (e.g. type, use (e.g., type of assay), ownership, location, position, connectivity, contents, etc.) may be stored remotely and be only associated with the identifier.

"Information about" or "information associated with" a cassette, material, or component, etc. is information regarding the identity, positioning, or location of the cassette, material or component or the identity, positioning, or location of the contents of a cassette, material or component and may additionally include information regarding the nature, state or composition of the cassette, material, component or contents. "Information about" or "information associated with" a cassette, material or component or its contents can include information identifying the cassette, material or component or its contents and distinguishing the cassette, material, component or its contents from others. For example, "information about" or "information associated with" a cassette, material or component or its contents may refer to information indicating the type or what the cassette, material or component or its contents is, where it is or should be located, how it is or should be positioned, the function or purpose of the cassette, material or component or its contents, how the cassette, material or component or its contents is to be connected with other components of the system, the lot number, origin, calibration information, expiration date, destination, manufacturer or ownership of the cassette, material or component or its contents, the type of analysis/assay to be performed in the cassette, information about whether the cassette has been used/analyzed, etc.

Non-limiting examples of identifiers that may be used in the context of the invention include radio frequency identification (RFID) tags, bar codes, serial numbers, color tags, fluorescent or optical tags (e.g., using quantum dots), chemical compounds, radio tags, magnetic tags, among others.

In one embodiment, an identification reader is an RFID reader configured to read an RFID identifier associated with the cassette. For example, in one embodiment, the analyzer includes an RFID module and antenna that are configured to read information from the cassette inserted into the analyzer. In another embodiment, the identification reader is a barcode reader configured to read a barcode associated with the cassette. Once the cassette is inserted into the analyzer, the identification reader may read the information from the cassette. The identifier on the cassette may include one or more of the types of information such as cassette type, type of analysis/assay to be performed, lot number, information about whether the cassette has been used/analyzed, and other information described herein. The reader may also be configured to read information provided with a group of cassettes, such as in a box of cassettes, such as, but not limited to calibration information, expiration date, and any additional information specific to that lot. The information identified may be optionally displayed to a user, e.g., to confirm that a correct cassette and/or type of assay is being performed.

In some cases, the identification reader may be integrated with a control system via communication pathways. Communication between the identification readers and the control system may occur along a hard-wired network or may be transmitted wirelessly. In one embodiment, the control system can be programmed to recognize a specific identifier (e.g., of a cassette associated with information relating to a cassette type, manufacturer, assay to be performed, etc.) as indicating the cassette is suitably connected or inserted within a particular type of analyzer.

In one embodiment, the identifier of a cassette be associated with predetermined or programmed information contained in a database regarding the use of the system or cassette for a particular purpose, user or product, or with particular reaction conditions, sample types, reagents, users, and the like. If an incorrect match is detected or an identifier has been deactivated, the process may be halted or the system may be rendered not operable until the user has been notified, or upon acknowledgement by a user.

The information from or associated with an identifier can, in some embodiments, be stored, for example in computer memory or on a computer readable medium, for future reference and record-keeping purposes. For example, certain control systems may employ information from or associated with identifiers to identify which components (e.g., cassettes) or type of cassettes were used in a particular analysis, the date, time, and duration of use, the conditions of use, etc. Such information may be used, for example, to determine whether one or more components of the analyzer should be cleaned or replaced. Optionally, a control system or any other suitable system could generate a report from gathered information, including information encoded by or associated with the identifiers, that may be used in providing proof of compliance with regulatory standards or verification of quality control.

Information encoded on or associated with an identifier may also be used, for example, to determine whether the component associated with the identifier (e.g., a cassette) is authentic or counterfeit. In some embodiments, the determination of the presence of a counterfeit component causes system lockout. In one example, the identifier may contain a unique identity code. In this example, the process control software or analyzer would not permit system startup (e.g., the system may be disabled) if a foreign or mismatched identity code (or no identity code) was detected.

In certain embodiments, the information obtained from or associated with an identifier can be used to verify the identity of a customer to whom the cassette and/or analyzer is sold or for whom a biological, chemical, or pharmaceutical process is to be performed. In some cases, the information obtained from or associated with an identifier is used as part of a process of gathering data for troubleshooting a system. The identifier may also contain or be associated with information such as batch histories, assembly process and instrumentation diagrams (P and IDs), troubleshooting histories, among others. Troubleshooting a system may be accomplished, in some cases, via remote access or include the use of diagnostic software.

In one embodiment, the analyzer includes a user interface, which may be positioned within the housing and configured for a user to input information into the sample analyzer. In one embodiment, the user interface is a touch screen.

The touch screen may guide a user through the operation of the analyzer, providing text and/or graphical instructions for use of the analyzer. The touch screen user interface may, for example, guide the user to insert the cassette into the analyzer. It may then guide the user to input the patient's name or other patient identification source/number into the analyzer (e.g., age, results of a DRE exam, etc.). It should be appreciated that the patient information such as name, date of birth, and/or patient ID number may be inputted into the touch screen user interface to identify the patient. The touch screen may indicate the amount of time remaining to complete the analysis of the sample. The touch screen user interface may then illustrates the results of the sample analysis along with the patient's name or other identifying information.

In another embodiment, the user interface may be configured differently, such as with an LCD display and a single button scroll through menu. In another embodiment, the user interface may simply include a start button to activate the analyzer. In other embodiments, the user interface from separate independent devices (such as a smart phone or mobile computer) can be used to interface with the analyzer.

The above-described analyzer may be used in a variety of ways to process and analyze a sample placed within the analyzer. In one particular embodiment, once a mechanical component configured to interface with the cassette indicates that the cassette is properly loaded in the analyzer, the identification reader reads and identifies information associated with the cassette. The analyzer may be configured to compare the information to data stored in a control system to ensure that it has calibration information for this particular sample. In the event that the analyzer does not have the proper calibration information, the analyzer may output a request to the user to upload the specific information needed. The analyzer may also be configured to review expiration date information associated with the cassette and cancel the analysis if the expiration date has passed.

In one embodiment, once the analyzer has determined that the cassette may be analyzed, a fluid flow source such as the vacuum manifold may be configured to contact the cassette to ensure an airtight seal around the vacuum port and vent ports. In one embodiment, the optical system may take initial measurements to obtain reference readings. Such reference readings may be taken both with the light sources activated and deactivated.

To initiate movement of the sample, the vacuum system may be activated, which may rapidly change the pressure within one or more channels (e.g., reduced to approximately −30 kPa). This reduction of pressure within the channel may drive the sample into a channel and through each of the analysis regions 709A-709D (see FIG. 10). After the sample reaches the final analysis region 709D, the sample may continue to flow into the liquid containment region 717.

In one particular set of embodiments, the microfluidic sample analyzer is used to measure the level of iPSA, fPSA, tPSA and/or hK2 in a blood sample. In some embodiments, three, four, five, six or more analysis regions (e.g., analysis regions 709A-709D) may be utilized to analyze the sample. For example, in a first analysis region, the walls of the channel may be blocked with a blocking protein (such as Bovine Serum Albumin) such that little or no proteins in the blood sample attach to the walls of the analysis region (except for perhaps some non-specific binding which may be washed off). This first analysis region may act as a negative control.

In a second analysis region, the walls of the channel may be coated with a predetermined large quantity of a prostate specific antigen (PSA) to act as a high or positive control. As the blood sample passes through the second analysis region, little or no PSA proteins in the blood may bind to the walls of the channel. Gold conjugated detection antibodies in the sample may be dissolved from inside of the fluidic connector tube 722 or may be flowed from any other suitable location. These antibodies may not yet be bound to the PSA in the sample, and thus they may bind to the PSA on the walls of the channel to act as a high or positive control.

In a third analysis region, the walls of the channel may be coated with a capture antibody for iPSA (e.g., an anti-iPSA antibody), which may bind to a different epitope on the PSA protein than the gold conjugated signal antibody. As the blood sample flows through the third analysis region, iPSA proteins in the blood sample may bind to the anti-iPSA antibody in a way that is proportional to the concentration of these proteins in the blood.

In a fourth analysis region, the walls of the channel may be coated with a capture antibody for fPSA (e.g., an anti-fPSA antibody), which may bind to a different epitope on the PSA protein than the gold conjugated signal antibody. As the blood sample flows through the fourth analysis region, fPSA proteins in the blood sample may bind to the anti-fPSA antibody in a way that is proportional to the concentration of these proteins in the blood.

In a fifth analysis region, the walls of the channel may be coated with a capture antibody for tPSA (e.g., an anti-tPSA antibody), which may bind to a different epitope on the PSA protein than the gold conjugated signal antibody. As the blood sample flows through the fifth analysis region, tPSA proteins in the blood sample may bind to the anti-tPSA antibody in a way that is proportional to the concentration of these proteins in the blood.

Optionally, in a sixth analysis region, the walls of the channel may be coated with a capture antibody for hK2 (e.g., an anti-hK2 antibody), which may bind to a different epitope on the protein than the gold conjugated signal antibody. As the blood sample flows through the sixth analysis region, hK2 proteins in the blood sample may bind to the anti-hK2 antibody in a way that is proportional to the concentration of these proteins in the blood.

A detection antibody such as a gold labeled antibody which is anti-PSA and anti-hK2 may be used to detect each of iPSA, fPSA, tPSA and/or hK2. In other embodiments, however, a mixture of gold labeled antibodies, such as a gold labeled anti-hK2 antibody, gold labeled anti-PSA antibody, and/or gold labeled anti-iPSA antibody may be used for detection. In some embodiments, gold conjugated detection antibodies in the sample may be dissolved from inside of the fluidic connector tube 722, or may be flowed from any other suitable location.

In some instances, measurements from a region that analyzes the can be used not only to determine the concentration of an analyte in a sample, but also as a control as well. For example, a threshold measurement can be established at an early phase of amplification. Measurements above this value (or below this value) may indicate that the concentration of analyte is outside the desired range for the assay. This technique may be used to identify, for example, whether a High Dose Hook Effect is taking place during the analysis, i.e., when a very high concentration of analyte gives an artificially low reading.

In other embodiments, different numbers of analysis regions can be provided, and an analysis may optionally include more than one analysis regions that actually test the sample. Additional analysis regions can be used to measure additional analytes so that the system can perform multiplex assays simultaneously with a single sample.

In one particular embodiment, it takes approximately eight minutes for a 10 microliter blood sample to flow through the four analysis regions. The start of this analysis may be calculated when the pressure within the channel is approximately −30 kPa. During this time, the optical system is measuring the light transmission for each analysis region, and in one embodiment, this data may be transmitted to a control system approximately every 0.1 seconds. Using reference values, these measurements may be converted using the following formulas:

$$\text{Transmission} = (l - ld)/(lr - ld) \quad (1)$$

where:
l = the intensity of transmitted light through an analysis region at a given point in time
ld = the intensity of transmitted light through an analysis region with the light source off
lr = a reference intensity (i.e. the intensity of the transmitted light at an analysis region with the light source activated, or before the start of an analysis when only air is in the channel and $$\text{Optical Density} = -\log(\text{Transmission}) \quad (2)$$

Thus, using these formulas, the optical density in an analysis region may be calculated.

Figure 13:
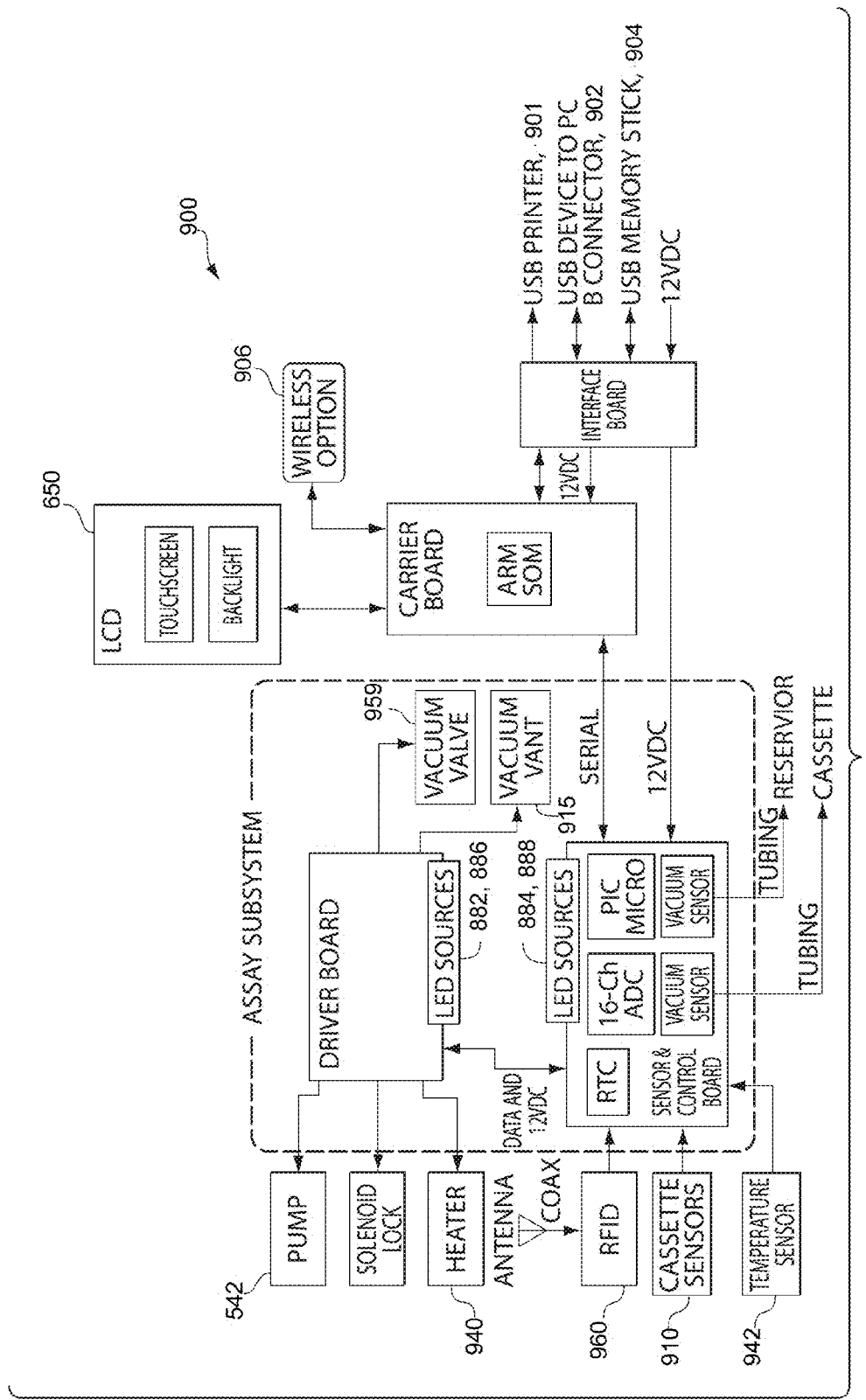
FIG. 13 is a block diagram showing a control system of a sample analyzer associated with a variety of different components that can be used to determine one or more blood markers in accordance with some embodiments of the invention.

FIG. 13 is a block diagram 900 that illustrates how a control system 550 (see FIG. 12) may be operatively associated with a variety of different components according to one embodiment. Control systems described herein can be implemented in numerous ways, such as with dedicated hardware or firmware, using a processor that is programmed using microcode or software to perform the functions recited above or any suitable combination of the foregoing. A control system may control one or more operations of a single analysis (e.g., for a biological, biochemical or chemical reaction), or of multiple (separate or interconnected) analyses. For example, the control system may be positioned within the housing of the analyzer and may be configured to communicate with an identification reader, the user interface, the fluid flow source, the optical system, and/or the temperature regulating system to analyze a sample in the cassette.

In one embodiment, the control system includes at least two processors, including a real time processor that controls and monitors all of the sub-systems which directly interface with the cassette. In one embodiment, at a particular time interval (e.g., every 0.1 seconds), this processor communicates with a second higher level processor which communicates with the user through the user interface and/or the communication sub-system (discussed below) and directs the operation of the analyzer (e.g., determines when to start analyzing a sample and interprets the results). In one embodiment, communication between these two processors occurs through a serial communication bus. It should be appreciated that in another embodiment, the analyzer may only include one processor, or more than two processors, as the invention is not so limited.

In one embodiment, the analyzer is capable of interfacing with external devices and may, for example, include ports for connection with one or more external communication units. External communication may be accomplished, for example, via USB communication. For example, as shown in FIG. 13, the analyzer may output the results of a sample analysis to a USB printer 901, or to a computer 902. Additionally, the data stream produced by the real time processor may be outputted to a computer or a USB memory stick 904. In some embodiments, a computer may be able to directly control the analyzer through a USB connection as well. Further, other types of communication options are available as the present invention is not limited in this respect. For example, Ethernet, Bluetooth and/or WI-FI communication with the analyzer may be established through the processor.

The calculation methods, steps, simulations, algorithms, systems, and system elements described herein may be implemented using a computer implemented control system, such as the various embodiments of computer implemented systems described below. The methods, steps, systems, and system elements described herein are not limited in their implementation to any specific computer system described herein, as many other different machines may be used.

The computer implemented control system can be part of or coupled in operative association with a sample analyzer, and, in some embodiments, configured and/or programmed to control and adjust operational parameters of the sample analyzer, as well as analyze and calculate values, as described above. In some embodiments, the computer implemented control system can send and receive reference signals to set and/or control operating parameters of the sample analyzer and, optionally, other system apparatus. In other embodiments, the computer implemented system can be separate from and/or remotely located with respect to the sample analyzer and may be configured to receive data from one or more remote sample analyzer apparatus via indirect and/or portable means, such as via portable electronic data storage devices, such as magnetic disks, or via communication over a computer network, such as the Internet or a local intranet.

The computer implemented control system may include several known components and circuitry, including a processing unit (i.e., processor), a memory system, input and output devices and interfaces (e.g., an interconnection mechanism), as well as other components, such as transport circuitry (e.g., one or more busses), a video and audio data input/output (I/O) subsystem, special-purpose hardware, as well as other components and circuitry, as described below in more detail. Further, the computer system may be a multi-processor computer system or may include multiple computers connected over a computer network.

The computer implemented control system may include a processor, for example, a commercially available processor such as one of the series x86, Celeron and Pentium processors, available from Intel, similar devices from AMD and Cyrix, the 680X0 series microprocessors available from Motorola, the PowerPC microprocessor from IBM, and ARM processors. Many other processors are available, and the computer system is not limited to a particular processor.

A processor typically executes a program called an operating system, of which WindowsNT, Windows95 or 98, Windows 7, Windows 8, UNIX, Linux, DOS, VMS, MacOS and OSX, and iOS are examples, which controls the execution of other computer programs and provides scheduling, debugging, input/output control, accounting, compilation, storage assignment, data management and memory management, communication control and related services. The processor and operating system together define a computer platform for which application programs in high-level programming languages are written. The computer implemented control system is not limited to a particular computer platform.

The computer implemented control system may include a memory system, which typically includes a computer readable and writeable non-volatile recording medium, of which a magnetic disk, optical disk, a flash memory and tape are examples. Such a recording medium may be removable, for example, a floppy disk, read/write CD or memory stick, or may be permanent, for example, a hard drive.

Such a recording medium stores signals, typically in binary form (i.e., a form interpreted as a sequence of one and zeros). A disk (e.g., magnetic or optical) has a number of tracks, on which such signals may be stored, typically in binary form, i.e., a form interpreted as a sequence of ones and zeros. Such signals may define a software program, e.g., an application program, to be executed by the microprocessor, or information to be processed by the application program.

The memory system of the computer implemented control system also may include an integrated circuit memory element, which typically is a volatile, random access memory such as a dynamic random access memory (DRAM) or static memory (SRAM). Typically, in operation, the processor causes programs and data to be read from the non-volatile recording medium into the integrated circuit memory element, which typically allows for faster access to the program instructions and data by the processor than does the non-volatile recording medium.

The processor generally manipulates the data within the integrated circuit memory element in accordance with the program instructions and then copies the manipulated data to the non-volatile recording medium after processing is completed. A variety of mechanisms are known for managing data movement between the non-volatile recording medium and the integrated circuit memory element, and the computer implemented control system that implements the methods, steps, systems and system elements described above in relation to FIG. 13 is not limited thereto. The computer implemented control system is not limited to a particular memory system.

At least part of such a memory system described above may be used to store one or more data structures (e.g., look-up tables) or equations described above. For example, at least part of the non-volatile recording medium may store at least part of a database that includes one or more of such data structures. Such a database may be any of a variety of types of databases, for example, a file system including one or more flat-file data structures where data is organized into data units separated by delimiters, a relational database where data is organized into data units stored in tables, an object-oriented database where data is organized into data units stored as objects, another type of database, or any combination thereof.

The computer implemented control system may include a video and audio data I/O subsystem. An audio portion of the subsystem may include an analog-to-digital (A/D) converter, which receives analog audio information and converts it to digital information. The digital information may be compressed using known compression systems for storage on the hard disk to use at another time. A typical video portion of the I/O subsystem may include a video image compressor/decompressor of which many are known in the art. Such compressor/decompressors convert analog video information into compressed digital information, and vice-versa. The compressed digital information may be stored on hard disk for use at a later time.

The computer implemented control system may include one or more output devices. Example output devices include a cathode ray tube (CRT) display, liquid crystal displays (LCD) and other video output devices, printers, communication devices such as a modem or network interface, storage devices such as disk or tape, and audio output devices such as a speaker.

The computer implemented control system also may include one or more input devices. Example input devices include a keyboard, keypad, track ball, mouse, pen and tablet, communication devices such as described above, and data input devices such as audio and video capture devices and sensors. The computer implemented control system is not limited to the particular input or output devices described herein.

It should be appreciated that one or more of any type of computer implemented control system may be used to implement various embodiments described herein. Aspects of the invention may be implemented in software, hardware or firmware, or any combination thereof. The computer implemented control system may include specially programmed, special purpose hardware, for example, an application-specific integrated circuit (ASIC). Such special-purpose hardware may be configured to implement one or more of the methods, steps, simulations, algorithms, systems, and system elements described above as part of the computer implemented control system described above or as an independent component.

The computer implemented control system and components thereof may be programmable using any of a variety of one or more suitable computer programming languages. Such languages may include procedural programming languages, for example, C, Pascal, Fortran and BASIC, object-oriented languages, for example, C++, Java and Eiffel and other languages, such as a scripting language or even assembly language.

The methods, steps, simulations, algorithms, systems, and system elements may be implemented using any of a variety of suitable programming languages, including procedural programming languages, object-oriented programming languages, other languages and combinations thereof, which may be executed by such a computer system. Such methods, steps, simulations, algorithms, systems, and system elements can be implemented as separate modules of a computer program, or can be implemented individually as separate computer programs. Such modules and programs can be executed on separate computers.

Such methods, steps, simulations, algorithms, systems, and system elements, either individually or in combination, may be implemented as a computer program product tangibly embodied as computer-readable signals on a computer-readable medium, for example, a non-volatile recording medium, an integrated circuit memory element, or a combination thereof. For each such method, step, simulation, algorithm, system, or system element, such a computer program product may comprise computer-readable signals tangibly embodied on the computer-readable medium that define instructions, for example, as part of one or more programs, that, as a result of being executed by a computer, instruct the computer to perform the method, step, simulation, algorithm, system, or system element.

It should be appreciated that various embodiments may be formed with one or more of the above-described features. The above aspects and features may be employed in any suitable combination as the present invention is not limited in this respect. It should also be appreciated that the drawings illustrate various components and features which may be incorporated into various embodiments. For simplification, some of the drawings may illustrate more than one optional feature or component. However, the invention is not limited to the specific embodiments disclosed in the drawings. It should be recognized that the invention encompasses embodiments which may include only a portion of the components illustrated in any one drawing figure, and/or may also encompass embodiments combining components illustrated in multiple different drawing figures.

Other Preferred Embodiments

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

EXAMPLES

Example 1

Studies

In total, seven separate studies using the statistical model have been carried out. The studies comprise a total of 7,647 men with elevated PSA and 2,270 cancers, with five studies constituting external validation. Further, the studies were systematically designed to cover a wide range of clinical scenarios. Perhaps most importantly, one of the studies included a natural history approach. Because biopsy outcome is a surrogate endpoint—what matters is not whether a man has prostate cancer, but whether he is at risk for a prostate cancer that will affect his life—the ideal study would take blood from patients, then follow them for several years in the absence of further screening to determine prostate cancer outcomes. We have been fortunate enough to have been able to conduct such a study [Vickers, A. J., et al., Cancer Epidemiol Biomarkers Prev, 2011. 20(2): p. 255-61].

The Malmö Diet and Cancer cohort is part of a large population-based study to identify dietary risk factors of cancer mortality, 11,063 men who were living in the city of Malmö, Sweden and born between 1923 and 1945, provided an EDTA anti-coagulated blood sample 1991-1996. Outcome ascertainment was via the Swedish Cancer Registry. Marker values were obtained from archived blood samples analyzed in 2008 that have been previously validated as obtaining accurate kallikrein measures from stored blood [Ulmert, D., et al., Clin. Chem., 2006. 52(2): p. 235-9]. The rate of PSA testing was very low, with almost all cases diagnosed clinically. As such, the study follows the "natural history" of prostate cancer in men with elevated PSA. Of 792 men who had a PSA 3 ng/ml at baseline, 474 were subsequently diagnosed with prostate cancer, at a median follow-up of 11 years.

The predictive discrimination of the four kallikrein panel statistical model was importantly higher than PSA for both prediction of any cancer and advanced cancers (stage T3 or T4, or metastatic) exactly those cancers most likely to be fatal. As found in previous studies, approximately 50% of men had a risk of prostate cancer from the model less than 20%. We estimated that only 13 men per 1000 with elevated PSA would have a risk <20% from the model, yet be diagnosed with cancer within five years; only 1 man would have cancer that was advanced at diagnosis.

The Malmö cohort demonstrates several important features of our predictive model. First, it constitutes an external validation. Second, it shows that the model predicts clinically diagnosed cancers that, by definition, do not constitute overdiagnosis. Third, the study suggests that cancers missed by the model are those considered overdiagnosis: data from our biopsy studies indicate that the panel classifies as low risk about 60 men per 1000 who have biopsy detectable cancers; the Malmö cohort data suggests that fewer than 1 in 4 of these would become clinically apparent after 5 years of follow-up. Fourth, it demonstrates that the model is very strongly predictive of the sort of aggressive cancers most likely to shorten a man's life. Finally, the data indicate that clinical use of the model would not lead to important harm in terms of delayed diagnoses, as only 1 man per 1000 would have a low risk of prostate cancer according to the model but would subsequently be diagnosed with advanced cancer. An overview of our studies on our model is given in Table 2.

In sum, our preliminary studies can be summarized as follows:

1. Multiple kallikrein forms in blood—total PSA, free PSA, intact PSA and hK2—can predict the result of prostate biopsy in men with elevated total PSA.

2. A statistical prediction model based on the four kallikreins was built using a single training set.

3. This integrates information from the novel markers with the clinical exam in order to give a predicted probability of cancer.

4. In total, the panel has been applied to over 7,500 men diagnosed with close to 2250 cancers, with five separate studies constituting external validation.

5. The model is highly discriminatory for prostate cancer, with a much higher AUC than a statistical model based on standard predictors alone (total PSA, age and digital rectal exam).

6. Use of the four-kallikrein statistical prediction model to determine referral to prostate biopsy would, according to decision analysis, improve clinical outcome in comparison to alternative strategies, such as performing biopsies on all men.

7. The model was of value in a range of different clinical settings: with and without prior screening; with and without prior biopsy; with and without clinical work up before referral to biopsy.

TABLE 2

Overview of studies

| Cohort | Description | Sample size | Increase in AUC: four kallikrein model vs. PSA | Increase in AUC: four kallikrein panel plus DRE model vs. PSA + DRE |
|---|---|---|---|---|
| Gothenburg round 1 | Unscreened men | 740 | Any cancer: 0.832 vs. 0.680 High grade: 0.870 vs. 0.816 | Any cancer: 0.836 vs. 0.724 High grade: 0.903 vs. 0.868 |
| Gothenburg subsequent rounds | Men with a prior PSA test | 1241 | Any cancer: 0.674 vs. 0.564 High grade: 0.819 vs. 0.658 | Any cancer: 0.697 vs. 0.622 High grade: 0.828 vs. 0.717 |
| Rotterdam round 1 | Unscreened men | 2186 | Any cancer: 0.764 vs. 0.637 High grade: 0.825 vs. 0.776 | Any cancer: 0.776 vs. 0.695 High grade: 0.837 vs. 0.806 |
| Rotterdam subsequent rounds | Men with a prior PSA test | 1501 | Any cancer: 0.713 vs. 0.557 High grade: 0.793 vs. 0.699 | Any cancer: 0.711 vs. 0.585 High grade: 0.798 vs. 0.709 |
| Rotterdam prior negative biopsy | Persistently elevated PSA after negative biopsy | 925 | Not assessed | Any cancer: 0.681 vs. 0.584 High grade: 0.873 vs. 0.764 |
| Tarn | Clinical work up before biopsy | 262 | Not assessed | Any cancer: 0.782 vs. 0.628 High grade: 0.870 vs. 0.767 |
| Malmo | Longitudinal follow-up without biopsy or screening | 792 | Any cancer: 0.751 vs. 0.654 Advanced cancer*: 0.824 vs. 0.716 | Not assessed |

*T3/T4 or metastatic at diagnosis

8. Application of the model to archived bloods in men followed longitudinally without screening demonstrated that men with elevated PSA, but at low risk from the statistical model, were highly unlikely to develop aggressive cancers over the subsequent 5 to 10 years. Conversely, clinically-diagnosed aggressive cancers were common in men at high risk from the model.

An Illustrative Model Used in this Example:
  Age: enter age in years
  tPSA: enter total PSA in ng/ml
  fPSA: enter free PSA in ng/ml
  iPSA: enter intact PSA in ng/ml
  hK2: enter hK2 in ng/ml If $tPSA \geq 25$ then use: $L = 0.0733628 \times tPSA - 1.377984$ risk of prostate cancer $= \exp(L)/[1+\exp(L)]$ If tPSA<25 then use one of two equations below, one incorporating clinical information and the other not:
The cubic spline variables are determined as follows:

$$\text{Spline1\_}tPSA = -(162-4.4503)/(162-3) \times (tPSA-3)^3 + \max(tPSA-4.4503,0)^3$$

$$\text{Spline2\_}tPSA = -(162-6.4406)/(162-3) \times (tPSA-3)^3 + \max(tPSA-6.4406,0)^3$$

If $fPSA<11.8$, then $\text{Spline1\_}fPSA = -(11.8-0.84)/(11.8-0.25) \times (fPSA-0.25)^3 + \max(fPSA-0.84,0)^3$ If $fPSA>11.8$, then $\text{Spline1\_}fPSA = (11.8-0.84) \times (0.84-0.25) \times (11.8+0.84+0.25-3 \times fPSA)$ If $fPSA<11.8$, then $\text{Spline2\_}fPSA = -(11.8-1.29)/(11.8-0.25) \times (fPSA-0.25)^3 + \max(fPSA-1.29,0)^3$ If $fPSA>11.8$, then $\text{Spline2\_}fPSA = (11.8-1.29) \times (1.29-0.25) \times (11.8+1.29+0.25-3 \times fPSA)$ For the Laboratory Model:
  Define the Following:

$x1 = 0.0846726 \times tPSA + -0.0211959 \times \text{Spline1\_}tPSA + 0.0092731 \times \text{Spline2\_}tPSA$ $x2 = -3.717517 \times fPSA - 0.6000171 \times \text{Spline1\_}fPSA + 0.275367 \times \text{Spline2\_}fPSA$ $x3 = 3.968052 \times iPSA$ $$x4 = 4.508231 \times hK2$$

Then:

$$L = -1.735529 + 0.0172287 \times \text{Age} + x1 + x2 + x3 + x4$$

risk of prostate cancer$=\exp(L)/[1+\exp(L)]$

This gives the risk of prostate cancer in the absence of any clinical information. We assume that, if this risk is high, the clinician will ask the patient to present for a clinical work-up and digital rectal exam. The following model is then run twice, with DRE coded as 0 or 1, to give risks depending on whether the DRE is normal or abnormal respectively.

Define the Following:

$$x1 = 0.0637121 \times t\text{PSA} - 0.0199247 \times \text{Spline1\_}t\text{PSA} + 0.0087081 \times \text{Spline2\_}t\text{PSA}$$

$$x2 = -3.460508 \times f\text{PSA} - 0.4361686 \times \text{Spline1\_}f\text{PSA} + 0.1801519 \times \text{Spline2\_}f\text{PSA}$$

$$x3 = 4.014925 \times i\text{PSA}$$

$$x4 = 3.523849 \times hK2$$

Then Risk if DRE Positive is:

$$L = -1.373544 + 0.9661025 + 0.0070077 \times \text{Age} + x1 + x2 + x3 + x4$$

For DRE Negative:

$$L = -1.373544 + 0.0070077 \times \text{Age} + x1 + x2 + x3 + x4$$

Determine Risk as:

risk of prostate cancer$=\exp(L)/[1+\exp(L)]$

For Recalibration:

Recalibration may be used for men with prior negative biopsy, but recalibration can be used in other situations where the event rates is importantly different from observed event rate in (previously unscreened) Rotterdam cohort (29%).

Define the Following:

odds_cancer$=Pr(\text{cancer})/(1-(Pr(\text{cancer})))$ odds_prediction=predicted risk of cancer/(1−predicted risk of cancer) Then:

bayes_factor=odds_cancer/odds_prediction $y\_\text{adj} = y + \log(\text{bayesfactor})$ recalibrated risk of prostate cancer$=\exp(y\_\text{adj})/[1+\exp(y\_\text{adj})]$

Example 2

Prophetic

Figure 14:
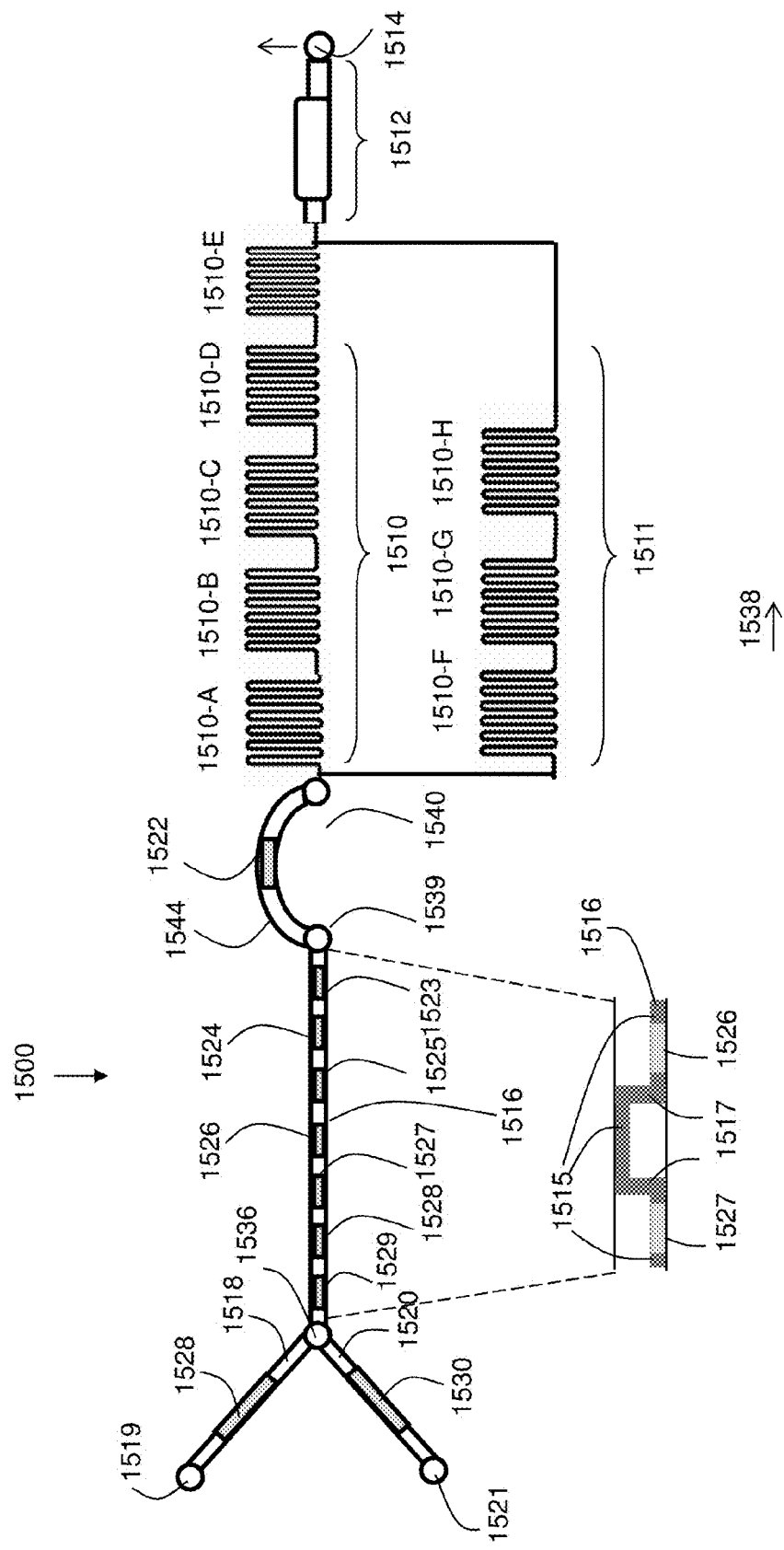
FIG. 14 is a schematic diagram showing a microfluidic system of a cassette that can be used to determine one or more blood markers in accordance with some embodiments of the invention.

This is a prophetic example describing the use of a cassette and analyzer to perform an assay to detect iPSA, fPSA, tPSA and hK2 in a sample by electrolessly depositing silver onto gold particles that are associated with the sample. FIG. 14 includes a schematic illustration of a microfluidic system 1500 of a cassette used in this example. The cassette had a similar shape to cassette 520 shown in FIG. 7.

The microfluidic system included analysis regions 1510A-1510F, waste containment region 1512, and an outlet 1514. The analysis regions included a microfluidic channel 50 microns deep and 120 microns wide, with a total length of 175 mm. The microfluidic system also included microfluidic channel 1516 and channel branches 1518 and 1520 (with inlets 1519 and 1521, respectively). Channel branches 1518 and 1520 were 350 microns deep and 500 microns wide. Channel 1516 was formed of sub-channels 1515, which were 350 microns deep and 500 microns wide located on alternating sides of the cassette, connected by through holes 1517 having a diameter of approximately 500 microns. Although FIG. 14 shows that reagents were stored on a single side of the cassette, in other embodiments, reagents were stored on both sides of the cassette. Channel 1516 had a total length of 390 mm, and branches 1518 and 1520 were each 360 mm long. Before sealing the channels, anti-PSA and anti-hK2 capture antibodies were attached to surfaces of the microfluidic system in segments of the analysis regions 1510 and 1511, as described in more detail below.

Prior to first use, the microfluidic system was loaded with liquid reagents which were stored in the cassette. A series of 7 wash plugs 1523-1529 (either water of buffer, approximately 2 microliters each) were loaded using a pipette into sub-channels 1515 of channel 1516 using the thru-holes. Each of the wash plugs was separated by plugs of air. Fluid 1528, containing a solution of silver salt, was loaded into branching channel through port 1519 using a pipette. Fluid 1530, containing a reducing solution, was loaded into branching channel 1520 through port 1521. Each of the liquids shown were separated from the other liquids by plugs of air. Ports 1514, 1519, 1521, 1536, 1539, and 1540 were sealed with an adhesive tape that can be easily removed or pierced. As such, the liquids were stored in the microfluidic system prior to first use.

At first use, the ports 1514, 1519, 1521, 1536, 1539, and 1540 were unsealed by a user peeling off a tape covering the opening of the ports. A tube 1544 containing lyophilized anti-PSA and anti-hK2 antibodies labeled with colloidal gold and to which 10 microliters of sample blood (1522) was added, was connected to ports 1539 and 1540. The tube was part of a fluid connector having a shape and configuration shown in FIG. 7. This created a fluidic connection between analysis region 1510 and channel 1516, which were otherwise unconnected and not in fluid communication with one another prior to first use.

The cassette including microfluidic system 1500 was inserted into an opening of an analyzer. The housing of the analyzer included an arm positioned within the housing that was configured to engage a cammed surface on the cassette. The arm extended at least partially into the opening in the housing such that as the cassette was inserted into the opening, the arm was pushed away from the opening into a second position allowing the cassette to enter the opening. Once the arm engaged the inwardly cammed surface of the cassette, the cassette was positioned and retained within the housing of the analyzer, and the bias of the spring prevented the cassette from slipping out of the analyzer. The analyzer senses the cassette's insertion by means of a position sensor.

An identification reader (RFID reader) positioned within the housing of the analyzer was used to read an RFID tag on the cassette which includes lot identification information. The analyzer used this identifier to match lot information (e.g., calibration information, expiration date of the cassette, verification that the cassette is new, and the type of analysis/assay to be performed in the cassette) stored in the analyzer. The user was prompted to input information about the patient (from which the sample was acquired) into the analyzer using the touch screen. After the information about the cassette was verified by the user, the control system initiated the analysis.

The control system included programmed instructions to perform the analysis. To initiate the analysis, a signal was sent to the electronics controlling a vacuum system, which was a part of the analyzer and used to provide fluid flow. A manifold with o-rings was pressed against the cassette surface by a solenoid. One port on the manifold sealed (by an o-ring) to port 1536 of the microfluidic system of the cassette. This port on the manifold was connected by a tube to a simple solenoid valve which was open to the atmosphere. A separate vacuum port on the manifold sealed (by-o-ring) to port 1514 of the microfluidic system of the cassette. A vacuum of approximately −30 kPa was applied to port 1514. Throughout the analysis, the channel including analysis region 1510 positioned between ports 1540 and 1514 had a substantially constant non-zero pressure drop of approximately −30 kPa. Sample 1522 was flowed in the direction of arrow 538 into each of analysis regions 1510A-1510H. As the fluid passed through the analysis regions, the PSA and hK2 proteins in sample 1522 were captured by anti-PSA and anti-hK2 antibodies immobilized on the analysis region walls, as described in more detail below. The sample took about 7-8 minutes to pass through the analysis regions, after which the remaining sample was captured in the waste containment region 1512.

Initiation of the analysis also involved the control system sending a signal to the optical detectors, which were positioned adjacent each of analysis regions 1510, to initiate detection. Each of the detectors associated with the analysis regions recorded the transmission of light through the channels of the analysis regions. As the sample passed by each of the analysis regions, peaks were produced. The peaks (and troughs) measured by the detectors are signals (or are converted to signals) that are sent to the control system which compared the measured signals to reference signals or values pre-programmed into the control system. The control system included a pre-programmed set of instructions for providing feedback to the microfluidic system based at least in part on the comparison of signals/values.

In a first analysis region 1510-A of device 1500 of FIG. 14, the walls of the channel of this analysis region were blocked with a blocking protein (Bovine Serum Albumin) prior to first use (e.g., prior to sealing the device). Little or no proteins in the blood sample attached to the walls of the analysis region 1510-A (except for perhaps some non-specific binding which may be washed off). This first analysis region acted as a negative control.

In a second analysis region 1510-B, the walls of the channel of this analysis region were coated with a predetermined large quantity of a prostate specific antigen (PSA) prior to first use (e.g., prior to sealing the device) to act as a high or positive control. As the blood sample passed through the second analysis region 1510-B, little or no PSA proteins in the blood bound to the walls of the channel. Gold conjugated signal antibodies in the sample may not yet be bound to the PSA in the sample, and thus they may bind to the PSA on the walls of the channel to act as a high or positive control.

In a third analysis region 1510-C, the walls of the channel of this analysis region were coated with the capture antibody, an anti-iPSA antibody, which binds to a different epitope on the iPSA protein than the gold conjugated signal antibody. The walls were coated prior to first use (e.g., prior to sealing the device). As the blood sample flowed through the fourth analysis region during use, iPSA proteins in the blood sample bound to the anti-iPSA antibody in a way that is proportional to the concentration of these proteins in the blood. Since the sample, which included iPSA, also included gold-labeled anti-iPSA antibodies coupled to the iPSA, the iPSA captured on the analysis region walls formed a sandwich immunocomplex.

In a fourth analysis region 1510-D, the walls of the channel of this analysis region were coated with the capture antibody, an anti-fPSA antibody, which binds to a different epitope on the fPSA protein than the gold conjugated signal antibody. The walls were coated prior to first use (e.g., prior to sealing the device). As the blood sample flowed through the fourth analysis region during use, fPSA proteins in the blood sample bound to the anti-fPSA antibody in a way that is proportional to the concentration of these proteins in the blood. Since the sample, which included fPSA, also included gold-labeled anti-fPSA antibodies coupled to the fPSA, the fPSA captured on the analysis region walls formed a sandwich immunocomplex.

In a fifth analysis region 1510-E, the walls of the channel of this analysis region were coated with the capture antibody, an anti-tPSA antibody, which binds to a different epitope on the tPSA protein than the gold conjugated signal antibody. The walls were coated prior to first use (e.g., prior to sealing the device). As the blood sample flowed through the fifth analysis region during use, tPSA proteins in the blood sample bound to the anti-tPSA antibody in a way that is proportional to the concentration of these proteins in the blood. Since the sample, which included tPSA, also included gold-labeled anti-tPSA antibodies coupled to the tPSA, the tPSA captured on the analysis region walls formed a sandwich immunocomplex.

Although gold-labeled anti-iPSA, anti-fPSA and anti-tPSA antibodies can be used, in other embodiments gold-labeled anti-PSA antibodies that bind to any PSA protein can be used for detection.

The first, second, third, fourth and fifth analysis regions were formed on a single substrate layer. Sixth (1510-F), seventh (1510-G) and eighth (1510-H) analysis regions were formed on a separate substrate layer (1511).

In the sixth analysis region 1510-F, the walls of the channel of this analysis region were coated with the capture antibody, an anti-hK2 antibody, which binds to a different epitope on the hK2 protein than the gold conjugated signal antibody. The walls were coated prior to first use (e.g., prior to sealing the device). As the blood sample flowed through the sixth analysis region during use, hK2 proteins in the blood sample bound to the anti-hK2 antibody in a way that is proportional to the concentration of these proteins in the blood. Since the sample, which included hK2, also included gold-labeled anti-hK2 antibodies coupled to the hK2, the hK2 captured on the analysis region walls formed a sandwich immunocomplex.

The seventh analysis region 1510-G may be used as a negative control as described above for analysis region 1510-A. The eighth analysis region 1510-H may be used as a high or positive control as described above for analysis region 1510-B.

Optionally, a ninth analysis region (not shown) can be used as a low control. In such an embodiment, the walls of the channel of this analysis region can be coated with a predetermined low quantity of PSA prior to first use (e.g., prior to sealing the device) to act as a low control. As the blood sample flowed through this analysis region, little or no PSA proteins in the sample bind to the wall of the channel. Gold conjugated signal antibodies in the sample may bind to the PSA on the walls of the channel to act as a low control.

Wash fluids 1523-1529 followed the sample through the analysis regions 1510 towards waste containment region 1512 in the direction of arrow 1538. As the wash fluids were passed through the analysis regions, they washed away remaining unbound sample components. Each wash plug cleaned the channels of the analysis regions, providing progressively more complete cleaning. The last wash fluid 1529 (water) washed away salts that could react with silver salts (e.g., chloride, phosphate, azide).

Figure 15:
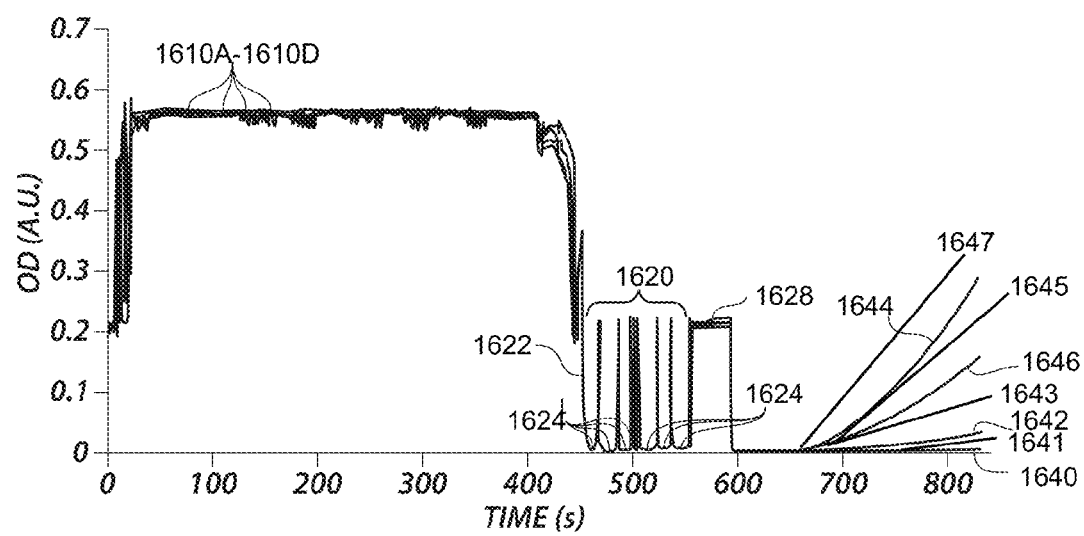
FIG. 15 is a plot showing measurement of optical density as a function of time showing determination of one or more blood markers in accordance with some embodiments of the invention.

As shown in the plot illustrated in FIG. 15, while the wash fluids were flowing through the analysis regions, each of the detectors associated with the analysis regions measures a pattern 1620 of peaks and troughs. The troughs corresponded to the wash plugs (which are clear liquids and thus provide maximum light transmission). The peaks between each plug represent the air between each plug of clear liquid. Since the assay included 7 wash plugs, 7 troughs and 7 peaks are present in plot 1600. The first trough 1622 is generally not as deep as the other troughs 1624 since the first wash plug often catches blood cells left in the channel and thus is not completely clear.

The final peak of air 1628 is much longer than the previous peaks because there were no wash plugs to follow. As a detector detects the length of this air peak, one or more signals is sent to the control system which compares the length of time of this peak to a pre-set reference signal or input value having a particular length. If the length of time of the measured peak is long enough compared to the reference signal, the control system sends a signal to the electronics controlling vent valve 1536 to actuate the valve and initiate mixing of fluids 1528 and 1530. (Note that the signal of peak of air 1628 may be combined with a signal indicating either 1) the intensity of the peak; 2) where this peak is positioned as a function of time, and/or 3) one or more signals indicating that a series of peaks 1620 of particular intensity has already passed. In this way, the control system distinguishes peak of air 1628 from other peaks of long duration such as peak 1610 from the sample, e.g., using a pattern of signals.)

Referring again to FIG. 14, to initiate mixing, the solenoid connected by the manifold to vent port 1536 is closed. Since the vacuum remains on and no air can enter through vent valve 1536, air enters the device through ports 1519 and 1521 (which are open). This forces the two fluids 1528 and 1530 in the two storage channels upstream of vent valve 1536 to move substantially simultaneously toward outlet 1514. These reagents mix at the intersection of the channels to form an amplification reagent (a reactive silver solution) having a viscosity of about $1\times10^{-3}$ Pa·s. The ratio of the volumes of fluids 1528 and 1530 was about 1:1. The amplification reagent continued through the downstream storage channel, through tube 1544, through analysis regions 1510, and then to waste containment region 1512. After a set amount of time (12 seconds), the analyzer reopened vent valve 1536 such that air flows through vent valve 1536 (instead of the vent ports). This left some reagent behind in the upstream storage channels 1518 and 1520 on the device. This also results in a single plug of mixed amplification reagent. The 12 seconds of vent-valve closure results in an amplification plug of approximately 50 µL. (Instead of simple timing, another way to trigger the re-opening of the vent valve would be to detect the amplification reagent as it first enters the analysis regions.)

Because the mixed amplification reagent is stable for only a few minutes (usually less than 10 minutes), the mixing was performed less than a minute before use in analysis region 1510. The amplification reagent is a clear liquid, so when it enters the analysis regions, optical density is at its lowest. As the amplification reagent passed across the analysis regions, silver was deposited on the captured gold particles to increase the size of the colloids to amplify the signal. (As noted above, gold particles may be present in the low and high positive control analysis regions and, to the extent that PSA and hK2 were present in the sample, in the test analysis region.) Silver can then be deposited on top of the already deposited silver, leaving more and more silver deposited in the analysis regions. Eventually the deposited silver reduces the transmission of light through the analysis regions. The reduction in transmitted light is proportional to the amount of silver deposited and can be related to the amount of gold colloids captured on the channel walls. In an analysis region where no silver is deposited (the negative control for example, or the test area when the sample contains none of the target protein), there will be no (or minimal) increase in optical density. In an analysis region with significant silver deposition, the slope and ultimate level of the pattern of increasing optical density will be high. The analyzer monitors the pattern of this optical density during amplification in the test area to determine the concentration of analyte in the sample. In one version of the test, the pattern is monitored within the first three minutes of amplification. The optical density in each of the analysis regions as a function of time was recorded and are shown as curves 1640-1647 in FIG. 14. These curves corresponded to signals that were produced in the analysis regions. After three minutes of amplification, the analyzer stops the test. No more optical measurements are recorded and the manifold is disengaged from the device.

From the curves, values (e.g., concentrations) of the blood markers (e.g., iPSA, fPSA, tPSA and/or hK2) are determined using a computer (e.g., within the analyzer). The values are sent to a processor (which is in electronic communication with the analyzer) that is programmed to evaluate a logistic regression model (e.g., as described herein) based, at least in part, on the received values to determine a probability of risk of prostate cancer in the patient, an indication of an estimated prostate gland volume, and/or an indication of a likelihood that a prostate cancer biopsy will be positive in the patient.

The test result is displayed on the analyzer screen and communicated to a printer, computer, or whatever output the user has selected. The user may remove the device from the analyzer and throw it away. The sample and all the reagents used in the assay remain in the device. The analyzer is ready for another test.

This prophetic example shows that analysis of a sample containing iPSA, fPSA, tPSA and/or hK2 can be performed in a single microfluidic system using an analyzer that controls fluid flow in the cassette, and by using feedback from one or more measured signals to modulate fluid flow. This prophetic example also shows that the results from such an analysis can be used to determine a probability of risk of prostate cancer in the patient, an indication of an estimated prostate gland volume, and/or an indication of a likelihood that a prostate cancer biopsy will be positive in the patient.

The invention claimed is:

1. An assay system comprising:
an analysis region comprising one or more binding partners immobilized to a solid phase portion therein, wherein the one or more binding partners are selected from a group consisting of binding partners that bind total prostate-specific antigen (tPSA), binding partners that bind free prostate-specific antigen (fPSA), binding partners that bind intact prostate-specific antigen (iPSA) and binding partners that bind human kallikrein 2 (hK2);
a detection device, the detection device being configured to detect a presence of an analyte in a sample from the analysis region, wherein the analyte is selected from a group consisting of tPSA, fPSA, iPSA, and hK2; and
a computer programmed to:
process information determined by the detection device indicative of the presence of the analyte, wherein the information includes information for fPSA and tPSA, wherein processing the information determined by the detection device comprises:
defining a first cubic spline and a second cubic spline for tPSA, wherein each of the first cubic spline and the second cubic spline is defined using a first internal knot between 2-5 and a second internal knot between 5-8;
defining a third cubic spline and a fourth cubic spline for fPSA, wherein each of the third cubic spline and fourth cubic spline is defined using a third internal knot between 0.25-1 and a fourth internal knot between 1.0-2.0;
calculating a first tPSA value by evaluating the first cubic spline using the received tPSA value;
calculating a second tPSA value by evaluating the second cubic spline using the received tPSA value;
calculating a first fPSA value by evaluating the third cubic spline using the received fPSA value;
calculating a second fPSA value by evaluating the fourth cubic spline using the received fPSA value;
evaluating a logistic regression model that includes the first tPSA value, the second tPSA value, the first fPSA value, and the second fPSA value to determine a logit;
determining a probability of an event associated with prostate cancer based, at least in part, on the logit; and
outputting an indication of the probability of the event associated with prostate cancer.

2. The assay system of claim 1, wherein evaluating a logistic regression model comprises scaling the first tPSA value by a first coefficient and scaling the second tPSA value by a second coefficient value to produce scaled tPSA values and summing the scaled tPSA values; and
wherein evaluating a logistic regression model further comprises scaling the first fPSA value by a third coefficient and scaling second fPSA value by a fourth coefficient to produce scaled fPSA values and summing the scaled fPSA values.

3. The assay system of claim 1, wherein the input includes information for iPSA and hK2, and wherein evaluating the logistic regression model further includes terms based, at least in part, on the information for iPSA, and the information for hK2.

4. The assay system of claim 1, wherein the first internal knot is specified as 3.89, the second internal knot is specified as 5.54, the third internal knot is specified as 0.81, and the fourth internal knot is specified as 1.19.

5. The assay system of claim 1, wherein outputting an indication of the probability of the event associated with prostate cancer comprises outputting an indication of an estimated prostate gland volume.

6. The assay system of claim 1, wherein outputting an indication of the probability of the event associated with prostate cancer comprises outputting an indication of a likelihood that a prostate cancer biopsy will be positive.

7. The assay system of claim 1, wherein the detection device utilizes an optical or luminescent detection technique selected from the group consisting of light transmission, light absorbance, light scattering, light reflection, visual techniques, photoluminescence, fluorescence, chemiluminescence, bioluminescence, and electrochemiluminescence.

8. The assay system of claim 1, wherein the detection device detects chemiluminescent or fluorescent emissions, and wherein the chemiluminescent or fluorescent emissions are indicative of an analyte bound to the analyte binding partner.

9. The assay system of claim 1, wherein the detection device detects variation of a light signal as a function of time.

10. The assay system of claim 1, wherein the sample is whole blood, serum, or plasma.

11. The assay system of claim 1, wherein the analysis region comprises a microfluidic channel including at least one inlet and one outlet.

12. A method, comprising:
detecting, by a detection device, a presence of an analyte in a sample from an analysis region of an assay system comprising one or more binding partners immobilized to a solid phase portion therein, wherein the one or more binding partners are selected from a group consisting of binding partners that bind total prostate-specific antigen (tPSA), binding partners that bind free prostate-specific antigen (fPSA), binding partners that bind intact prostate-specific antigen (iPSA) and binding partners that bind human kallikrein 2 (hK2), wherein the analyte is selected from a group consisting of tPSA, fPSA, iPSA, and hK2;
processing, by at least one computer processor, information determined by the detection device indicative of the presence of the analyte, wherein the input includes information for fPSA and tPSA, and wherein processing the information determined by the detection device comprises:
defining, by the at least one computer processor, a first cubic spline and a second cubic spline for tPSA, wherein each of the first cubic spline and the second cubic spline is defined using a first internal knot between 2-5 and a second internal knot between 5-8;
defining, by the at least one computer processor, a third cubic spline and a fourth cubic spline for fPSA, wherein each of the third cubic spline and fourth cubic spline is defined using a third internal knot between 0.25-1 and a fourth internal knot between 1.0-2.0;
calculating, by the at least one computer processor, a first tPSA value by evaluating the first cubic spline using the received tPSA value;
calculating, by the at least one computer processor, a second tPSA value by evaluating the second cubic spline using the received tPSA value;
calculating, by the at least one computer processor, a first fPSA value by evaluating the third cubic spline using the received fPSA value;
calculating, by the at least one computer processor, a second fPSA value by evaluating the fourth cubic spline using the received fPSA value;
evaluating, by the at least one computer processor, a logistic regression model that includes the first tPSA value, the second tPSA value, the first fPSA value, and the second fPSA value to determine a logit;
determining, by the at least one computer processor, a probability of an event associated with prostate cancer based, at least in part, on the logit; and
outputting an indication of the probability of the event associated with prostate cancer.

13. A non-transitory computer-readable storage medium encoded with a plurality of instructions that, when executed by a computer, perform a method, wherein the method comprises:

detecting, by a detection device, a presence of an analyte in a sample from an analysis region of an assay system comprising one or more binding partners immobilized to a solid phase portion therein, wherein the one or more binding partners are selected from a group consisting of binding partners that bind total prostate-specific antigen (tPSA), binding partners that bind free prostate-specific antigen (fPSA), binding partners that bind intact prostate-specific antigen (iPSA) and binding partners that bind human kallikrein 2 (hK2), wherein the analyte is selected from a group consisting of tPSA, fPSA, iPSA, and hK2;

processing, by at least one computer processor, information determined by the detection device indicative of the presence of the analyte, wherein the input includes information for fPSA and tPSA, wherein processing the information determined by the detection device comprises:

defining a first cubic spline and a second cubic spline for tPSA, wherein each of the first cubic spline and the second cubic spline is defined using a first internal knot between 2-5 and a second internal knot between 5-8;

defining a third cubic spline and a fourth cubic spline for fPSA, wherein each of the third cubic spline and fourth cubic spline is defined using a third internal knot between 0.25-1 and a fourth internal knot between 1.0-2.0;

calculating a first tPSA value by evaluating the first cubic spline using the received tPSA value;

calculating a second tPSA value by evaluating the second cubic spline using the received tPSA value;

calculating a first fPSA value by evaluating the third cubic spline using the received fPSA value;

calculating a second fPSA value by evaluating the fourth cubic spline using the received fPSA value;

evaluating a logistic regression model that includes the first tPSA value, the second tPSA value, the first fPSA value, and the second fPSA value to determine a logit;

determining a probability of an event associated with prostate cancer based, at least in part, on the logit; and outputting an indication of the probability of the event associated with prostate cancer.

* * * * *